(12) United States Patent
Youngblood et al.

(10) Patent No.: US 10,986,933 B2
(45) Date of Patent: Apr. 27, 2021

(54) ARTICLE COMPRISING A TEMPERATURE-CONDITIONED SURFACE, THERMOELECTRIC CONTROL UNIT, AND METHOD FOR TEMPERATURE-CONDITIONING THE SURFACE OF AN ARTICLE

(71) Applicant: Youngblood IP Holdings, LLC, Mooresville, NC (US)

(72) Inventors: Todd Youngblood, Mooresville, NC (US); Tara Youngblood, Mooresville, NC (US)

(73) Assignee: KRYO, INC., Mooresville, NC (US)

( * ) Notice: Subject to any disclaimer, the term of this patent is extended or adjusted under 35 U.S.C. 154(b) by 713 days.

(21) Appl. No.: 15/705,829

(22) Filed: Sep. 15, 2017

(65) Prior Publication Data
US 2018/0000255 A1    Jan. 4, 2018

Related U.S. Application Data

(63) Continuation-in-part of application No. 14/777,050, filed as application No. PCT/US2014/030202 on Mar. 17, 2014, now Pat. No. 10,278,511.
(Continued)

(51) Int. Cl.
*A47C 21/04* (2006.01)
*A47C 31/00* (2006.01)
(Continued)

(52) U.S. Cl.
CPC ............ *A47C 21/04* (2013.01); *A47C 21/022* (2013.01); *A47C 21/044* (2013.01);
(Continued)

(58) Field of Classification Search
CPC .......... A47C 7/74; A47C 7/742; A47C 7/744; A47C 7/748; A47C 21/04; A47C 21/042;
(Continued)

(56) References Cited

U.S. PATENT DOCUMENTS 2,753,435 A     7/1956  Ivar
3,230,556 A *   1/1966  Shippee ............... A47C 21/048
                                                5/423
(Continued)

FOREIGN PATENT DOCUMENTS

KR      20110102637 A       9/2011
WO      2014145436 A1       9/2014

OTHER PUBLICATIONS

U.S. Appl. No. 61/800,768 Youngblood,Thermo electric heating and cooling device, filed Mar. 15, 2013, Drawings and Specification.
(Continued)

*Primary Examiner* — Nicholas F Polito
(74) *Attorney, Agent, or Firm* — NEO IP

(57) ABSTRACT

The present invention provides systems, methods, and articles for temperature conditioning a surface. An article is formed from a first layer having a plurality of openings and a second layer having a corresponding plurality of openings. At least one interior chamber constructed and configured to retain a fluid without leaking is defined between an interior surface of the first layer and an interior surface of the second layer. At least one flexible fluid supply line delivers the fluid to the at least one interior chamber. At least one flexible fluid return line removes the fluid from the at least one interior chamber. At least one control unit that is operable to selectively cool or heat the fluid is attached to the at least one flexible fluid supply line and the at least one flexible fluid return line.

18 Claims, 39 Drawing Sheets

Related U.S. Application Data

(60) Provisional application No. 62/398,257, filed on Sep. 22, 2016, provisional application No. 61/800,768, filed on Mar. 15, 2013.

(51) Int. Cl.
| | |
|---|---|
| *F25D 15/00* | (2006.01) |
| *A47C 27/08* | (2006.01) |
| *A61B 5/00* | (2006.01) |
| *A47C 21/02* | (2006.01) |
| *A47C 31/10* | (2006.01) |
| *F25D 17/02* | (2006.01) |
| *F25D 29/00* | (2006.01) |
| *A47G 9/02* | (2006.01) |
| *F25B 21/02* | (2006.01) |
| *F28F 3/12* | (2006.01) |
| *F28D 1/03* | (2006.01) |
| *A61B 5/021* | (2006.01) |
| *A61B 5/0205* | (2006.01) |
| *A61B 5/08* | (2006.01) |
| *A61B 5/024* | (2006.01) |
| *A61B 5/11* | (2006.01) |
| *A61B 5/145* | (2006.01) |
| *A61B 5/0531* | (2021.01) |
| *A61B 5/1455* | (2006.01) |
| *F28D 21/00* | (2006.01) |
| *A61B 5/369* | (2021.01) |
| *A61B 5/389* | (2021.01) |
| *A61B 5/398* | (2021.01) |

(52) U.S. Cl.
CPC .......... *A47C 21/048* (2013.01); *A47C 27/085* (2013.01); *A47C 31/008* (2013.01); *A47C 31/105* (2013.01); *A47G 9/0246* (2013.01); *A61B 5/4812* (2013.01); *F25B 21/02* (2013.01); *F25D 15/00* (2013.01); *F25D 17/02* (2013.01); *F25D 29/00* (2013.01); *F28D 1/035* (2013.01); *F28F 3/12* (2013.01); *A61B 5/021* (2013.01); *A61B 5/02055* (2013.01); *A61B 5/02438* (2013.01); *A61B 5/0531* (2013.01); *A61B 5/0816* (2013.01); *A61B 5/11* (2013.01); *A61B 5/1114* (2013.01); *A61B 5/14532* (2013.01); *A61B 5/14551* (2013.01); *A61B 5/369* (2021.01); *A61B 5/389* (2021.01); *A61B 5/398* (2021.01); *A61B 2560/0247* (2013.01); *F25B 2321/0252* (2013.01); *F28D 2021/0077* (2013.01); *F28F 2255/02* (2013.01)

(58) Field of Classification Search
CPC ... A47C 21/044; A47C 21/048; A47C 27/085; A47C 27/144; A61F 2007/0054; A61F 2007/0056

See application file for complete search history.

(56) References Cited

U.S. PATENT DOCUMENTS

| | | | |
|---|---|---|---|
| 4,132,262 A | 1/1979 | Wibell | |
| 4,459,468 A | 7/1984 | Bailey | |
| 4,777,802 A | 10/1988 | Feher | |
| 4,858,609 A | 8/1989 | Cole | |
| 5,033,136 A | 7/1991 | Elkins | |
| 5,304,112 A | 4/1994 | Mrklas et al. | |
| 5,329,096 A | 7/1994 | Suematsu | |
| 5,448,788 A | 9/1995 | Wu | |
| 5,894,615 A | 4/1999 | Alexander | |
| 5,948,303 A | 9/1999 | Larson | |
| 6,163,907 A | 12/2000 | Larson | |
| 6,273,810 B1 | 8/2001 | Rhodes, Jr. et al. | |
| 6,371,976 B1* | 4/2002 | Vrzalik | A61F 7/0097 5/606 |
| 6,484,062 B1 | 11/2002 | Kim | |
| 6,581,224 B2 | 6/2003 | Yoon | |
| 6,826,792 B2 | 12/2004 | Lin | |
| 7,041,049 B1 | 5/2006 | Raniere | |
| 7,238,289 B2 | 7/2007 | Suddath | |
| 7,248,915 B2 | 7/2007 | Rönnholm | |
| 7,306,567 B2 | 12/2007 | Loree | |
| 7,460,899 B2 | 12/2008 | Almen | |
| 7,524,279 B2 | 4/2009 | Auphan | |
| 7,608,041 B2 | 10/2009 | Sutton | |
| 7,699,785 B2 | 4/2010 | Nemoto | |
| 7,868,757 B2 | 1/2011 | Radivojevic et al. | |
| 8,096,960 B2 | 1/2012 | Loree et al. | |
| 8,179,270 B2 | 5/2012 | Rai et al. | |
| 8,191,187 B2 | 6/2012 | Brykalski et al. | |
| 8,290,596 B2 | 10/2012 | Wei et al. | |
| 8,348,840 B2 | 1/2013 | Heit et al. | |
| 8,418,285 B2 | 4/2013 | Frias | |
| 8,529,457 B2 | 9/2013 | Devot et al. | |
| 8,617,044 B2 | 12/2013 | Pelgrim et al. | |
| 8,768,520 B2 | 7/2014 | Oexman et al. | |
| 9,196,479 B1 | 11/2015 | Cheng et al. | |
| 9,402,763 B2* | 8/2016 | Bledsoe | A61F 7/10 |
| 2002/0014951 A1 | 2/2002 | Kramer et al. | |
| 2002/0080035 A1 | 6/2002 | Youdenko | |
| 2002/0124574 A1 | 9/2002 | Guttman et al. | |
| 2004/0049132 A1 | 3/2004 | Barron et al. | |
| 2005/0143617 A1 | 6/2005 | Auphan | |
| 2006/0137099 A1* | 6/2006 | Feher | B60N 2/5657 5/713 |
| 2006/0293602 A1 | 12/2006 | Clark | |
| 2006/0293608 A1 | 12/2006 | Rothman et al. | |
| 2008/0234785 A1 | 9/2008 | Nakayama et al. | |
| 2009/0288800 A1 | 11/2009 | Kang et al. | |
| 2010/0011502 A1* | 1/2010 | Brykalski | A47C 21/04 5/423 |
| 2010/0100004 A1 | 4/2010 | Someren | |
| 2010/0174198 A1* | 7/2010 | Young | A61B 5/1126 600/484 |
| 2010/0199687 A1 | 8/2010 | Woods et al. | |
| 2011/0015495 A1 | 1/2011 | Dothie et al. | |
| 2011/0073292 A1 | 3/2011 | Datta et al. | |
| 2011/0107514 A1 | 5/2011 | Brykalski et al. | |
| 2011/0230790 A1 | 9/2011 | Kozlov | |
| 2011/0247139 A1 | 10/2011 | Tallent et al. | |
| 2011/0267196 A1 | 11/2011 | Hu et al. | |
| 2013/0019611 A1 | 1/2013 | Sims et al. | |
| 2013/0060306 A1 | 3/2013 | Colbauch | |
| 2013/0234823 A1 | 9/2013 | Kahn et al. | |
| 2014/0316495 A1* | 10/2014 | Augustine | H05B 3/342 607/112 |
| 2015/0093101 A1 | 4/2015 | Lee | |
| 2015/0289666 A1* | 10/2015 | Chandler | A47C 27/083 5/423 |
| 2016/0015315 A1* | 1/2016 | Auphan | A61B 5/6892 600/301 |
| 2016/0029808 A1 | 2/2016 | Youngblood et al. | |
| 2016/0151603 A1 | 6/2016 | Shouldice et al. | |
| 2016/0235610 A1 | 8/2016 | Drake | |
| 2017/0053068 A1 | 2/2017 | Pillai et al. | |

OTHER PUBLICATIONS

U.S. Appl. No. 62/398,257, Youngblood,Bed Pad With Custom Modulated Temperature Adjustment , filed Sep. 22, 2016, Drawings and Specification.

Buysse, D.J., Reynolds, C.F., Monk, T.H., Berman, S.R., & Kupfer, D.J. (1989). The Pittsburgh Sleep Quality Index (PSQI): A new instrument for psychiatric research and practice. Psychiatry Research, 28(2), 193-213.

Quan, S. F. et. al; "Healthy Sleep The Characteristics of Sleep" (Sep. 21, 2016) pp. 1-4, retrieved from http://healthysleep.med.harvard.edu/healthy/science/what/characteristics.

(56) References Cited

OTHER PUBLICATIONS

Tobaldini, E. et. al; "Heart rate variability in normal and pathological sleep", Frontiers in Physiology, (Oct. 16, 2013), p. 1-11, vol. 4, Article 294, doi: 10.3389/fphys.2013.00294.

* cited by examiner

Profile

John Kensington
UI/UX Designer & Developer

Sydney, Australia

863
FOLLOWERS

2471
PHOTOS

1593
LIKES

Daily load: 59%           39 users

••••• AT&T 🛜     9:41 AM     100% ▰

Pravin ⌄ 
Today

---

Weekdays     10 PM     06 AM
Mon, Tue, Wed, Thu, Fri     Sleep time     Wake up time

Weekends     10 PM     06 AM
Sat, Sun     Sleep time     Wake up time

[ Add Sleep Profile → ]

•••• AT&T 🛜     9:41 AM     100% ▰

Pravin ⌄ 
Today

Weekdays     01 PM     03 PM
Mon, Tue, Wed, Thu, Fri     Sleep time     Wake up time

11 PM     05 AM
    Sleep time     Wake up time

Weekends     01 PM     03 PM
Sat, Sun     Sleep time     Wake up time

02 AM     09 AM
    Sleep time     Wake up time

[ Add Sleep Profile → ]

ARTICLE COMPRISING A TEMPERATURE-CONDITIONED SURFACE, THERMOELECTRIC CONTROL UNIT, AND METHOD FOR TEMPERATURE-CONDITIONING THE SURFACE OF AN ARTICLE

CROSS REFERENCE TO RELATED APPLICATIONS

This application is related to and claims priority from the following US patents and patent applications: this application is a continuation-in-part of U.S. application Ser. No. 14/777,050, filed Sep. 15, 2015, which is the National Stage of International Application No. PCT/US2014/030202, filed Mar. 17, 2014, which claims the benefit of U.S. Provisional Application No. 61/800,768, filed Mar. 15, 2013. This application also claims the benefit of U.S. Provisional Application No. 62/398,257, filed Sep. 22, 2016. Each of the above applications is incorporated herein by reference in its entirety.

BACKGROUND OF THE INVENTION

1. Field of the Invention

This invention relates broadly and generally to an article comprising a temperature-conditioned surface, thermoelectric control unit, and method for temperature-conditioning the surface of an article.

2. Description of the Prior Art

It is generally known in the prior art to provide a temperature-conditioned surface. It is desirable to control the temperature of a bed or other piece of furniture that supports a person, such as when sleeping. Such control has therapeutic value in treating symptoms of menopause or conditions of hypothermia or hyperthermia, particularly when those conditions manifest themselves over a long period of time. Therapeutic value may also be seen for individuals who have circulatory disorders, sleep disorders, and other conditions that may be improved by increasing the comfort felt during sleep. Such control can be desirable even outside the therapeutic value of cooling or heating a surface (e.g., mattress), simply to match the personal comfort preferences of healthy individuals, to promote higher quality sleep, or to provide localized control when a more general control (e.g., heating or air conditioning of a sleeping space) is unavailable or when adjustments to the general control would cause others discomfort or would be inefficient from an energy consumption perspective.

Various methods of temperature control are known, including such classic systems as electric blankets or heating pads, as well as more recent developments that involve the circulation of a heated or cooled fluid through a mattress, such as directing air through the chambers of an air mattress or directing air or a fluid through a tube that is embedded within a mattress or a mattress pad. The more advanced of these systems utilize a heat source or sink (i.e., cooling source) to heat or cool a reservoir of fluid to a selected target temperature and pump the heated or cooled fluid through the available conduit, relying on principles of heat exchange to control the surface temperature.

Prior art patent documents include the following:

U.S. Pat. No. 2,753,435 for thermal blanket by inventor Jepson, filed Apr. 23, 1954 and issued Aug. 3, 1956, is directed to blankets having heat transfer means included therein whereby the temperature of the same may be controlled in a desired manner.

U.S. Pat. No. 4,132,262 for heating and cooling blanket by inventor Wibell, filed Jan. 17, 1977 and issued Jan. 2, 1979, is directed to a cooling and heating blanket comprising a blanket enclosure with heating means including a plurality of flexible elements positioned within the enclosure for being electrically energized for supplying heat to the enclosure, such that the enclosure may be retained above room temperature, and cooling means including a plurality of flexible fluid carrying conduits positioned within the enclosure through which a heat transfer fluid can flow, such that the enclosure may be retained below room temperature. Control means including an electric motor and a pump driven thereby located remotely relative to the enclosure is provided with flexible conduit means connecting the enclosure and the cooling means, and regulating means is operatively associated with the heating means and the cooling means. The regulating means being adapted to energize the control means or the heating means in response to increases and decreases of the temperature associated with the enclosure, such that the temperature of the blanket may be retained above or below the room temperature in which the blanket is located.

U.S. Pat. No. 4,459,468 for temperature control fluid circulating system by inventor Bailey, filed Apr. 14, 1982 and issued Aug. 10, 1984, is directed to a fluid circulating system primarily designed for use with a thermal blanket or pad and being temperature controlled so that both heating and cooling effects may be produced through the preheating or precooling of fluid in a reservoir tank or like container which, wherein the fluid is in turn forced through the thermal blanket to provide the proper heating or cooling as desired. A standby switching mode is included to prevent circulation of the fluid through the thermal blanket by a pump structure until the fluid reaches a preselected temperature has been reached. Heating and cooling transfer elements are disposed to the fluid within the reservoir tank thereby eliminating the need for condensor structures and the like and allowing for a compact overall unit to provide the required fluid circulating throughout the thermal blanket.

U.S. Pat. No. 4,777,802 for blanket assembly and selectively adjustable apparatus for providing heated or cooled air thereto by inventor Feher, filed Apr. 23, 1987 and issued Oct. 18, 1988, is directed to a blanket assembly having an outer layer constructed of a relatively close weave fabric preventing air flow therethrough. Underneath the top layer is a second layer of material edge connected to the top layer and which is constructed of a material permeable to air, such as relatively thin taffeta, for example. A cavity exists between the two layers which receives pressurized cooled or heated air that passes through the air permeable layer to cool or heat the individual using the blanket assembly. A modified blanket assembly construction includes rigid edge wall members holding the outer and inner layers separated at a predetermined spacing reducing "pinch-off" between the layers restricting air flow within parts of the cavity or chamber. Peltier effect elements are selectively energizable to heat or cool air provided to the blanket assembly cavity.

U.S. Pat. No. 5,033,136 for bedding system with selective heating and cooling by inventor Elkins, filed Nov. 6, 1989 and issued Aug. 23, 1991, is directed to a bedding system providing for heating or cooling a person and for applying the heating or cooling only in areas of the bed where the person is located. A sealed three-ply heat transfer and insulating device covers the mattress, below the contour sheet or other covering which comes in contact with the person's body. A wicking contour sheet or other cover may optionally be used, capable of absorbing any condensation on the surface of the three-ply device. Between the lower two plies of the three-ply material is a channeled flow of coolant liquid, at a regulated temperature close to human skin temperature. Above these two plies, i.e. between the middle ply and the upper ply, is a sealed envelope containing slightly pressurized air. A light weight, well-insulated comforter is also recommended to isolate the sleeper from the thermal ambient environment.

U.S. Pat. No. 5,329,096 for heat storage mat by inventor Suematsu, filed Sep. 27, 1993 and issued Jul. 12, 1994, is directed to a heat storage mat for a bed constructed to provide a heating intensity, a heat insulation and a cushioning effect which are adjusted to meet various conditions which are required for various parts of the driver's body to insure a comfortable sleep. The heat storage mat includes a plurality of heating elements arranged in a row in a longitudinal direction of the mat. Each of the heating elements is composed of a flat bag filled with a latent heat storage agent and an electric heater unit disposed on an underside of the flat bag. The quantities of the latent heat storage agents associated with the respective heating elements increase successively in a direction from a head side toward a leg side of the mat. A plurality of heat insulating cushions are disposed on upper surfaces of the corresponding bags. The heat insulating cushions have thicknesses which vary in inverse proportion to the quantities of the latent heat storage agents of the respective bags. The heating elements and the heat insulating cushions are enclosed in a bag-like cover.

U.S. Pat. No. 5,448,788 for thermoelectric cooling-heating mattress by inventor Wu, filed Mar. 8, 1994 and issued Sep. 12, 1995, is directed to a thermostat controlled mattress including a mattress unit having an underlay, a surface cover and a curved circuit. A water circuit tube connects to the curved circuit so as to allow water to be introduced into the mattress unit with the aid of a pump. Water is circulated between the mattress unit and a water storage box via the water circuit tube. A sensor is operatively arranged with respect to the water storage box to sense the temperature and quantity of water contained in the water storage box and sends a signal to a thermostat electric circuit. An aluminum reservoir for the water is connected to the curved circuit of the mattress unit and the water circuit tube. A thermoelectric element is connected to the reservoir and the power supply to heat or cool the water. Water is circulated in the water circuit tube between the curved circuit of the mattress unit and the water storage box, through the reservoir. The water temperature is controlled based on signals generated by the thermostat electric circuit, which activates the power supply operatively connected to the thermoelectric element. A heat sink and a fan may be arranged adjacent to the thermoelectric element such that the fan blows a current of air onto the heat sink.

U.S. Pat. No. 5,894,615 for temperature selectively controllable body supporting pad by inventor Alexander, filed Apr. 30, 1997 and issued Apr. 20, 1999, is directed to a bed pad has embedded in it a circuit of continuous tubing. Portable heating and refrigerating means are operatively connected to a second tubing circuit by quick disconnect couplings. Electrical control means are selectively operated to heat or cool the liquid in said second tubing circuit. Thermostatic controls may optionally be applied to both the heating and refrigerating means. This has particular use in surgical operating rooms for raising and lowering the temperature of the patient. It is also useful in the recovery room, hospital and or convalescent home.

U.S. Pat. No. 5,948,303 for temperature control for a bed by inventor Larson, filed May 4, 1998 and issued Sep. 7, 1999, is directed to a temperature control apparatus for a bed including at least one heating element, mounted in a resting surface on a mattress of the bed for warming at least a first area of the resting area. A temperature sensor is located to detect the temperature of the first area of the resting area, and transmits the information to a central control unit. The central control unit includes a central processing unit which is interconnected with both the heating element and the temperature sensor to adjust the temperature in the first, area of the resting area as desired. The central control unit is also connected to a timer to permit programming of temperature changes as desired. An occupant sensor in the resting surface of the mattress will detect the presence and absence of an occupant, and transmit this information to the central control unit for processing.

U.S. Pat. No. 6,163,907 for removable mattress top assembly by inventor Larson, filed Apr. 3, 1998 and issued Dec. 26, 2000, is directed to a mattress top assembly for a mattress including a pad filled with cushioning material and a plurality of connector straps attached along the head, foot, arid side edges of the pad and removably connected to the side wall of the mattress. The mattress includes one part of a cooperable fastener generally midway between top and bottom surfaces, on the side walls of the mattress, for detachable connection of each of the straps thereto.

US Publication No. 2002/0124574 for thermoelectric air-condition apparatus by inventors Guttman et al., filed Dec. 14, 2000 and published Sep. 12, 2002, is directed to a thermoelectric air conditioning apparatus is comprised of a housing having a plurality of air inlets and a plurality of air outlets; a plurality of thermoelectric elements; two heat exchangers; a temperature regulator, having first and second air inlets, a main air outlet and at least one exhaust outlet; two air circulation units and a control unit. Thermoelectric elements are energized, and cause a reduction of temperature on one side and an increase of temperature on the other side. One air flow is forced to flow through one of the housing air inlets, over a heat exchanger and to the first air outlet of the temperature regulator. Another air flow is forced to flow through one of the housing inlets, over the other heat exchanger and to the second air outlet of the temperature regulator. The temperature of the air leaving the main outlet of the temperature regulator is determined by proportioning the flow of air from the first air inlet of the temperature regulator and the air flow from the second air inlet of the temperature regulator into and through the main outlet of the temperature regulator.

U.S. Pat. No. 6,581,224 for bed heating systems by inventor Yoon, filed Mar. 6, 2001 and issued Jun. 24, 2003, is directed to a heating system, e.g. for a bed mattress or floor sleeping area, having a tube extending in an array from a water inlet portion to a water outlet portion through a sinuous intermediate portion. The heating system has a longitudinal inner area extending centrally along the array and a pair of longitudinal outer areas extending at opposite sides of the inner area along the array. The intermediate portion has innermost runs distributed over the central area, where a sleeping person is most likely to lie, and connected directly to the inlet portion and to one another and outermost runs distributed over the outer areas and connected directly to the water outlet portion and to one another. A pump has an outlet connected through the water heater to the water inlet portion and an inlet connected to a water reservoir; and a water temperature and flow control device is connected to the pump and the water heater.

U.S. Pat. No. 6,826,792 for air mattress having temperature regulator by inventor Lin, filed Mar. 29, 2003 and issued Dec. 7, 2004, is directed to an air mattress device including an air mattress member, and a temperature regulator coupled to the air mattress member with a hose, to supply the regulated air into the air mattress member via the hose. The temperature regulator includes a casing disposed in a housing, a heat exchanging member disposed in the casing, to exchange heat with the air flowing into the casing. A heat dissipating device is disposed in the housing, a heat exchanger includes two conductors disposed between the heat dissipating device and the casing, to transmit heat between the heat dissipating device and the casing.

US Publication No. 2009/0288800 for cooling and heating cabinet device of rear seat for vehicles using thermoelectric element by inventors Kang et al., filed Dec. 27, 2006 and published Nov. 26, 2009, is directed to a cooling and heating cabinet device of a rear seat side for a vehicle using a thermoelectric module that is mounted between rear seats of a vehicle, having cooling and heating functions and further having an arm-resting function irrespective of its activation as the cooling and heating device, and that makes the exhaust fan activated by the control of the controller of the air conditioning system, thereby achieving the air-refreshing function as well as the cooling or heating mode function of the cooling and heating cabinet.

U.S. Pat. No. 8,191,187 for environmentally-conditioned topper member for beds by inventors Bykalski et al., filed Jul. 14, 2011 and issued Jun. 5, 2012, is directed to a conditioner mat for use with a bed assembly includes an upper layer comprising a plurality of openings, a lower layer being substantially fluid impermeable, at least one interior chamber defined by the upper layer and the lower layer and a spacer material positioned within the interior chamber. In one embodiment, the spacer material is configured to maintain a shape of the interior chamber and to help with the passage of fluids within a portion of interior chamber. The conditioner mat additionally includes an inlet in fluid communication with the interior chamber, at least one fluid module comprising a fluid transfer device and a conduit placing an outlet of the at least one fluid module in fluid communication with the inlet. In some arrangements, the fluid module selectively delivers fluids to the interior chamber through the conduit and the inlet. In one embodiment, fluids entering the chamber through the inlet are generally distributed within the chamber by the spacer material before exiting through the plurality of openings along the upper layer. The conditioner mat can be configured to releasably secure to a top of a bed assembly.

U.S. Pat. No. 8,418,285 for inflatable temperature control system by inventor Frias, filed May 23, 2010 and issued Apr. 16, 2013, is directed to an inflatable device having non-pressurized ducts and channels formed within the body of the inflatable device when inflated, wherein the inflation pressure of the inflatable device is maintained when the interior of the ducts and channels are exposed to atmospheric pressures allowing fluid to flow through the ducts and channels at substantially lower pressure levels than the inflation pressure of the inflatable device, a plurality of non-pressurized channels and pressurized support columns can be located in substantial proximity to the surface of the inflatable device in contact with the object to be heated or cooled.

US Publication No. 2013/0019611 for personal temperature control system by inventors Sims et al., filed Oct. 27, 2010 and published Jan. 24, 2013, is directed to a personal temperature control system includes an article having flexible tubing through it for circulating a heat transfer fluid and an article coupling affixed to distal ends of the flexible tubing. The article coupling releasably couples to a heat exchanger having a thermoelectric cooling/heating unit having one or more TEC plates, an aluminum heat sink, a fan and a controller in electrical communication with the TEC plates, a heat exchanger coupling adapted to releasably connect to the article coupling, an outlet line fluidly connecting the thermoelectric cooling/heating unit and the heat exchanger coupling, a return line fluidly connecting the thermoelectric cooling/heating unit and the heat exchanger coupling, a fluid reservoir in fluid communication with the outlet and return lines, the fluid reservoir forming a housing for the TEC plates, a pump in fluid communication with at least one of the outlet and return lines, and a power supply in electrical communication with the controller and the pump.

SUMMARY OF THE INVENTION

The present invention relates to an article comprising a temperature-conditioned surface, thermoelectric control unit, and method for temperature-conditioning the surface of an article.

In one embodiment, the present invention provides an article for temperature conditioning a surface, including a first layer having a plurality of openings, wherein the first layer has an exterior surface and an interior surface, a second layer having a corresponding plurality of openings, wherein the second layer has an exterior surface and an interior surface, and wherein the second layer is permanently affixed to the first layer along a periphery of the article and a periphery of the each of the plurality of openings, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, wherein the at least one interior chamber is constructed and configured to retain the fluid without leaking, and wherein the interior surface of the first layer and the interior surface of the second layer are formed of at least one layer of a waterproof material.

In another embodiment, the present invention provides a sleep system including at least one remote device and an article for adjusting a temperature of a surface, wherein the article further includes a first layer having a plurality of openings, wherein the first layer has an exterior surface and an interior surface, a second layer having a corresponding plurality of openings, wherein the second layer has an exterior surface and an interior surface, and wherein the second layer is permanently affixed to the first layer along a periphery of the article and a periphery of each of the plurality of openings, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote device and the at least one control unit have real-time or near-real-time two-way communication, wherein the at least one interior chamber is constructed and configured to retain the fluid without leaking, and wherein the interior surface of the first layer and the interior surface of the second layer are formed of at least one layer of a waterproof material.

In yet another embodiment, the present invention provides a sleep system including at least one body sensor, at least one remote device, at least one remote server, and an article for adjusting a temperature of a surface, wherein the article further includes a first layer having a plurality of openings, wherein the first layer has an exterior surface and an interior surface, a second layer having a corresponding plurality of openings, wherein the second layer has an exterior surface and an interior surface, and wherein the second layer is permanently affixed to the first layer along a periphery of the article and a periphery of each of the plurality of openings, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one body sensor and the at least one remote device have real-time or near-real-time two-way communication, wherein the at least one remote server and the at least one remote device have real-time or near-real-time two-way communication, wherein the at least one remote device and the at least one control unit have real-time or near-real-time two-way communication, wherein the at least one remote server is operable to determine optimized parameters for the article based on data from the at least one body sensor, wherein the at least one remote server is operable to transmit the optimized parameters for the article to the at least one remote device, wherein the at least one remote device is operable to transmit the optimized parameters for the article to the at least one control unit, wherein the at least one interior chamber is constructed and configured to retain the fluid without leaking, and wherein the interior surface of the first layer and the interior surface of the second layer are comprised of at least one layer of a waterproof material.

These and other aspects of the present invention will become apparent to those skilled in the art after a reading of the following description of the preferred embodiment when considered with the drawings, as they support the claimed invention.

DETAILED DESCRIPTION

Figure 1:
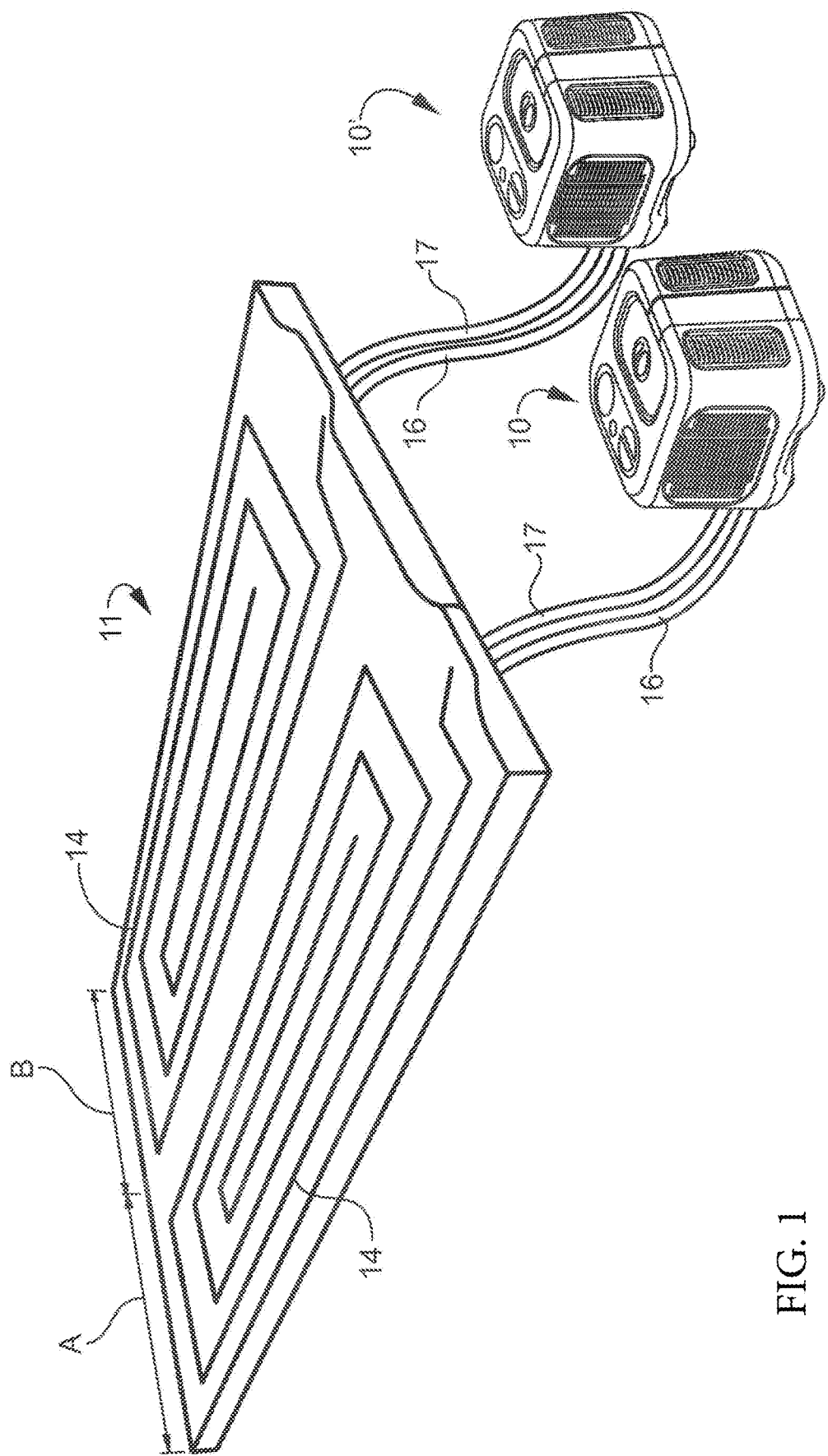
FIG. 1 is an environmental perspective view of a temperature-regulated mattress pad having two surface temperature zones connected to respective thermoelectric control units according to one exemplary embodiment of the present invention.

The present invention is generally directed to an article comprising a temperature-conditioned surface, thermoelectric control unit, and method for temperature-conditioning the surface of an article.

In one embodiment, the present invention provides an article for temperature conditioning a surface, including a first layer having a plurality of openings, wherein the first layer has an exterior surface and an interior surface, a second layer having a corresponding plurality of openings, wherein the second layer has an exterior surface and an interior surface, and wherein the second layer is permanently affixed to the first layer along a periphery of the article and a periphery of the each of the plurality of openings, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, wherein the at least one interior chamber is constructed and configured to retain the fluid without leaking, and wherein the interior surface of the first layer and the interior surface of the second layer are formed of at least one layer of a waterproof material.

In another embodiment, the present invention provides a sleep system including at least one remote device and an article for adjusting a temperature of a surface, wherein the article further includes a first layer having a plurality of openings, wherein the first layer has an exterior surface and an interior surface, a second layer having a corresponding plurality of openings, wherein the second layer has an exterior surface and an interior surface, and wherein the second layer is permanently affixed to the first layer along a periphery of the article and a periphery of each of the plurality of openings, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one remote device and the at least one control unit have real-time or near-real-time two-way communication, wherein the at least one interior chamber is constructed and configured to retain the fluid without leaking, and wherein the interior surface of the first layer and the interior surface of the second layer are formed of at least one layer of a waterproof material.

In yet another embodiment, the present invention provides a sleep system including at least one body sensor, at least one remote device, at least one remote server, and an article for adjusting a temperature of a surface, wherein the article further includes a first layer having a plurality of openings, wherein the first layer has an exterior surface and an interior surface, a second layer having a corresponding plurality of openings, wherein the second layer has an exterior surface and an interior surface, and wherein the second layer is permanently affixed to the first layer along a periphery of the article and a periphery of each of the plurality of openings, at least one interior chamber defined between the interior surface of the first layer and the interior surface of the second layer, at least one flexible fluid supply line for delivering a fluid to the at least one interior chamber, at least one flexible fluid return line for removing the fluid from the at least one interior chamber, and at least one control unit attached to the at least one flexible fluid supply line and the at least one flexible fluid return line, wherein the at least one control unit is operable to selectively cool or heat the fluid, and wherein the at least one control unit has at least one antenna and at least one processor, wherein the at least one body sensor and the at least one remote device have real-time or near-real-time two-way communication, wherein the at least one remote server and the at least one remote device have real-time or near-real-time two-way communication, wherein the at least one remote device and the at least one control unit have real-time or near-real-time two-way communication, wherein the at least one remote server is operable to determine optimized parameters for the article based on data from the at least one body sensor, wherein the at least one remote server is operable to transmit the optimized parameters for the article to the at least one remote device, wherein the at least one remote device is operable to transmit the optimized parameters for the article to the at least one control unit, wherein the at least one interior chamber is constructed and configured to retain the fluid without leaking, and wherein the interior surface of the first layer and the interior surface of the second layer are comprised of at least one layer of a waterproof material.

None of the prior art discloses an article for adjusting the temperature of a surface formed from a first layer having a plurality of openings and a second layer having a corresponding plurality of openings, wherein the second layer is permanently affixed to the first layer along a periphery of the article and a periphery of each of the plurality of openings, and wherein at least one interior chamber constructed and configured to retain a fluid without leaking is defined between an interior surface of the first layer and an interior surface of the second layer. Further, none of the prior art discloses using such an article in a sleep system to programmatically control target temperatures over time, such as over the course of a night's sleep, using at least one remote device. Finally, none of the prior art discloses using such an article in a sleep system with at least one body sensor, wherein optimized parameters for the article are based on data from the at least one body sensor.

Referring now to the drawings in general, the illustrations are for the purpose of describing a preferred embodiment of the invention and are not intended to limit the invention thereto.

Figure 2:
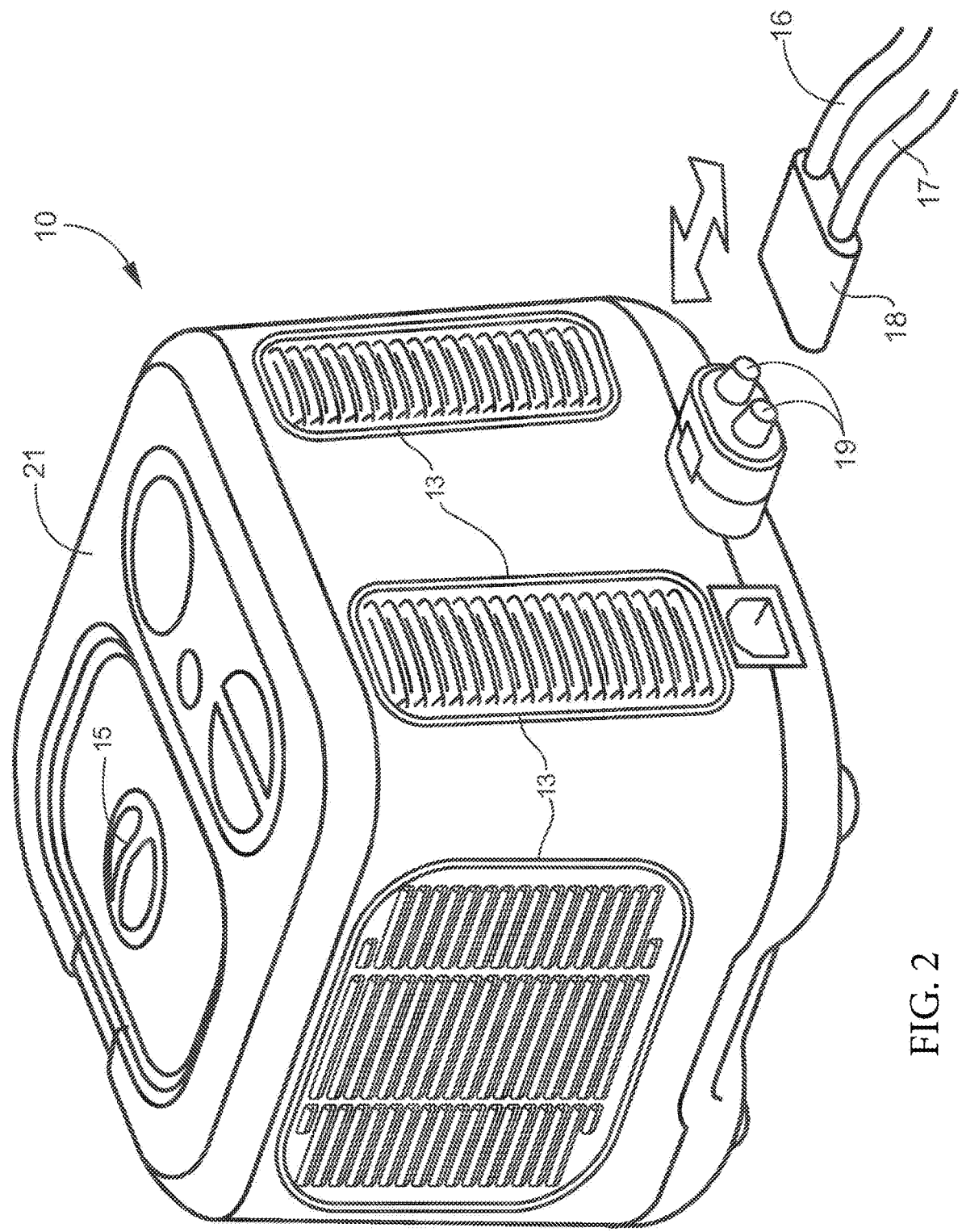
FIG. 2 is a perspective view of the exemplary control unit demonstrating the quick connection/disconnection of the flexible fluid supply and return lines.

Referring now specifically to the drawings of exemplary embodiments and implementations of the present invention, a thermoelectric control unit according to the present invention is illustrated in FIG. 1, and shown generally referenced by numeral 10. As shown, a pair of identical control units 10, 10' attach through flexible conduit to a temperature-conditioned article, such as mattress pad 11. The mattress pad 11 has two independent thermally regulated surface zones "A" and "B", each containing internal flexible (e.g., silicon) tubing 14 designed for circulating heated or cooled fluid within a hydraulic circuit between the control unit 10 and the mattress pad 11. As best shown in FIGS. 1 and 2, the flexible conduit assembly for each control unit 10 includes separate fluid supply and return lines 16, 17 connected to tubing 14, and a quick-release female connector 18 for ready attachment and detachment to external male connectors 19 of the control unit 10. Advantageously, the mattress pad 11 allows a user to retrofit an existing mattress.

In one embodiment, the thermoelectric control unit 10 is operatively connected (e.g., by flexible conduit) to a mattress, such that the temperature-conditioned surface is embedded in the mattress itself. In alternative exemplary embodiments, the thermoelectric control unit 10 is operatively connected (e.g., by flexible conduit) to any other temperature regulated article, such as a blanket or other bedding or covers, seat pad, sofa, chair, or the like.

Figure 3:
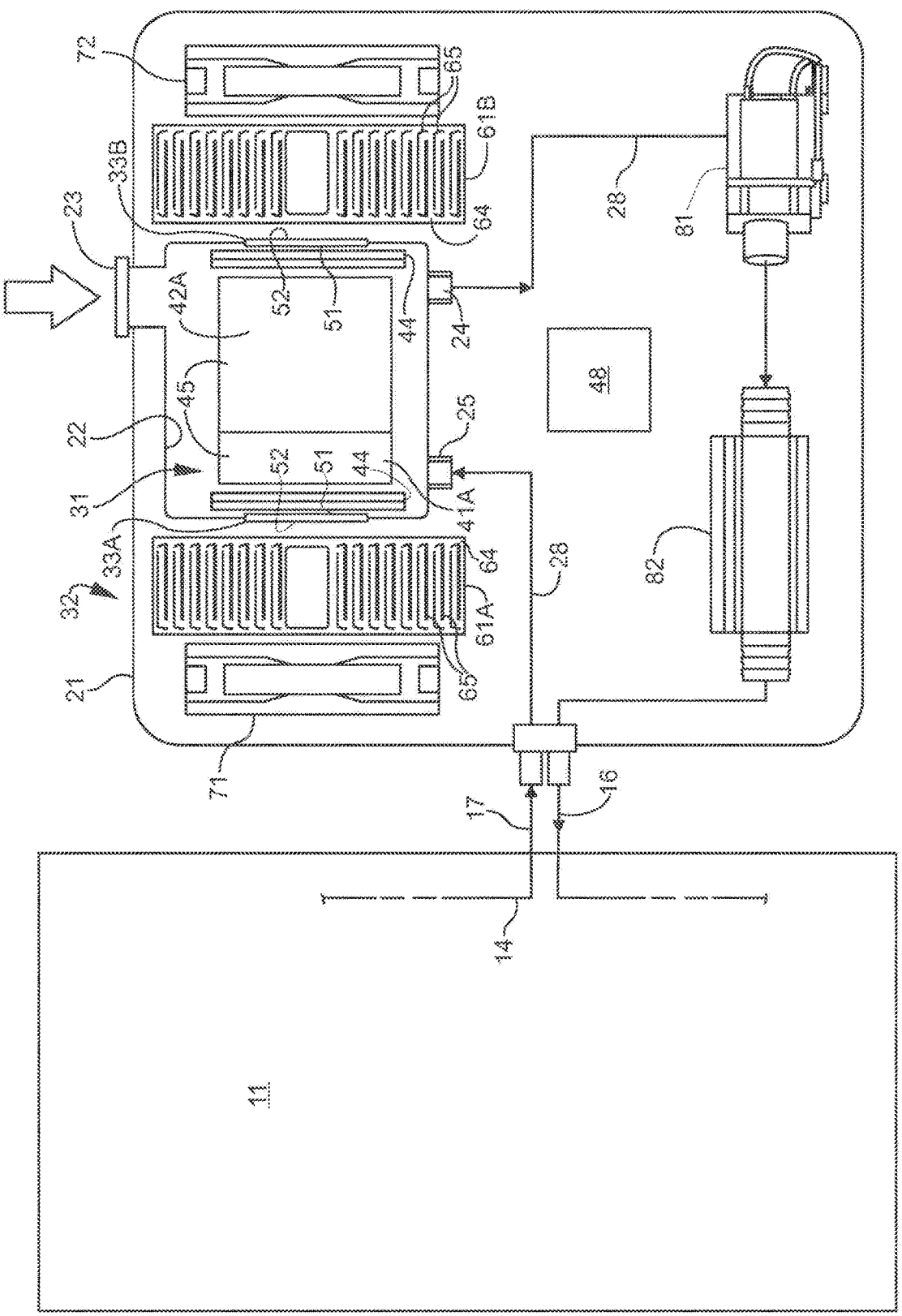
FIG. 3 is a side schematic view showing various internal components of the exemplary control unit fluidly connected to the mattress pad.
Figure 4:
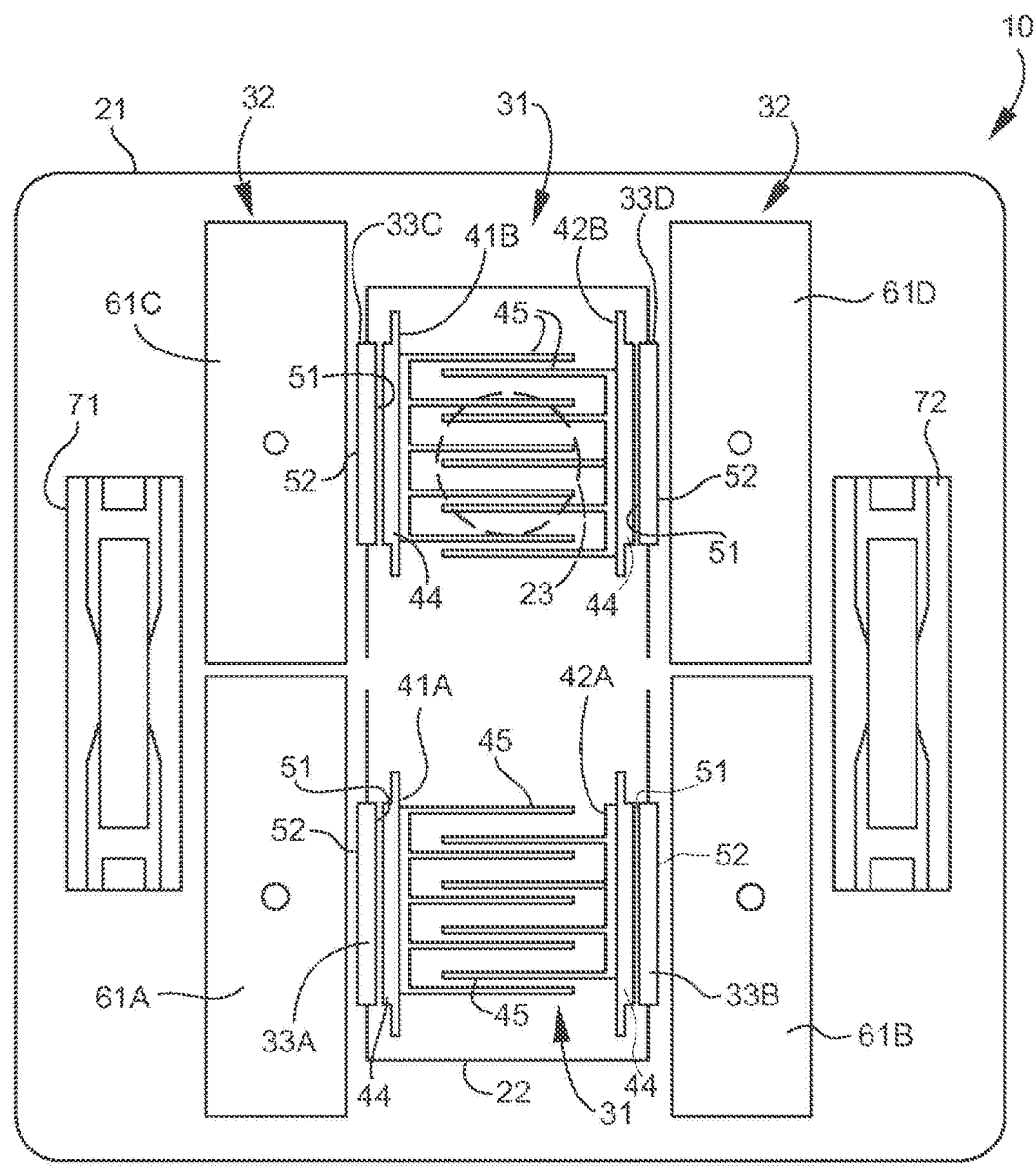
FIG. 4 is a top schematic view of the exemplary control unit.

As illustrated in FIGS. 3 and 4, the exemplary control unit 10 has an external housing 21, and a fluid reservoir 22 located inside the housing 21. The reservoir 22 has a fill opening 23 accessible through a removably capped opening 15 (FIG. 2) in housing 21, a fluid outlet 24, and a fluid return 25. Fluid contained in the reservoir 22 is moved in a circuit through a conduit assembly formed from in-housing tubes 28, the flexible supply and return lines 16, 17, and flexible silicone tubing 14 within the temperature-regulated pad 11. The fluid is selectively cooled, as described further below, by cooperating first and second heat exchangers 31, 32 and thermoelectric cooling modules 33A-33D. The cooling modules 33A-33D reside at an electrified junction between the first and second heat exchangers 31, 32, and function to regulate fluid temperature from a cool point of as low as 7.78° C. (46° F.), or cooler. The housing 21 and reservoir 22 may be either separately or integrally constructed of any suitable material, such as an anti-flammable ABS, polypropylene, or other molded polymer.

Referring to FIGS. 3 and 4, the first heat exchanger 31 is formed of pairs of oppositely directed internal heat sinks 41A, 42A and 41B, 42B communicating with an inside of the reservoir 22, and cooperating with thermoelectric cooling modules 33A-33D to cool the fluid inside the reservoir 22 to a selected (set) temperature. Each heat sink 41A, 42A, 41B, 42B has a substantially planar metal base 44 adjacent an exterior side wall of the reservoir 22, and a plurality of planar metal fins 45 extending substantially perpendicular to the base 44 and vertically inward towards a center region of the reservoir 22. In the exemplary embodiment, each pair of heat sinks 41A, 42A and 41B, 42B is formed from one 4-fin sink and one 5-fin sink arranged such that their respective fins 45 are facing and interleaved as shown in FIG. 4. The exemplary cooling modules 33A-33D are operatively connected to an internal power supply/main control board 48, and are formed from respective thin Peltier chips having opposing planar inside and outside major surfaces 51, 52.

The inside major surface 51 of each cooling module 33A-33D resides in direct thermal contact with the planar base 44 of its corresponding heat sink 41A, 42A, 41B, 42B. A thermal pad or compound (not shown) may also reside between each cooling module 33A-33D and heat sink 41A, 42A, 41B, 42B to promote thermal conduction from base 44 outwardly across the fins 45.

The second heat exchanger 32 is formed from external heat sinks 61A-61D located outside of the fluid reservoir 22, and arranged in an opposite-facing direction to respective internal heat sinks 41A, 42A, 41B, 42B. Each external heat sink 61A-61D has a planar metal base 64 in direct thermal contact with the outside major surface 52 of an associated adjacent cooling module 33A-33D, and a plurality of planar metal fins 65 extending substantially perpendicular to the base 64 and horizontally outward away from the fluid reservoir 22. Heat generated by the cooling modules 33A-33D is conducted by the external heat sinks 61A-61D away from the modules 33A-33D and dissipated to a surrounding environment outside of the fluid reservoir 22. Electric case fans 71 and 72 may be operatively connected to the power supply/main control board 48 and mounted inside the housing 21 adjacent respective heat sinks 61A, 61B and 61C, 61D. The exemplary fans 71, 72 promote air flow across the sink fins 65, and outwardly from the control unit 10 through exhaust vents 13 formed with the sides and bottom of the housing 21. In one embodiment, each external heat sink 61A-61D has a substantially larger base 64 (as compared to the 4-fin and 5-fin internal sinks 41A, 42A, 41B, 42B) and a substantially greater number of fins 65 (e.g., 32 or more). Both internal and external heat sinks may be active or passive, and may be constructed of any suitable conductive material, including aluminum, copper, and other metals. The heat sinks may have a thermal conductivity of 400 watts per meter-Kelvin (W/(m·K)), or more. The case fans 71, 72 may automatically activate and shut off as needed.

From the reservoir 22, the temperature conditioned fluid exits through the outlet 24 and enters the conduit assembly formed from an arrangement of in-housing Z-, L-, 7-, and S-shaped tubes 28 (and joints). A pump 81 is operatively connected to the reservoir 22 and functions to circulate the fluid through the control unit 10 in a circuit including the in-housing tubes 28 (and joints), flexible fluid supply line 16, silicone pad tubes 14, fluid return line 17, and back into the reservoir 22 through fluid return 25. As shown in FIG. 3, an insulated linear heat tube 82 is located outside of the fluid reservoir 22 and inside the housing 21, and communicates with the conduit assembly to selectively heat fluid moving from the control unit 10 to the mattress pad 11. The exemplary heat tube 82 may heat fluid moving in the hydraulic circuit to a desired temperature of as warm as 47.78° C. (118° F.).

The control unit 10 has at least one fluid reservoir. In one embodiment, the control unit 10 includes two fluid reservoirs. A first fluid reservoir is used to heat and/or cool fluid that circulates through the temperature-regulated pad 11. The first fluid reservoir includes at least one sensor to measure a level of the fluid. A second fluid reservoir is used to store fluid. In a preferred embodiment, fluid from the second fluid reservoir is automatically used to fill the first fluid reservoir when the at least one sensor indicates that the level of the fluid is below a minimum value. Advantageously, this optimizes the temperature in the first fluid reservoir because only a small amount of stored fluid is introduced into the first fluid reservoir when needed. Additionally, this embodiment reduces the refilling required for the control unit 10, saving the user time and effort. In one embodiment, the at least one fluid reservoir is formed of metal. In another embodiment, the metal of the at least one fluid reservoir is electrically connected to ground.

Figure 5:
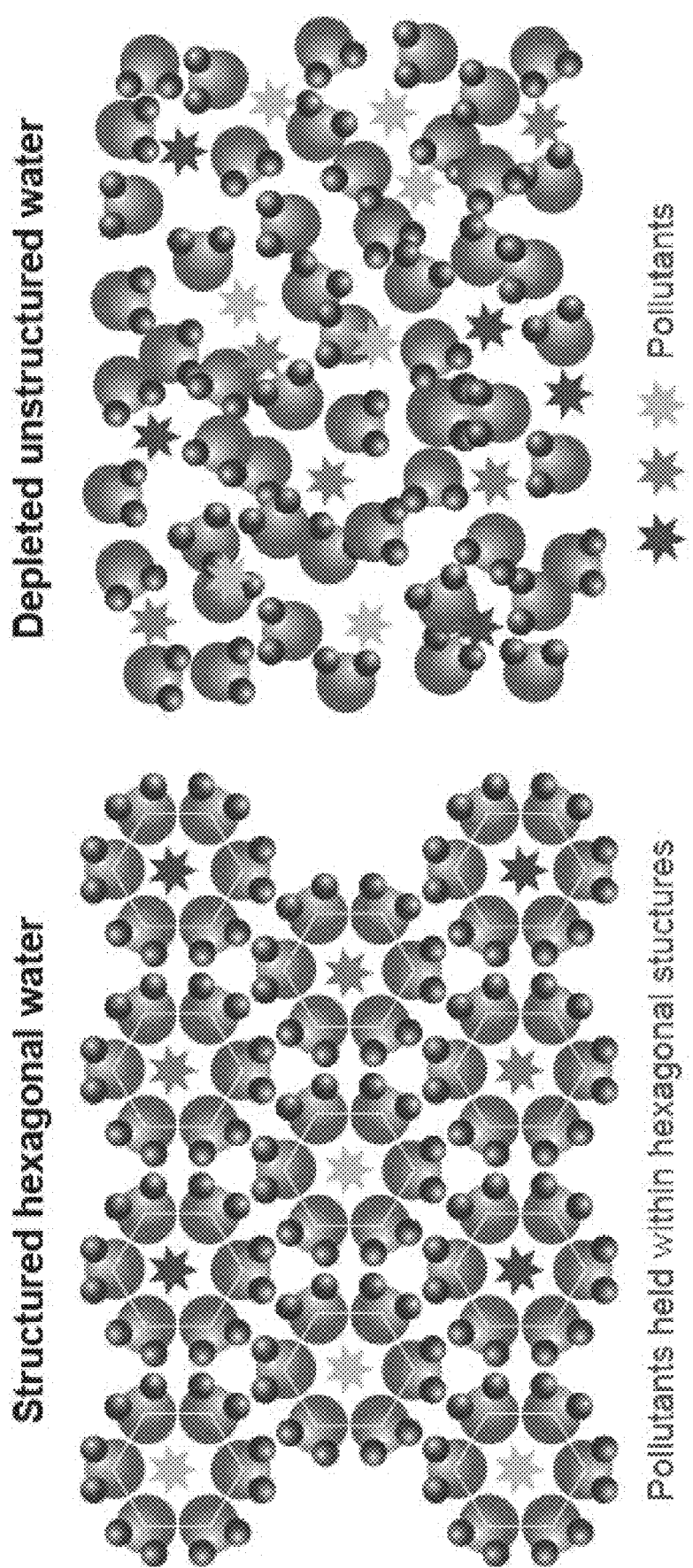
FIG. 5 illustrates the difference between structured water and unstructured water.

In a preferred embodiment, the control unit 10 includes at least one mechanism for forming structured water. FIG. 5 illustrates the difference between structured water and unstructured water. In one embodiment, the control unit includes at least one vortex to treat the fluid. The at least one vortex reduces bacteria, algae, and fungus in the fluid without using additional chemicals. In one embodiment, the at least one vortex includes at least one left spin vortex and at least one right spin vortex. The at least one left spin vortex and the at least one right spin vortex mimics the movement of water in nature. One example of utilizing vortex technologies to treat fluids is described in U.S. Pat. No. 7,238,289, which is incorporated by reference herein in its entirety. Alternatively, the fluid can flow or tumble over or through a series of balls and/or rocks. In one embodiment, the rocks are in a hexagonal shape. A tumbling action or vortex aligns the molecules in the structured water to retain energy (i.e., cooling or heating) for a longer period of time. Surprisingly, the aligned or structured water molecules produced a 20% increase in the heating and cooling capacity of the water.

In a preferred embodiment, the fluid is water. In one embodiment, the water is treated with a UV purification system to kill microorganisms (e.g., bacteria, viruses, molds). The UV purification system includes at least one UV light bulb to expose microorganisms to UV radiation, which prevents the microorganisms from reproducing. This reduces the number of microorganisms in the water without using additional chemicals. In one embodiment, the at least one UV light bulb is a UV-C light emitting diode (LED). In another embodiment, the at least one UV light bulb is a mercury vapor bulb.

Additionally or alternatively, the water is treated with at least one filter to remove contaminants and/or particles. In a preferred embodiment, the at least one filter clarifies the water before exposure to the at least one UV light bulb. Contaminants and/or particles in the water are larger than the microorganisms, so contaminants and/or particles block the UV rays from reaching the microorganisms. In one embodiment, the at least one filter is a sediment filter, an activated carbon filter, a reverse osmosis filter, and/or a ceramic filter. In another embodiment, one or more of the at least one filter includes copper and/or silver (e.g., nanoparticles, ions, colloidal) to suppress the growth of microorganisms. Contaminants and/or particles that are removed from the water include sediment, rust, calcium carbonate, organic compounds, chlorine, and/or minerals.

The at least one filter preferably removes contaminants and/or particles with a diameter greater than 0.3 µm. Alternatively, the at least one filter removes contaminants and/or particles with a diameter greater than 0.5 µm. In another embodiment, the at least one filter removes contaminants and/or particles with a diameter greater than 0.05 µm. In another embodiment, the at least one filter removes contaminants and/or particles with a diameter greater than 1 nm.

In one embodiment, the water is treated with copper and/or silver ions. The copper and/or silver ions are positively charged and bond with negative sites on cell walls of microorganisms. This can lead to the deactivation of proteins and ultimately to cell death. Copper and/or silver ions can also destroy biofilms and slimes. In one embodiment, the copper and/or silver ions are created through electrolysis.

Alternatively, the water is treated with at least one chemical to inhibit growth of bacteria and microorganisms or to remove lime and calcium buildup. In one embodiment, the water is treated with a compound containing iodine or chlorine. In another embodiment, the water is treated with salt and/or a peroxide solution. In yet another embodiment, the water is treated with citric acid.

The thermoelectric control unit 10 may further include other features and electronics not shown including a touch control and display board, overheat protectors, fluid level sensor, thermostat, additional case fans, and other such components. The control unit 10 may also include an external power cord designed to plug into standard household electrical outlets, or may be powered using rechargeable or non-rechargeable batteries. In one embodiment, the touch control and display board includes a power button, temperature selection buttons (e.g., up arrow and down arrow), and/or an LCD to display the temperature. In another embodiment, the touch control and display board includes a program selection menu.

The control unit 10 preferably has at least one processor. By way of example, and not limitation, the processor may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information. In one embodiment, one or more of the at least one processor is operable to run predefined programs stored in at least one memory of the control unit 10.

The control unit 10 preferably includes at least one antenna, which allows the control unit 10 to receive and process input data (e.g., temperature settings, start and stop commands) from at least one remote device (e.g., smartphone, tablet, laptop computer, desktop computer, remote control). In a preferred embodiment, the at least one remote device is in wireless network communication with the control unit. The wireless communication is, by way of example and not limitation, radiofrequency, Bluetooth, ZigBee, Wi-Fi, wireless local area networking, near field communication (NFC), or other similar commercially utilized standards. Alternatively, the at least one remote device is in wired communication with the control unit through USB or equivalent.

In a preferred embodiment, the at least one remote device is operable to set target temperatures for the mattress pad. The at least one remote device preferably has a user interface (e.g., a mobile application for a smartphone or tablet, buttons on a remote control) that allows a user to select target temperatures for the mattress pad or independent zones within the mattress pad. In one embodiment, the mattress pad includes temperature probes in each zone that provide temperature data for that zone to the at least one processor, which compares a target temperature set using the at least one device to an actual measured temperature to determine whether to heat or cool the fluid and determine where to distribute the heated or cooled fluid in order to make the actual temperature match the target temperature.

Those skilled in the art will recognize that programmatic control of the target temperatures over time, such as over the course of a night's sleep, is possible using the at least one remote device. Because the target temperatures can be set at any time, those target temperatures can be manipulated through the sleeping period in order to match user preferences or a program to correlate with user sleep cycles to produce a deeper, more restful sleep.

Figure 6A:
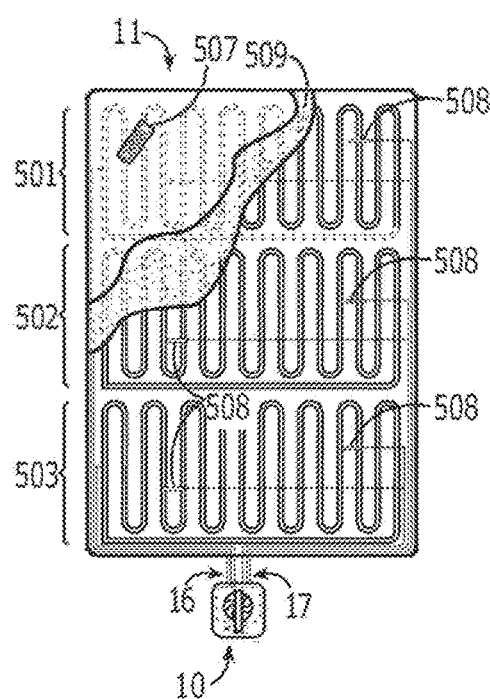
FIG. 6A illustrates one embodiment of a mattress pad with three independent temperature zones.

FIG. 6A illustrates one embodiment of a mattress pad with three independent temperature zones. The three independent temperature zones 501, 502, 503 generally correspond to the head, body and legs, and feet, respectfully, of a user. Although only three zones are shown, it is equally possible to have one, two, four, or more independent temperature zones. A wireless remote control 507 is used to set the target temperatures for each of the zones 501, 502, 503. Temperature probes 508 in each zone provide actual measured temperature data for that zone to the control unit 10. The control unit 10 compares the target temperature set using the wireless remote control 507 and the actual measured temperature to determine whether to heat or cool the fluid and determine to which conduit or circuits the heated or cooled fluid should be distributed in order to make the actual temperature match the target temperature.

In one embodiment, a larger number of temperature probes are in the independent temperature zones corresponding to the core body region, and a smaller number of temperature probes are in the independent temperature zones not corresponding to the core body region. In one example, zone 501 contains three temperature probes, zone 502 contains five temperature probes, and zone 503 contains three temperature probes. This embodiment provides the advantage of more closely monitoring the temperature of the pad in the core body region, which is important because core body temperature impacts how well a user sleeps.

In another embodiment, an independent temperature zone contains three temperature probes. In one example, zone 501 contains a temperature probe in the center of the mattress pad 11, a temperature probe on the left side of the mattress pad 11, and a temperature probe on the right side of the mattress pad 11. Advantageously, this embodiment provides information about the left, center, and right of the mattress pad. In yet another embodiment, an independent temperature zone contains at least three temperature probes.

The mattress pad includes padding 509 between the conduit circuits and the resting surface, in order to improve the comfort of a user and to prevent the concentrated heat or cold of the conduit circuits from being applied directly or semi-directly to the user's body. Instead, the conduit circuits heat or cool the padding 509, which provides more gentle temperature modulation for the user's body.

Figure 6B:
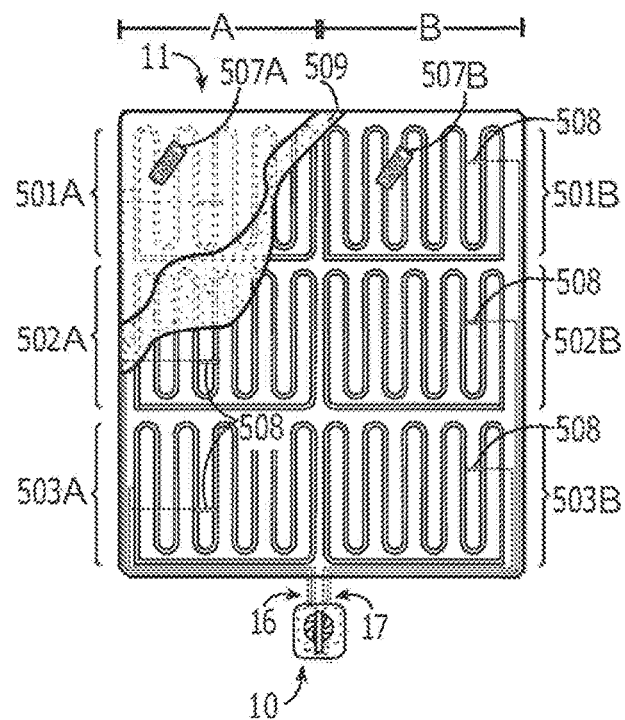
FIG. 6B illustrates one embodiment of a double mattress pad with three independent temperature zones for both users.

FIG. 6B illustrates one embodiment of a double mattress pad. Three independent temperature zones 501A, 502A, 503A generally correspond to the head, body and legs, and feet, respectfully, of a first user who utilizes surface zone "A". Three independent temperature zones 501B, 502B, 503B generally correspond to the head, body and legs, and feet, respectfully, of a second user who utilizes surface zone "B". Although only three zones are shown for each user, it is equally possible to have one, two, four, or more independent temperature zones. A first wireless remote control 507A is used to set the target temperatures for each of the zones 501A, 502A, 503A. A second wireless remote control 507B is used to set the target temperatures for each of the zones 501B, 502B, 503B. Temperature probes 508 in each zone provide actual measured temperature data for that zone to the control unit 10. The control unit 10 compares the target temperature set using the wireless remote control 507A, 507B and the actual measured temperature to determine whether to heat or cool the fluid and determine to which conduit or circuits the heated or cooled fluid should be distributed in order to make the actual temperature match the target temperature.

In this embodiment, despite the presence of two separate controls, a single control unit 10 is utilized to control the temperature of the fluid. In another embodiment, a first control unit is utilized to control the temperature of the fluid for the first user and a second control unit is utilized to control the temperature of the fluid for the second user. Alternatively, each user has at least two control units to control the temperature of the fluid.

Figure 6C:
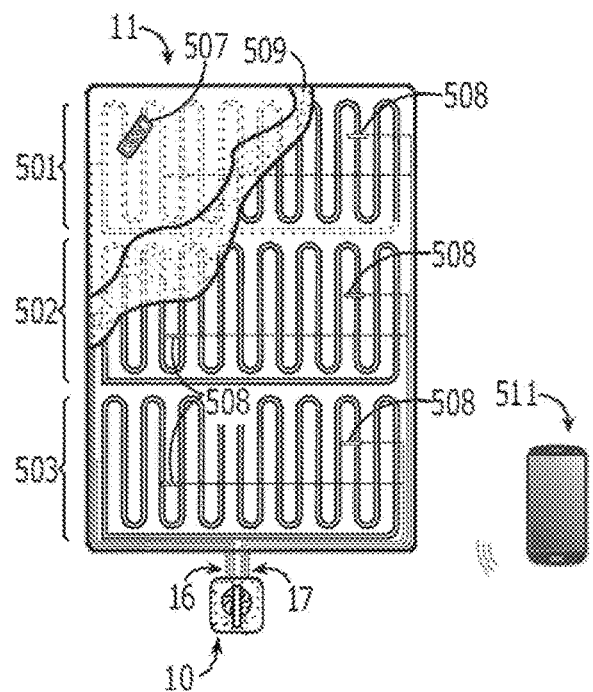
FIG. 6C illustrates one embodiment of a mattress pad with three independent temperature zones connected to at least one remote device.

FIG. 6C illustrates one embodiment of a mattress pad with three independent temperature zones connected to at least one remote device 511. In a preferred embodiment, the at least one remote device is a smartphone or a tablet. The at least one remote device preferably has a mobile application that allows for the control unit 10 to vary the temperature of the mattress pad 11 according to a schedule of target temperatures selected to correlate with sleep cycles of the user. Such an arrangement promotes deeper, more restful sleep by altering body temperature at critical points.

Preferably, the mattress pad 11 is sized to fit standard mattress sizes. For example, twin (about 97 cm by about 191 cm (about 38 inches by about 75 inches)), twin XL (about 97 cm by about 203 cm (about 38 inches by about 80 inches)), full (about 137 cm by about 191 cm (about 54 inches by about 75 inches)), queen (about 152 cm by about 203 cm (about 60 inches by about 80 inches)), king (about 193 cm by about 203 cm (about 76 inches by about 80 inches), and California king (about 183 cm by about 213 cm (about 72 inches by about 84 inches)). In one embodiment, the mattress pad is about 76 cm by about 203 cm (about 30 inches by about 80 inches). This allows a single user of a full, queen, or king size bed to use the mattress pad without affecting a sleeping partner. In one embodiment, the mattress pad is sized to fit a crib mattress (about 71 cm by about 132 cm (about 28 inches by about 52 inches)). In a preferred embodiment, the single mattress pad (e.g., twin, twin XL, sized to fit a single user of a larger bed, crib) attaches to one control unit and the double mattress pad (e.g., full, queen, king, California king) attaches to two control units.

In an alternative embodiment, the mattress pad contains a conductive fiber to heat one section of the mattress pad and water circulation to cool another section of the mattress pad. In one example, this allows the temperature of the main body or body core region to be lower than the temperature for the feet. The feet play an active role in the regulation of body temperature. The feet have a large surface area and specialized blood vessels, which allow the feet to release heat from the body. If the feet become too cold, excess heat cannot be released from the body and an individual will not be able to sleep.

In one embodiment, the mattress pad is grounded, which provides the human body with electrically conductive contact with the surface of the earth. Grounding is based on the theory that the earth is a source of negatively charged free electrons, and, when in contact with the earth, the body can use these free electrons as antioxidants to neutralize free radicals within the body. Grounding the body during sleep can normalize cortisol levels, improve sleep, and decrease pain and stress levels. In a preferred embodiment, the mattress pad has a conductive material on at least one exterior surface of the mattress pad. In one embodiment, the mattress pad is attached to a wire that is electrically connected to an electrical outlet ground port. Alternatively, the mattress pad is attached to a wire that is connected to a ground rod.

The mattress pad includes at least two layers of a waterproof material that are laminated, affixed to each other, adhered to each other, attached to each other, secured to each other, or welded together to prevent separation or delamination of the layers. In a preferred embodiment, the waterproof material is a urethane or a mixture of urethane and ethylene-vinyl acetate (EVA). A first layer of the waterproof material is permanently affixed to a second layer of the waterproof material. The first layer of the waterproof material has an exterior surface and an interior surface. The second layer of the waterproof material has an exterior surface and an interior surface. In a preferred embodiment, the first layer of the waterproof material is welded (e.g., using high frequency/radio frequency (RF) welding or heat welding) to the second layer of the waterproof material along a continuous perimeter, creating at least one interior chamber constructed and configured to retain fluid without leaking between the interior surface of the first layer of the waterproof material and the interior surface of the second layer of the waterproof material. Fluid is delivered to the at least one interior chamber via a fluid supply line 16 that enters the continuous perimeter via an opening sized to sealingly receive the fluid supply line 16. Fluid is removed from the at least one interior chamber via a fluid return line 17 that exits the continuous perimeter via an opening sized to sealingly receive the fluid return line 17.

In a preferred embodiment, the waterproof material is covered on the exterior surfaces with an interlock or knit fabric. The interlock or knit fabric on the exterior surface of the mattress pad preferably contains a copper or a silver ion thread for antimicrobial protection. Alternatively, the interlock or knit fabric on the exterior surface of the mattress pad is treated with an antibacterial or an antimicrobial agent (e.g., Microban®). In one embodiment, the waterproof material is covered on the exterior surface with a moisture wicking material.

In one embodiment, the mattress pad includes a spacer layer positioned within the interior chamber between the interior surface of the first layer of the waterproof material and the interior surface of the second layer of the waterproof material. The spacer layer provides separation between the first layer of the waterproof material and the second layer of the waterproof material, ensuring that the fluid flows through the mattress pad when a body is on the mattress pad. The spacer layer advantageously provides structural support to maintain partial channels through the interior chamber or fluid passageways, which are important to ensure constant and consistent fluid flow through the interior chamber with heavy users on firm mattresses. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties.

Figure 7B:
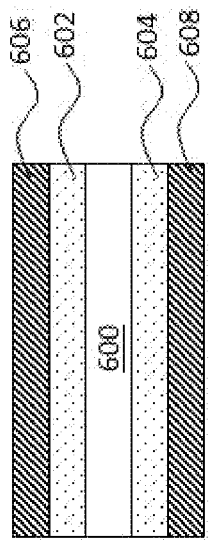
FIG. 7B illustrates a cross-section of a mattress pad with two layers of waterproof material and two layers of a second material.
Figure 7D:
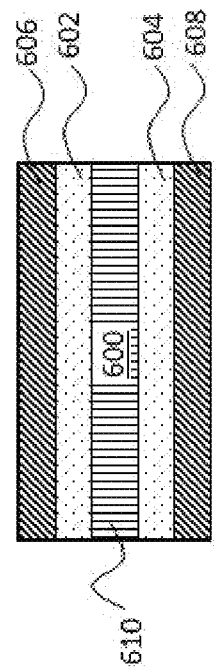
FIG. 7D illustrates a cross-section of a mattress pad with two layers of waterproof material, two layers of a second material, and a spacer layer.
Figure 7A:
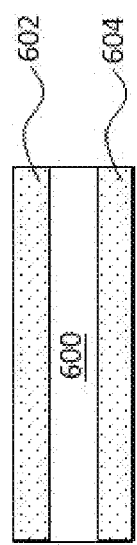
FIG. 7A illustrates a cross-section of a mattress pad with two layers of waterproof material.

FIG. 7A illustrates a cross-section of a mattress pad with two layers of waterproof material. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding).

FIG. 7B illustrates a cross-section of a mattress pad with two layers of waterproof material and two layers of a second material. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding). A first layer of a second material 606 is on an exterior surface of the first layer of the waterproof material 602. A second layer of the second material 608 is on an exterior surface of the second layer of the waterproof material 604. In a preferred embodiment, the second material is a knit or interlock material. Alternatively, the second material is a woven or non-woven material. In yet another embodiment, the second material is formed of plastic.

Figure 7C:
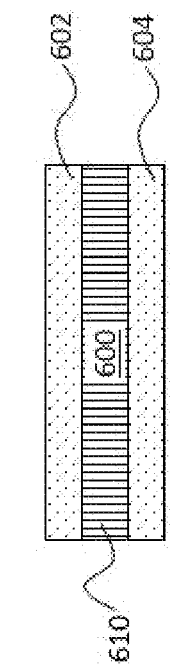
FIG. 7C illustrates a cross-section of a mattress pad with two layers of waterproof material and a spacer layer.

FIG. 7C illustrates a cross-section of a mattress pad with two layers of waterproof material and a spacer layer. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding).

A spacer layer 610 is positioned within the interior chamber 600 between an interior surface of the first layer of the waterproof material 602 and an interior facing of the second layer of the waterproof material 604. The spacer layer 610 is configured to provide structural support to maintain partial channels for fluid flow through the interior chamber. In one embodiment, the fluid flows through the spacer layer. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties. In another embodiment, the spacer layer 610 is in a honeycomb shape.

FIG. 7D illustrates a cross-section of a mattress pad with two layers of waterproof material, two layers of a second material, and a spacer layer. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding). A first layer of a second material 606 is on an exterior surface of the first layer of the waterproof material 602. A second layer of the second material 608 is on an exterior surface of the second layer of the waterproof material 604. In a preferred embodiment, the second material is a knit or interlock material. Alternatively, the second material is a woven or non-woven material. In yet another embodiment, the second material is formed of plastic.

A spacer layer 610 is positioned within the interior chamber 600 between an interior surface of the first layer of the waterproof material 602 and an interior facing of the second layer of the waterproof material 604. The spacer layer 610 is configured to provide structural support to maintain partial channels for fluid flow through the interior chamber. In one embodiment, the fluid flows through the spacer layer. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties.

Figure 8:
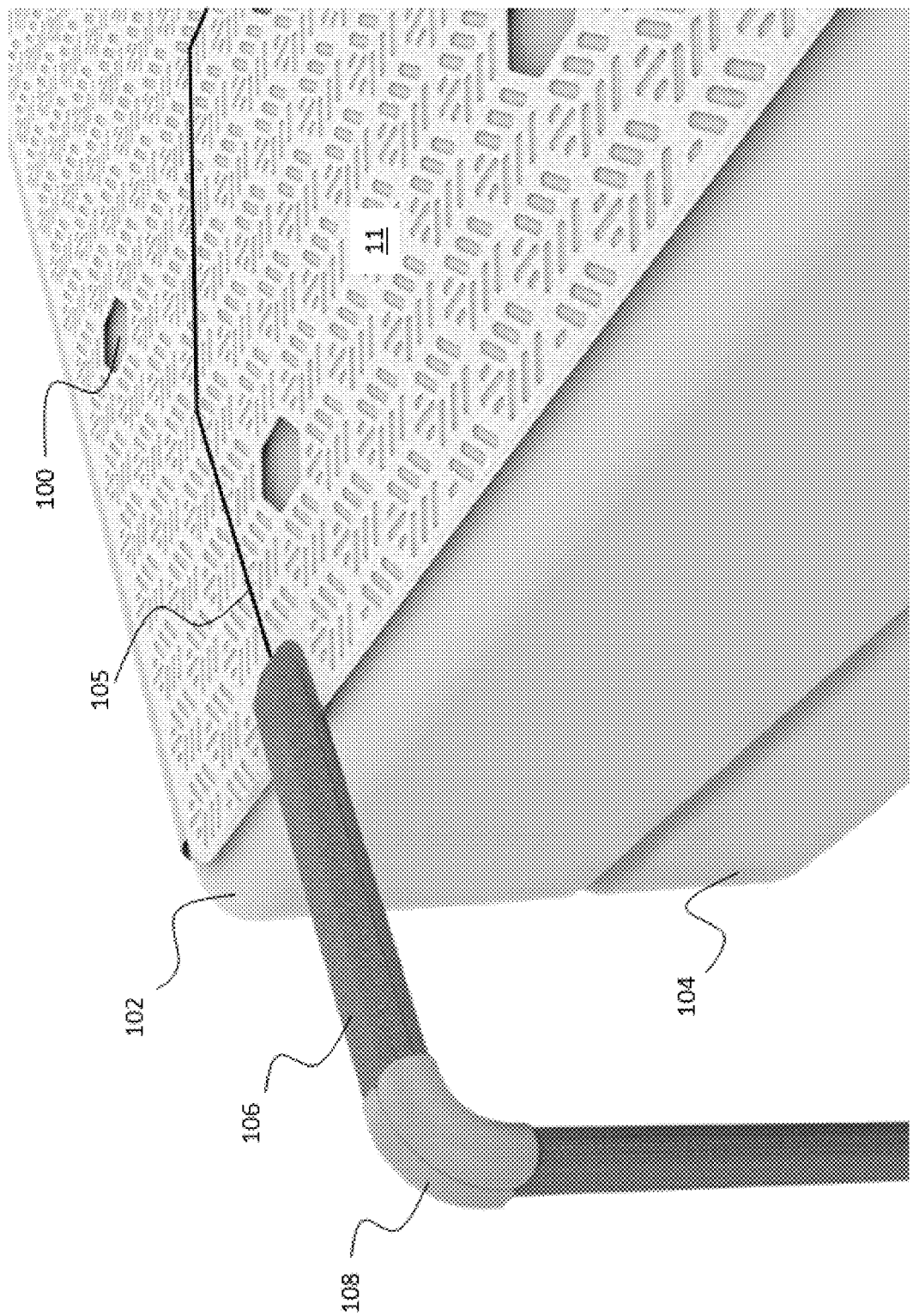
FIG. 8 is a view of a mattress pad hose elbow according to one embodiment.

FIG. 8 is a view of a mattress pad hose elbow according to a preferred embodiment. The mattress pad 11 is placed on top of a mattress 102 and box springs or foundation 104. The mattress pad 11 connects to the control unit 10 (not shown) via a flexible hose 106 containing the flexible supply and return lines 16, 17. The flexible hose is preferably formed from a polyurethane. Alternatively, the flexible hose is formed from extruded silicone double wall tubing. In one embodiment, the flexible hose has a polyethylene foam or other insulating cover. Additionally or alternatively, the flexible hose is covered with a fabric (e.g., nylon, polyester, rayon).

A mattress pad hose elbow 108 is concentric around the flexible hose 106. The mattress pad hose elbow 108 secures the flexible hose 106 to the side of the mattress 102 and box springs or foundation 104, which provides structural support to the flexible hose 106. The mattress pad hose elbow 108 is sized to fit tightly around the flexible hose 106. In a preferred embodiment, the mattress pad hose elbow 108 is formed with silicone or rubber. Alternatively, the mattress pad hose elbow 108 is formed from plastic (e.g., ethylene-vinyl acetate (EVA) foam, polyethylene foam). In a preferred embodiment, the mattress pad hose elbow 108 is operable to slide on the flexible hose 106. In one embodiment, the mattress pad hose elbow 108 is adjustable.

The mattress pad 11 preferably contains a plurality of holes or openings 100 in the surface of the mattress pad 11. The plurality of holes or openings 100 direct the movement of the fluid in the pad. In a preferred embodiment, the plurality of holes or openings 100 is in a pre-selected pattern to help manufacturing efficiency. Alternatively, the plurality of holes or openings 100 is in a random pattern. The plurality of holes or openings 100 is shown in a hexagon shape in FIG. 7. Alternatively, the shape of each of the plurality of holes or openings 100 can be in the shape of a triangle, a circle, a rectangle, a square, an oval, a diamond, a pentagon, a heptagon, an octagon, a nonagon, a decagon, a trapezium, a parallelogram, a rhombus, a cross, a semicircle, a crescent, a heart, a star, a snowflake, or any other polygon. In one embodiment, the voids created by the plurality of holes or openings 100 include at least 80% of the surface area of the mattress pad. In other embodiments, the voids created by the plurality of holes or openings 100 include at least 5%, at least 10%, at least 15%, at least 20%, at least 25%, at least 30%, at least 40%, at least 50%, at least 60%, at least 70%, at least 75%, at least 85%, at least 90%, or at least 95% of the surface area of the mattress pad.

The spacing and number of the plurality of holes or openings 100 can be varied to adjust the thermal properties of the mattress pad. For example, in one embodiment, the density of the holes or openings is higher near the torso region than in the head and leg regions, for providing more exposure to the torso region of the user for managing body temperature in that region, and less exposure to the extremities of the user. In one embodiment, the spacing between each of the plurality of holes or openings is at least 5 mm (0.2 inches).

In a preferred embodiment, the mattress pad 11 contains at least one weld line 105 to help manage the flow of the fluid in the interior chamber. The at least one weld line 105 preferably directs the fluid flow through the pad from head to foot, and returns the fluid to the control unit via the return line. The at least one weld line 105 allows the fluid to flow across all areas of the mattress pad 11 to provide a substantially uniform temperature within the pad. In one embodiment, the at least one weld line is formed from the permanent attachment of the first layer of the waterproof material and the second layer of the waterproof layer along the periphery of the plurality of holes or openings.

Figure 9:
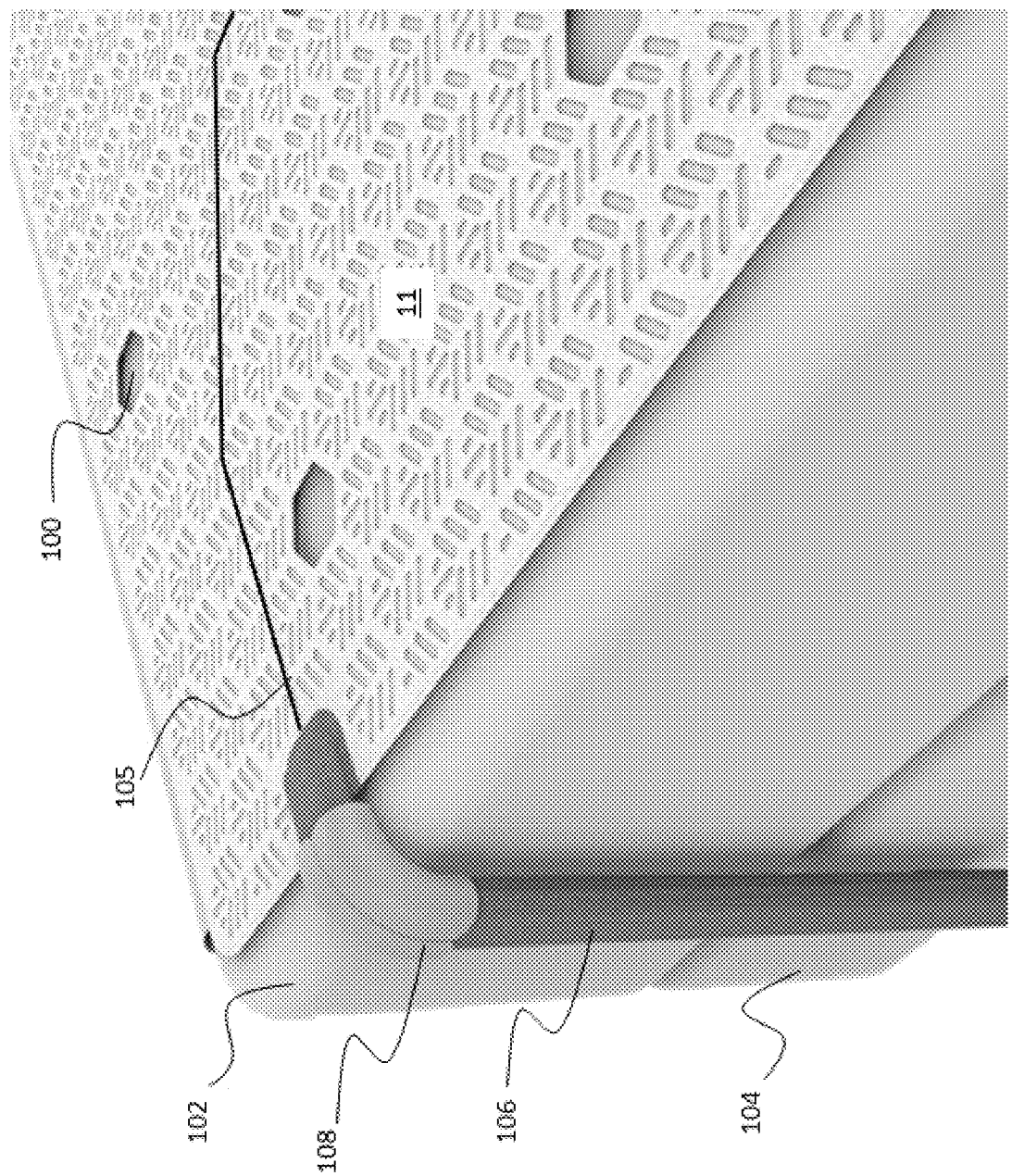
FIG. 9 is another view of the mattress pad hose elbow of FIG. 8.

FIG. 9 is another view of the mattress pad hose elbow of FIG. 8. The flexible hose 106 is positioned next to the mattress 102 and the box springs or foundation 104 using the mattress pad hose elbow 108. Advantageously, the mattress pad hose elbow 108 secures the flexible hose 106 to the side of the mattress 102 and box springs or foundation 104, providing structural support for the flexible hose 106. Further, the total height of a mattress, box springs or foundation, and/or a bed frame is not uniform. The mattress pad hose elbow 108 provides customization for the height of the mattress, the box springs or foundation, and/or the bed frame.

In another embodiment, the flexible hose is positioned next to the mattress using hook and loop tape. In yet another embodiment, the flexible hose is positioned next to the mattress using elastic. In still another embodiment, the flexible hose is positioned next to the mattress using at least one snap. Alternatively, the flexible hose is positioned next to the mattress using at least one buckle.

Figure 10:
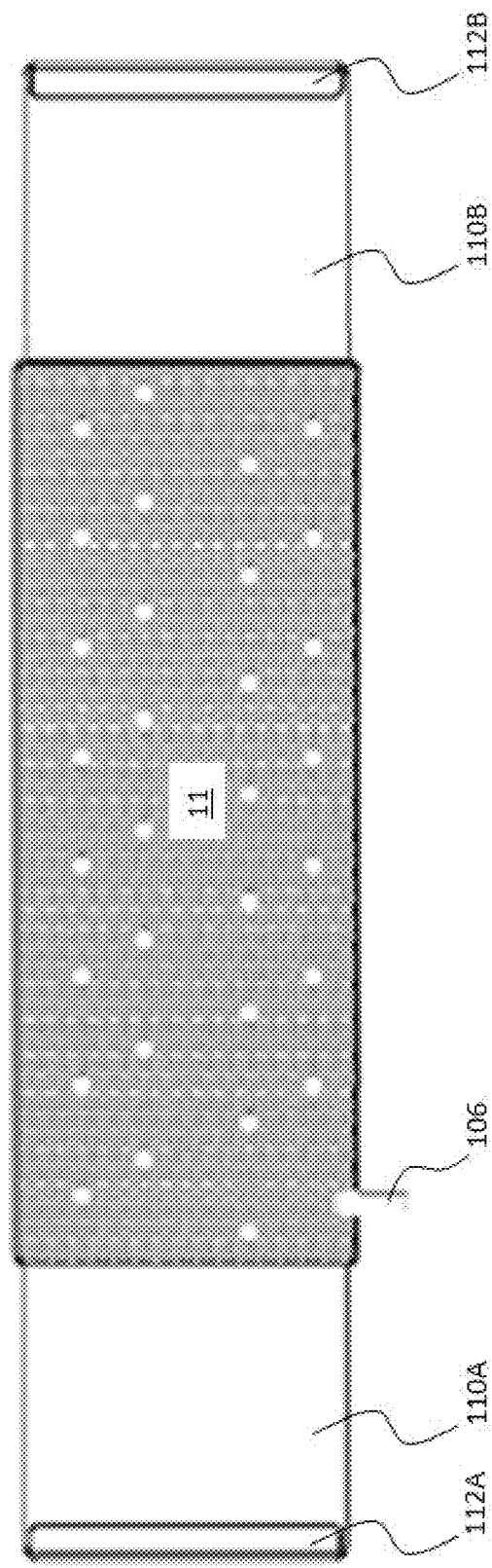
FIG. 10 is an exploded view of a single mattress pad.

FIG. 10 is a top perspective view of a single mattress pad. A top panel 110A is attached (e.g., sewn, adhered, welded) to the top of the mattress pad 11 at an attachment point 114A. A bottom panel 110B is attached (e.g., sewn, adhered, welded) to the bottom of the mattress pad 11 at an attachment point 114B. A non-slip piece 112A is attached (e.g., sewn, adhered, welded) to the top panel 110A on a side opposite the attachment point 114A. A non-slip piece 112B is attached (e.g., sewn, adhered, welded) to the bottom panel 110B on a side opposite the attachment point 114B. Preferably, the top panel 110A and the bottom panel 110B are formed from the same material as the second material (e.g., a knit or interlock fabric) on the exterior surface of the mattress pad. In a preferred embodiment, the non-slip pieces 112A, 112B are formed from foam. Alternatively, the non-slip pieces 112A, 112B are formed from latex, silicon, or rubber. The non-slip pieces 112A, 112B are preferably moisture wicking and/or antimicrobial. In one embodiment, the non-slip pieces 112A, 112B are printed onto the top panel 110A and the bottom panel 110B. In one embodiment, the top panel 110A and the bottom panel 110B are between about 18 cm (about 7 inches) and about 76 cm (about 30 inches) in length. In a preferred embodiment, top panel 110A and the bottom panel 110B are about 66 cm (about 26 inches) in length.

In another embodiment, the top panel 110A and the bottom panel 110B act as a non-slip surface. In one embodiment, the top panel 110A and the bottom panel 110B are made of gripper or anti-slip fabric. In this embodiment, the non-slip pieces 112A and 112B are not needed because the top panel 110A and the bottom panel 110B act as the non-slip surface.

The single mattress pad is preferably reversible, such that the mattress pad is operable when either exposed surface is facing upward. Advantageously, this allows the flexible hose 106 to exit on either the left or the right side of the bed. This reversibility eliminates the need to manufacture single mattress pads with a "left" configuration or a "right" configuration for single users of a full, queen, or king size bed and/or single users where a bed is positioned such that a particular configuration is required (e.g., a bed positioned against a wall).

Figure 11:
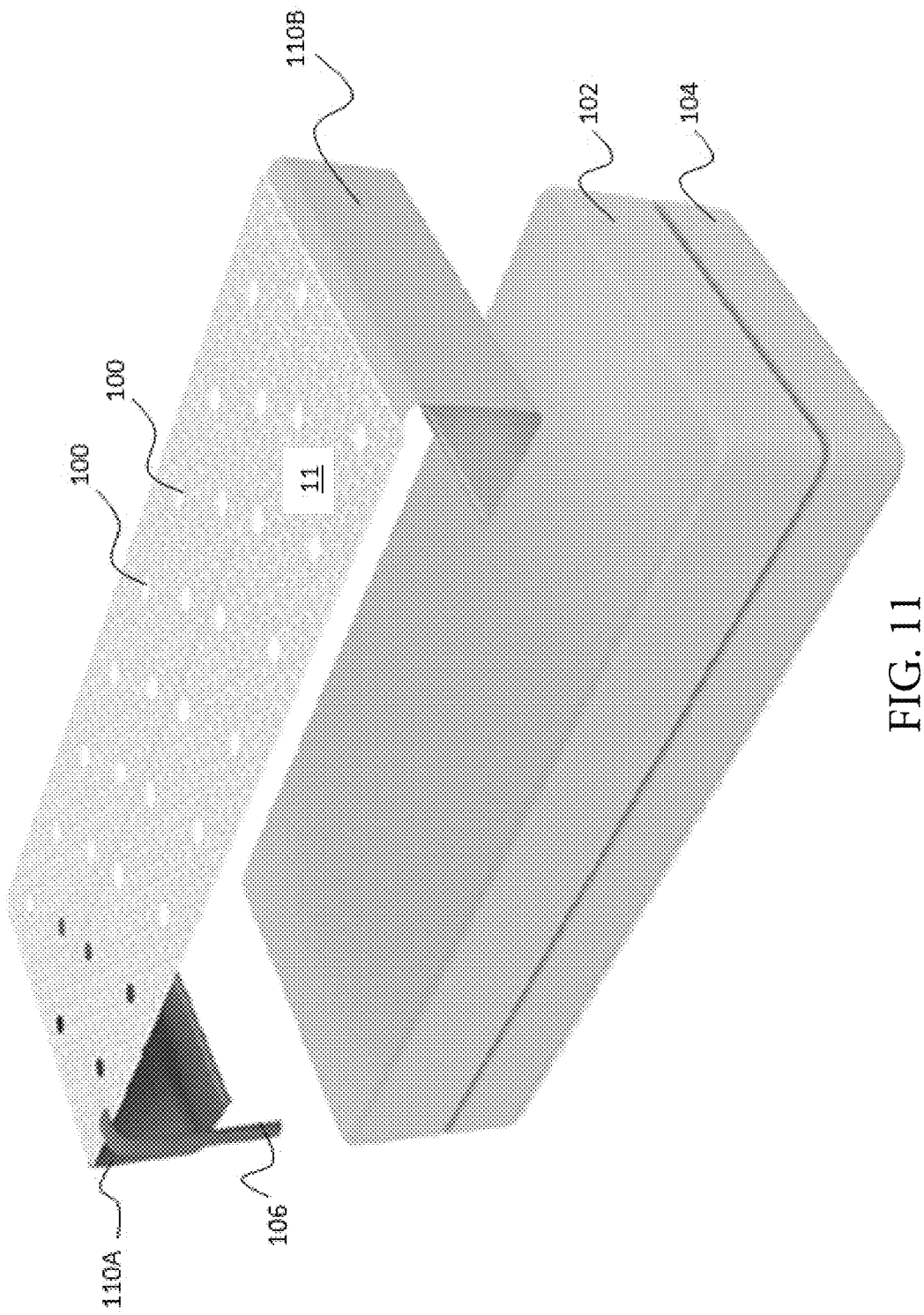
FIG. 11 is a top perspective view of a single mattress pad.

FIG. 11 is an exploded view of a single mattress pad. The mattress pad 11 is shown above the mattress 102 and box springs or foundation 104. While in use, the mattress pad 11 is placed on top of the mattress 102. The ends of the mattress pad 11 are attached to panels 110A, 110B. Panels 110A, 110B are placed over the head and foot ends of the mattress 102, with the ends of the panels 110A, 110B sandwiched between the mattress 102 and box springs or foundation 104.

As previously described, the mattress pad 11 preferably contains a plurality of holes or openings 100 in the surface of the mattress pad 11. A first layer having a plurality of holes or openings is permanently affixed to a second layer having a plurality of holes or openings along a periphery of the mattress pad and a periphery of each of the plurality of holes or openings. At least one interior chamber is defined between an interior surface of the first layer and an interior surface of the second layer. The at least one interior chamber is constructed and configured to retain a fluid without leaking. The interior surface of the first layer and the interior surface of the second layer are made of at least one layer of a waterproof material.

In an alternative embodiment, the mattress pad 11 does not contain a plurality of holes or openings in the surface in the mattress pad 11. In one embodiment, the waterproof material is stretchable. In a preferred embodiment, the stretch rate of the waterproof material is equal to or greater than the stretch rate of surrounding materials (e.g., a mattress). Advantageously, this prevents the mattress pad 11 from gathering and bunching underneath a user.

Figure 12:
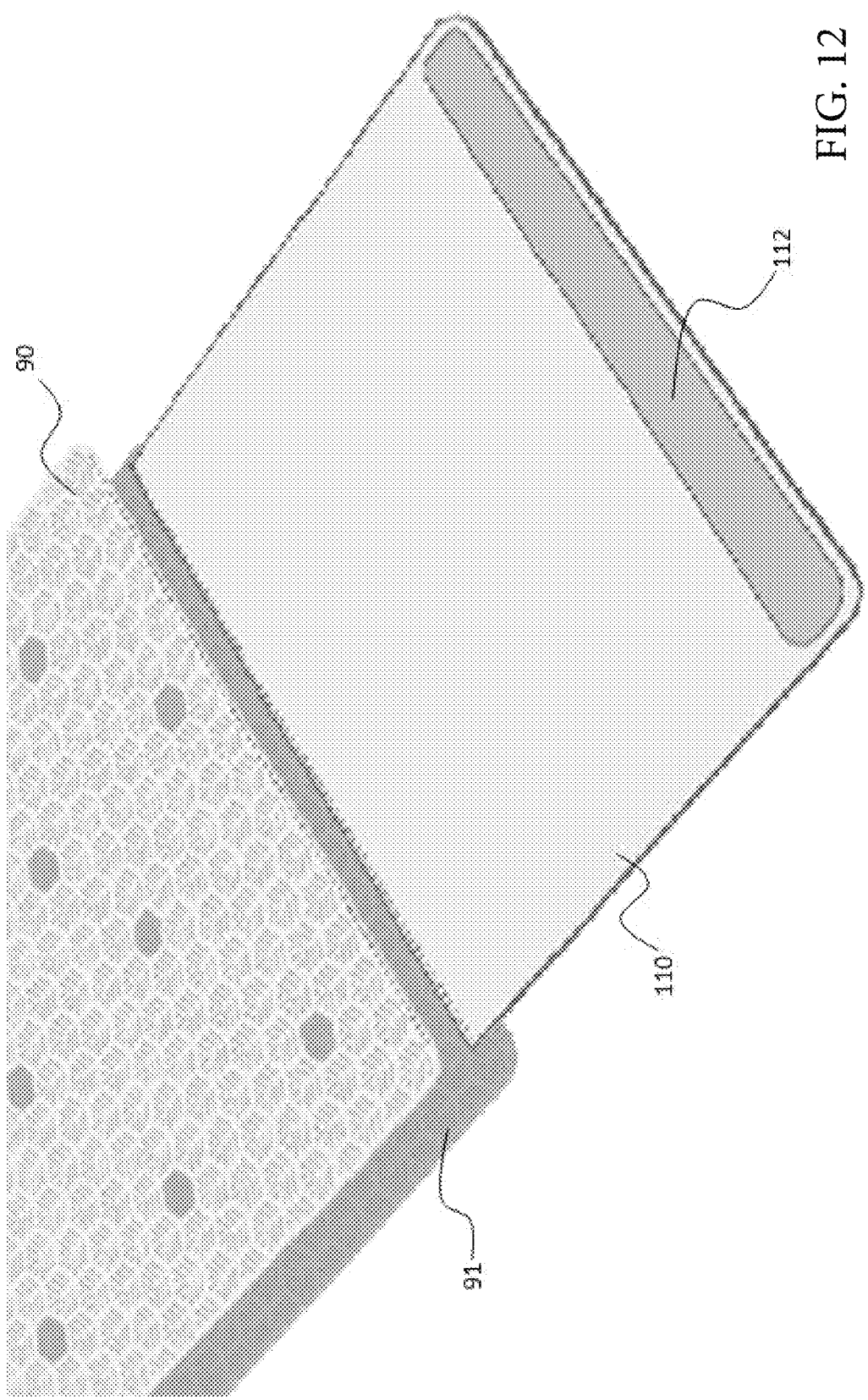
FIG. 12 is a top perspective view of an end of a single mattress pad.

FIG. 12 is an exploded view of an end of a single mattress pad. The mattress pad 11 is formed of at least two layers of waterproof material as shown in FIGS. 6A-6D. In one embodiment, the panel 110 is permanently affixed (e.g., sewn, adhered, welded) between a first layer of a waterproof material 602 and a second layer of a waterproof material 604. On the opposite end from where the panel 110 is attached to the mattress pad 11, a non-slip piece 112 is permanently affixed (e.g., sewn, adhered, welded) to the panel. In a preferred embodiment, the non-slip piece 112 is formed from foam. Alternatively, the non-slip pieces 112 are formed from latex, silicon, or rubber. The non-slip pieces 112 are preferably moisture wicking and/or antimicrobial.

Figure 13:
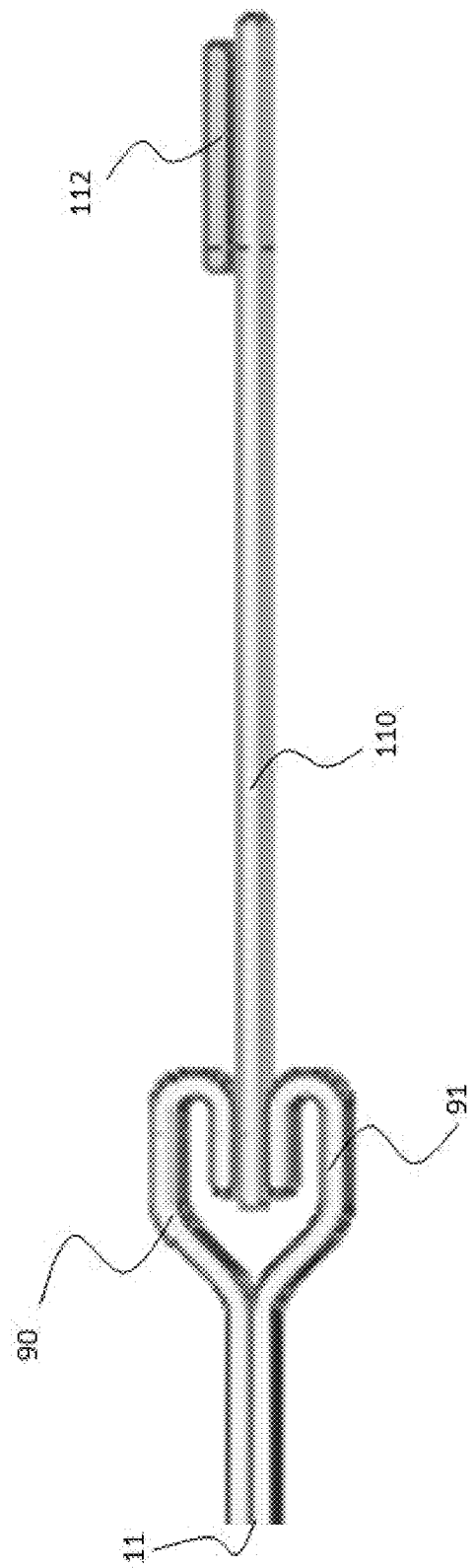
FIG. 13 is a side perspective view of an end of a single mattress pad.

FIG. 13 is a side perspective view of an end of a single mattress pad. The mattress pad 11 has a first layer of waterproof material 602 and a second layer of waterproof material 604. A first end of panel 110 is attached to the first layer of waterproof material 602 and the second layer of waterproof material 604. The panel 110 is permanently affixed (e.g., sewn, adhered, welded) between the first layer of waterproof material 602 and the second layer of waterproof material 604. In a preferred embodiment, the external surface of the first layer of waterproof material 602 and the second layer of waterproof material 604 are folded over to attach to the first end of panel 110. A non-slip piece 112 is permanently affixed (e.g., sewn, adhered, welded) to the end opposite of the first end of panel 110. In a preferred embodiment, the non-slip piece 112 is formed from foam. Alternatively, the non-slip pieces 112 are formed from latex, silicon, or rubber. The non-slip pieces 112 are preferably moisture wicking and/or antimicrobial.

In alternative embodiments, the mattress pad includes interlock or knit fabric on exterior surfaces of the mattress pad. In other embodiments, the exterior surfaces of the mattress pad are covered with a woven fabric, a non-woven fabric, or a polymer film (e.g., urethane or thermoplastic polyurethane (TPU)). Additionally or alternatively, the mattress pad includes a spacer layer between an interior surface of the first layer of waterproof material 602 and an interior surface of the second layer of waterproof material 604.

Figure 14:
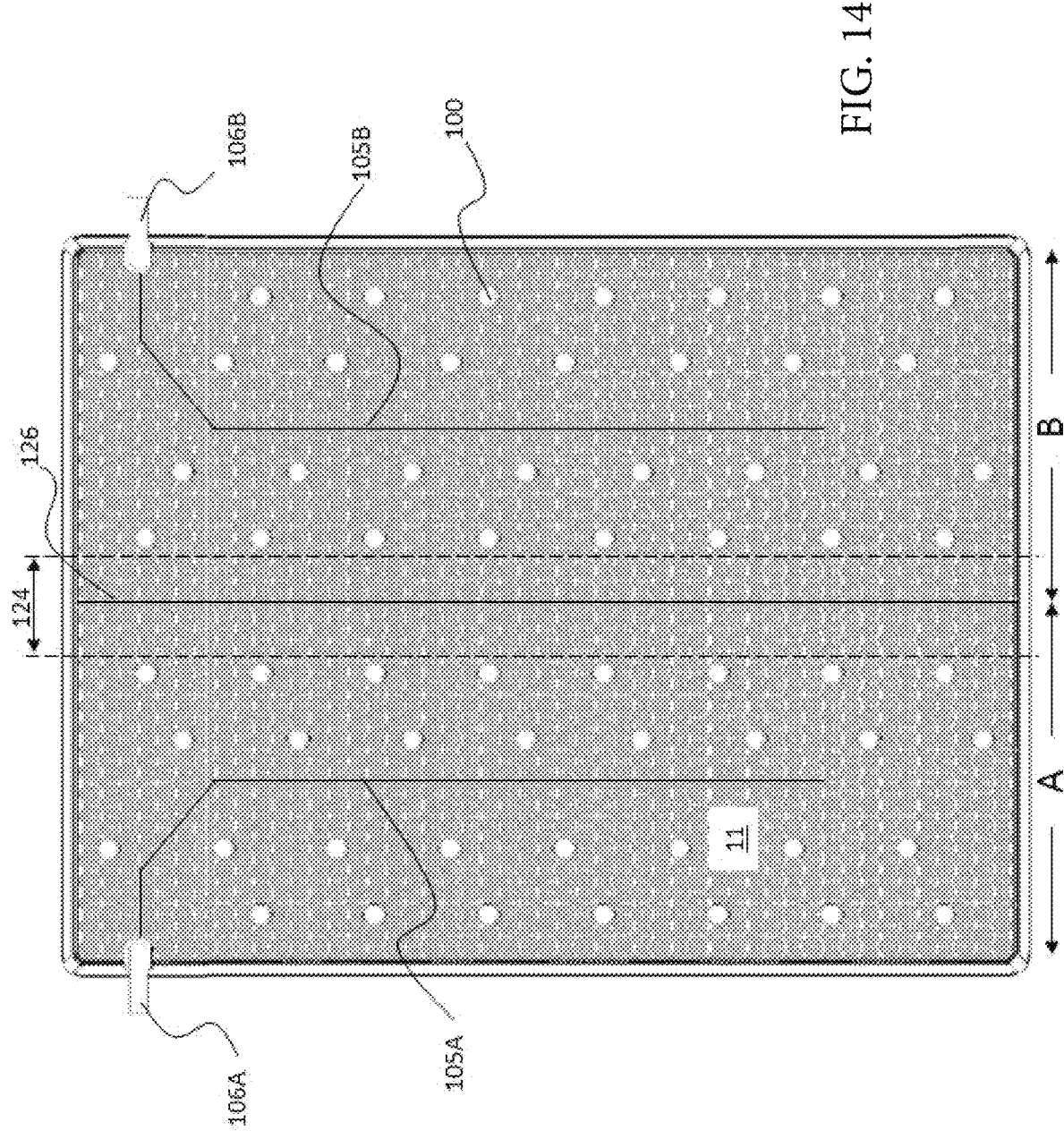
FIG. 14 is a top perspective view of a double mattress pad.

FIG. 14 is a top perspective view of a double mattress pad. The mattress pad 11 has two independent thermally regulated surface zones "A" and "B". The mattress pad 11 has a first flexible hose 106A and a second flexible hose 106B. In a preferred embodiment, the first flexible hose 106A attaches to a first control unit (not shown) and the second flexible hose 106B attaches to a second control unit (not shown). In a preferred embodiment, the center of the mattress pad 11 contains an area free of holes or openings 124. The area free of holes or openings 124 contains a welded separator 126, which provides a boundary between the two independent thermally regulated surface zones "A" and "B".

Figure 15:
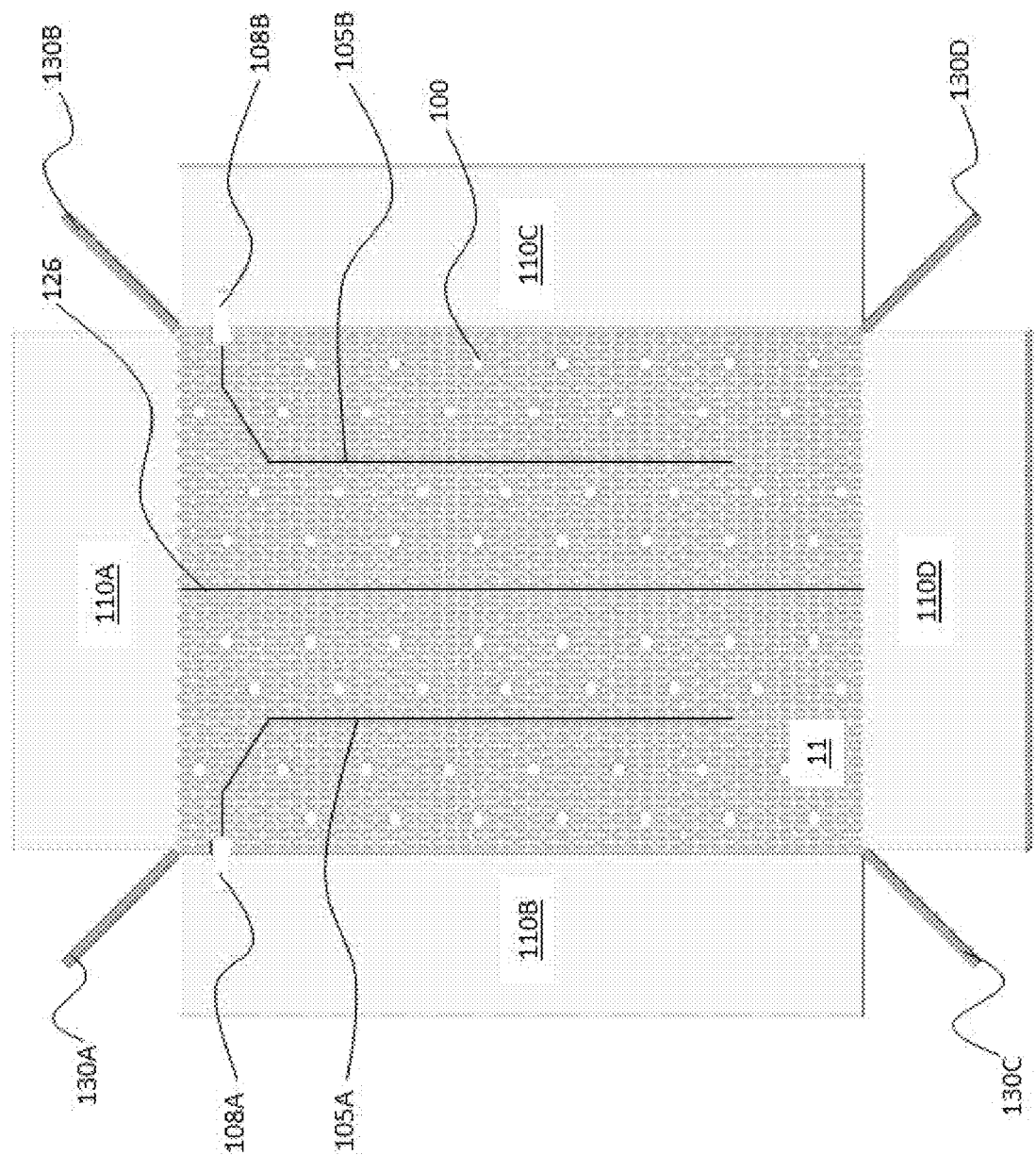
FIG. 15 is an exploded view of a double mattress pad.

FIG. 15 is another top perspective view of a double mattress pad. The mattress pad 11 has a top end panel 110A, a left side panel 110B, a right side panel 110C, and a bottom end panel 110D. The top end panel 110A, the left side panel 110B, the right side panel 110C, and the bottom end panel 110D are preferably formed from a material with stretch (e.g., interlock or knit). In a preferred embodiment, each corner of the mattress pad 11 contains at least one non-slip piece. In one embodiment, a top non-slip piece and a bottom non-slip piece are attached to each corner of the mattress pad 11. In the embodiment shown in FIG. 15, the corner between the top panel 110A and the left side panel 110B has a non-slip piece 130A, the corner between the top panel 110B and the right side panel 110C has a non-slip piece 130B, the corner between the left side panel 110B and the bottom end panel 110D has a non-slip piece 130C, and the corner between the right side panel 110C and the bottom end panel 110D has a non-slip piece 130D.

The mattress pad 11 preferably contains at least one weld line or other separation to help manage the flow of fluid in the at least one interior chamber. The at least one weld line 105 directs the fluid flow through the pad from head to foot, and returns the fluid to the control unit via the return line. In FIG. 15, the mattress pad has a first weld line 105A to help manage the flow of fluid in the interior chamber of zone "A" and a second weld line 105B to help manage the flow of fluid in the interior chamber of zone "B". Although only one weld line is shown for each independent temperature zone, it is equally possible to have two or more weld lines for each independent temperature zone.

Figure 16:
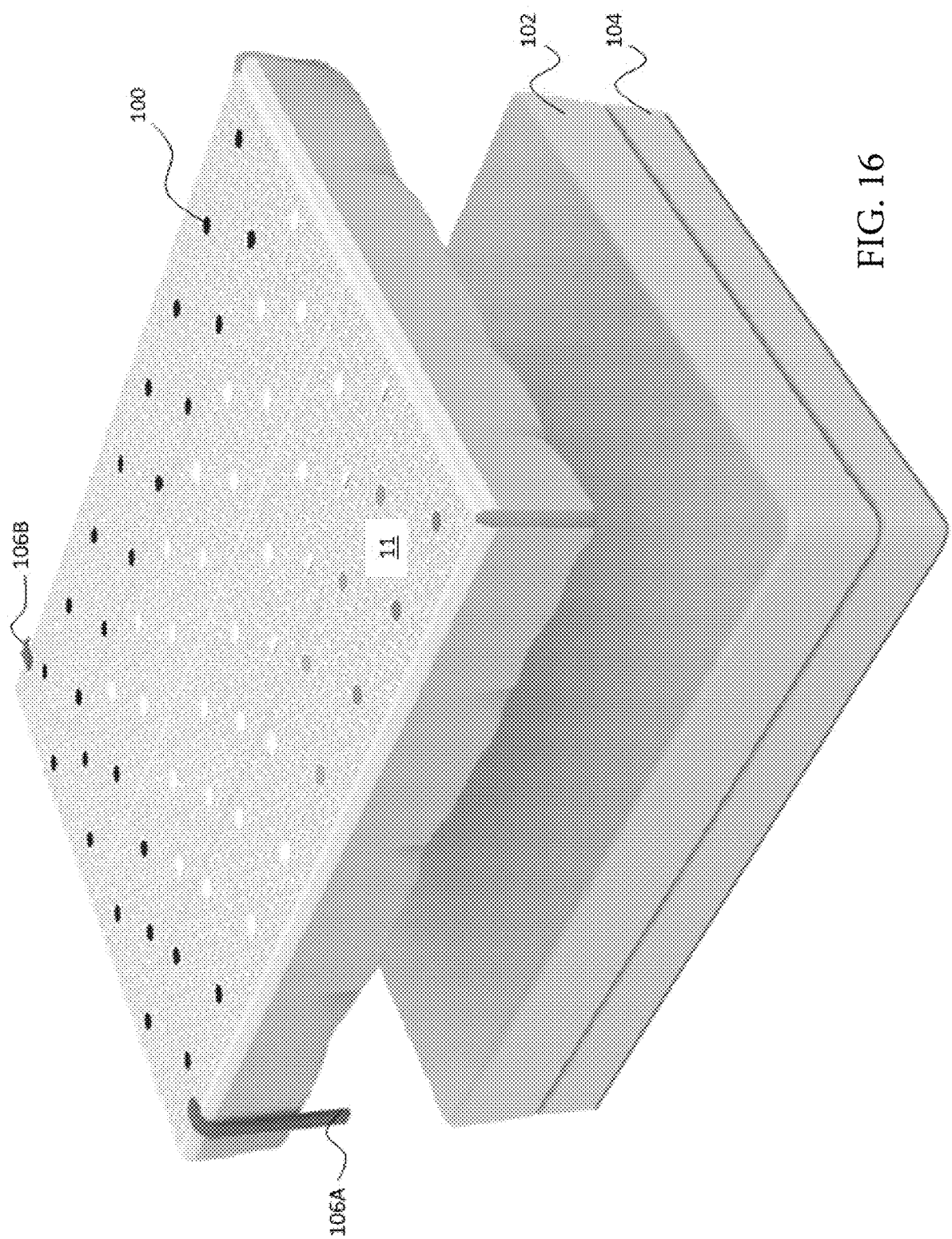
FIG. 16 is another top perspective view of a double mattress pad.

FIG. 16 is an exploded view of a double mattress pad. The mattress pad 11 is shown above the mattress 102 and box springs or foundation 104. The mattress pad 11 has a first flexible hose 106A and a second flexible hose 106B. In a preferred embodiment, the first flexible hose 106A attaches to a first control unit (not shown) and the second flexible hose 106B attaches to a second control unit (not shown). Alternatively, the first flexible hose 106A and the second flexible hose 106B attach to the same control unit. The surface of the mattress pad 11 contains a plurality of holes or openings 100 in the surface of the mattress pad 11.

Figure 17:
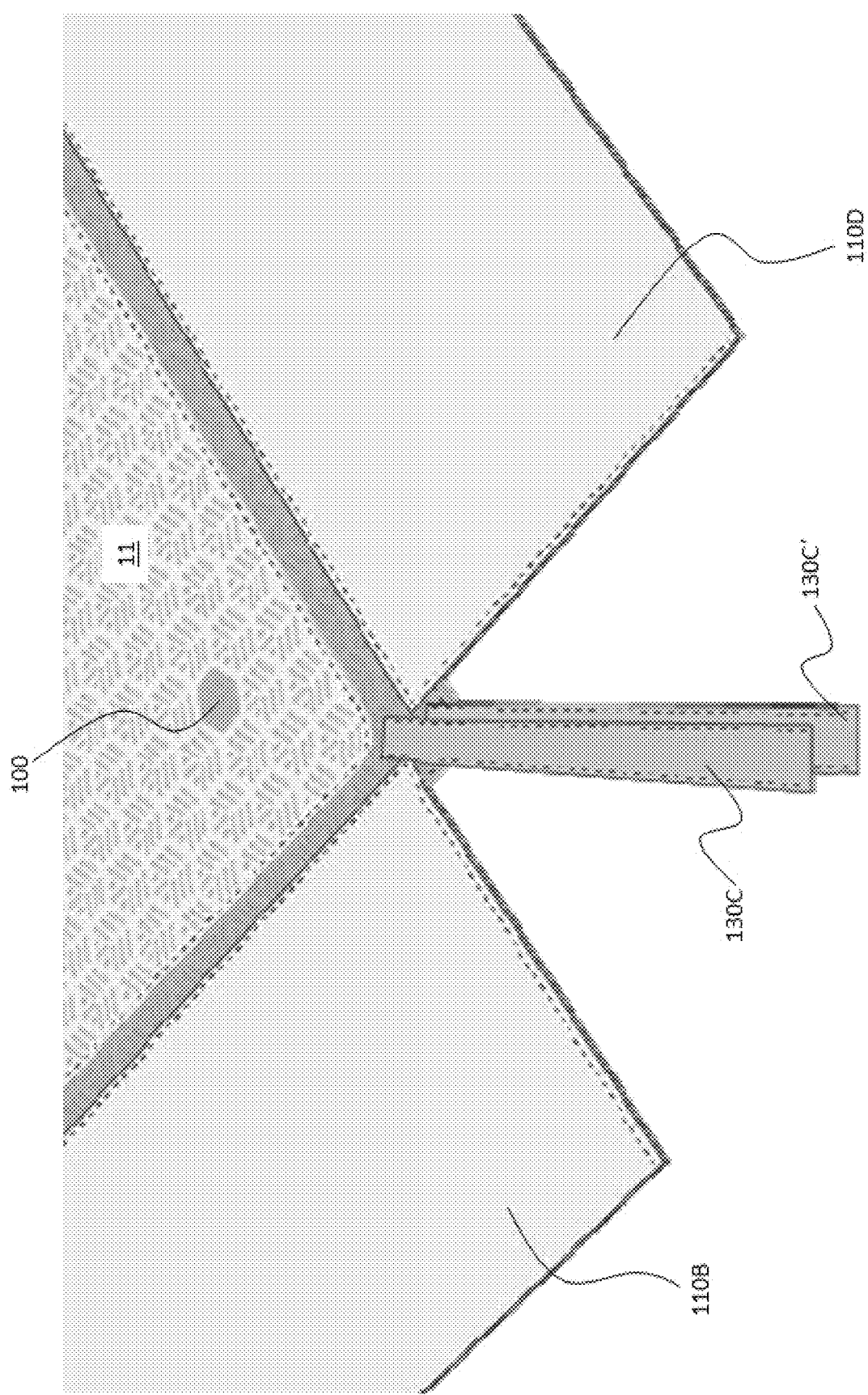
FIG. 17 is a view of the corner of a double mattress pad.

FIG. 17 is an exploded view of the bottom left corner of one embodiment of a double mattress pad before the mattress pad is secured to the bed. In a preferred embodiment, each corner of the mattress pad 11 contains a top non-slip piece 130C and a bottom non-slip piece 130C'. In FIG. 17, the top non-slip piece 130C and the bottom non-slip piece 130C' are shown attached (e.g., sewn, adhered, welded) to the corner formed between the left side panel 110B and the bottom end panel 110D. The left side panel 110B and the bottom end panel 110D are preferably formed from a material with stretch (e.g., interlock or knit). In one embodiment, elastic is attached (e.g., sewn, adhered, welded) to a bottom edge of the left side panel 110B and a bottom edge of the bottom end panel 110D. Alternatively, elastic is encased at the bottom edge of the left side panel 110B and the bottom edge of the bottom end panel 110D.

To secure the mattress pad 11 to the bed, the edge of the left side panel 110B and the edge of the bottom panel 110D are placed on top of the bottom non-slip piece 130C'. The top non-slip piece 130 is then placed on top the left side panel 110B, bottom panel 110D, and the bottom non-slip piece 130C'. The top non-slip piece 130C and bottom non-slip piece 130C' are preferably formed from non-slip foam. Alternatively, the top non-slip piece 130C and bottom non-slip piece 130C' are formed from silicone, rubber, or latex. In one embodiment, the left side panel 110B and the bottom panel 110D are formed from a material with stretch (e.g., interlock or knit). The top non-slip piece 130C and bottom non-slip piece 130C' provide friction to keep the mattress pad in place.

Figure 18:
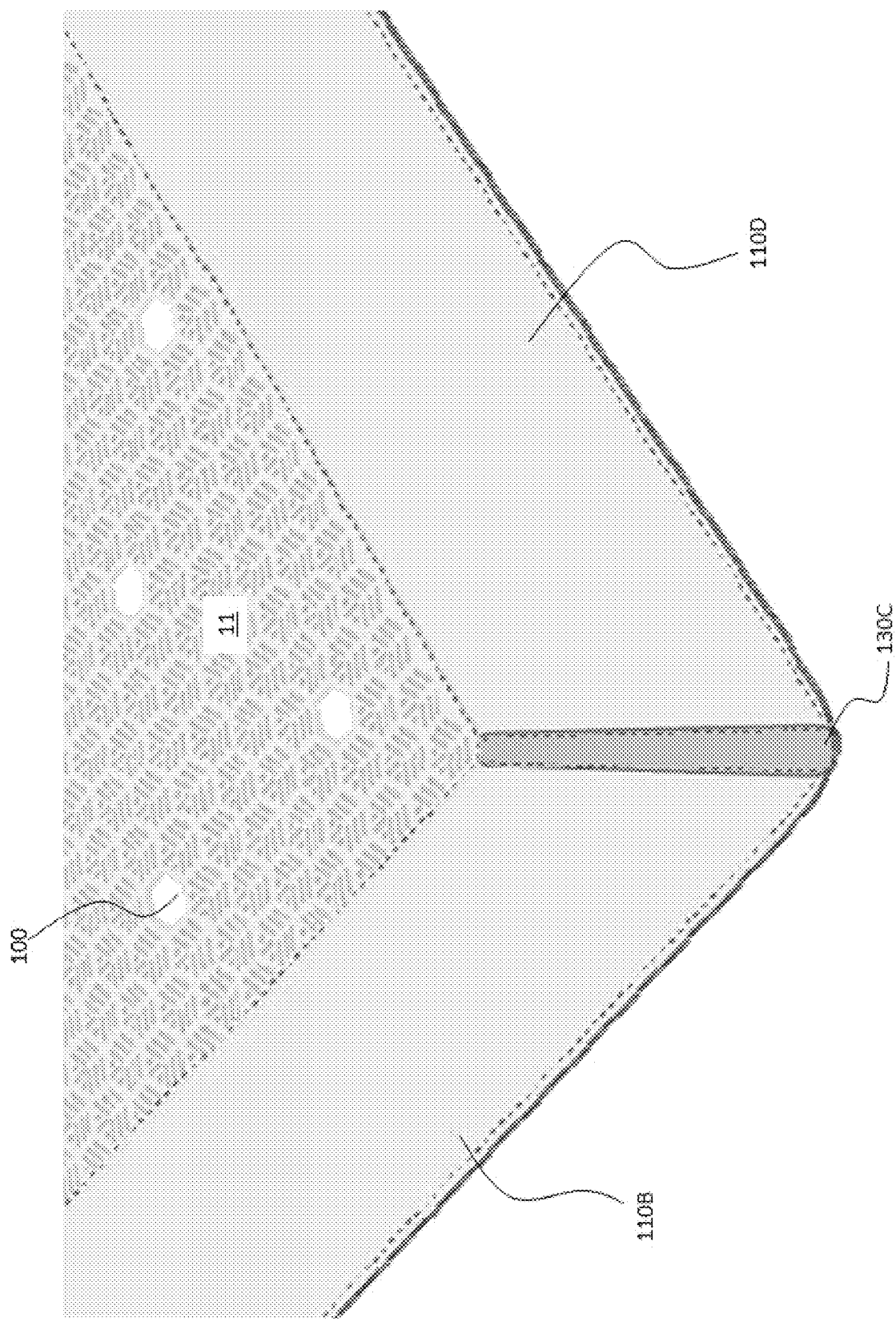
FIG. 18 is another view of the corner of a double mattress pad.

FIG. 18 is a view of the bottom left corner of a double mattress pad after the mattress pad is secured to the bed.

Figure 19:
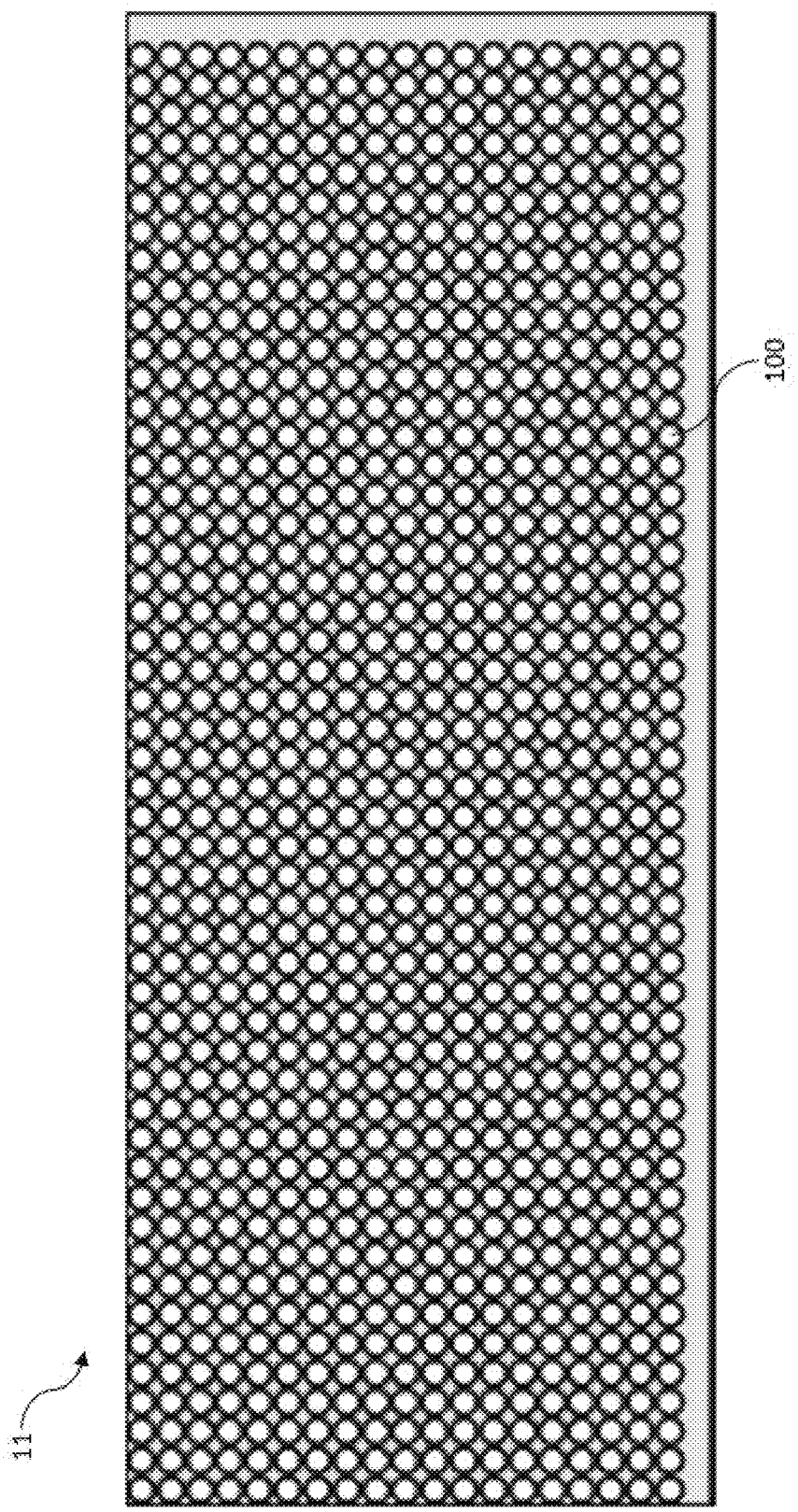
FIG. 19 is a view of another embodiment of a mattress pad.

FIG. 19 is a view of another embodiment of the mattress pad. The plurality of holes or openings 100 is shown in a circle shape in FIG. 19. The voids created by the plurality of holes or openings 100 include at least 80% of the surface area of the mattress pad 11 in this embodiment.

As mentioned previously, the at least one remote device is operable to programmatically control the target temperatures over time, such as over the course of a night's sleep. Because the target temperatures can be set at any time, those target temperatures can be manipulated through the sleeping period in order to match user preferences or a program to correlate with user sleep cycles to produce a deeper, more restful sleep.

The following documents provide general information regarding sleep and sleep monitoring, and are incorporated herein by reference in their entirety: (1) Iber et al. The AASM manual for the scoring of sleep and associated events: rules, terminology and technical specifications. 1st ed. Westchester, Ill.: American Academy of Sleep Medicine, 2007. (2) Berry et al. The AASM Manual for the Scoring of Sleep and Associated Events: Rules, Terminology, and Technical Specifications. www.aasm.org. Darien, Ill.: American Academy of Sleep Medicine, 2015. (3) Orem, et al. (Eds.). Physiology in Sleep. New York: Elsevier, 2012. (4) Sleep Research Society. Basics of Sleep Behavior. Los Angeles, Calif.: UCLA and Sleep Research Society, 1993. (5) Hirshkowitz, et al. The physiology of sleep. In Guilleminault (Ed.). Handbook of Clinical Neurophysiology—Clinical Neurophysiology of Sleep Disorders. Philadelphia: Elsevier, 2005; 3-20. (6) Avidian. Normal Sleep in Humans. In: Kryger, et al. (Eds.). Atlas of Clinical Sleep Medicine (2nd ed.). Philadelphia, Pa.: Elsevier, 2014; 70-97. (7) Consumer Technology Association. Definitions and Characteristics for Wearable Sleep Monitors, ANSI/CTA/NSF-2052.1, September 2016.

There are two main types of sleep: rapid eye movement (REM) sleep and non-rapid eye movement (non-REM) sleep. A sleep cycle typically lasts about 90 minutes, with REM sleep and non-REM sleep alternating within the sleep cycle. Non-REM sleep is divided into three stages: Stage 1 ("N1", drowsy sleep), Stage 2 ("N2", light sleep), and Stage 3 ("N3", deep sleep).

The N1 stage is a transitional stage between wakefulness and sleep, and is characterized as a very light and easily disrupted sleep. During N1 sleep, breathing becomes more regular and the heart rate slows. N1 sleep typically lasts less than 10 minutes and accounts for approximately 2-5% of total sleep time. The N2 stage is a deeper stage of sleep. N2 sleep accounts for approximately 45-50% of total sleep time because sleepers pass through the N2 stage multiple times throughout the night. The N3 stage is deep sleep. During N3 sleep, brain temperature, breathing rate, heart rate, and blood pressure are each at their lowest levels. Deep sleep is associated with repairing and regrowing tissues, building bone and muscle, and strengthening the immune system.

REM sleep is a stage of sleep associated with random movement of the eyes. REM sleep accounts for approximately 20-25% of total sleep time. The first period of REM sleep begins approximately 90 minutes after sleep begins and lasts for approximately 10 minutes. Further, REM sleep is more prevalent in the last half of a sleeping period, such that the last REM stage may last up to about 60 minutes. Heart rate, breath rate, and blood pressure increase during REM sleep. Additionally, due to high brain activity, dreams are more prevalent in REM sleep. REM is associated with preserving memories and building neural connections.

Because deep sleep and REM sleep are the most regenerative parts of the sleep cycle, it is most beneficial to spend most of a sleeping period in deep sleep and/or REM sleep. The target temperature of the mattress pad can be manipulated over time through programmatic control using the at least one remote device. Because the target temperature can be manipulated using the at least one remote device, those target temperatures can be manipulated through the sleeping period to allow a user to spend more time in REM and/or deep sleep.

Figure 20A:
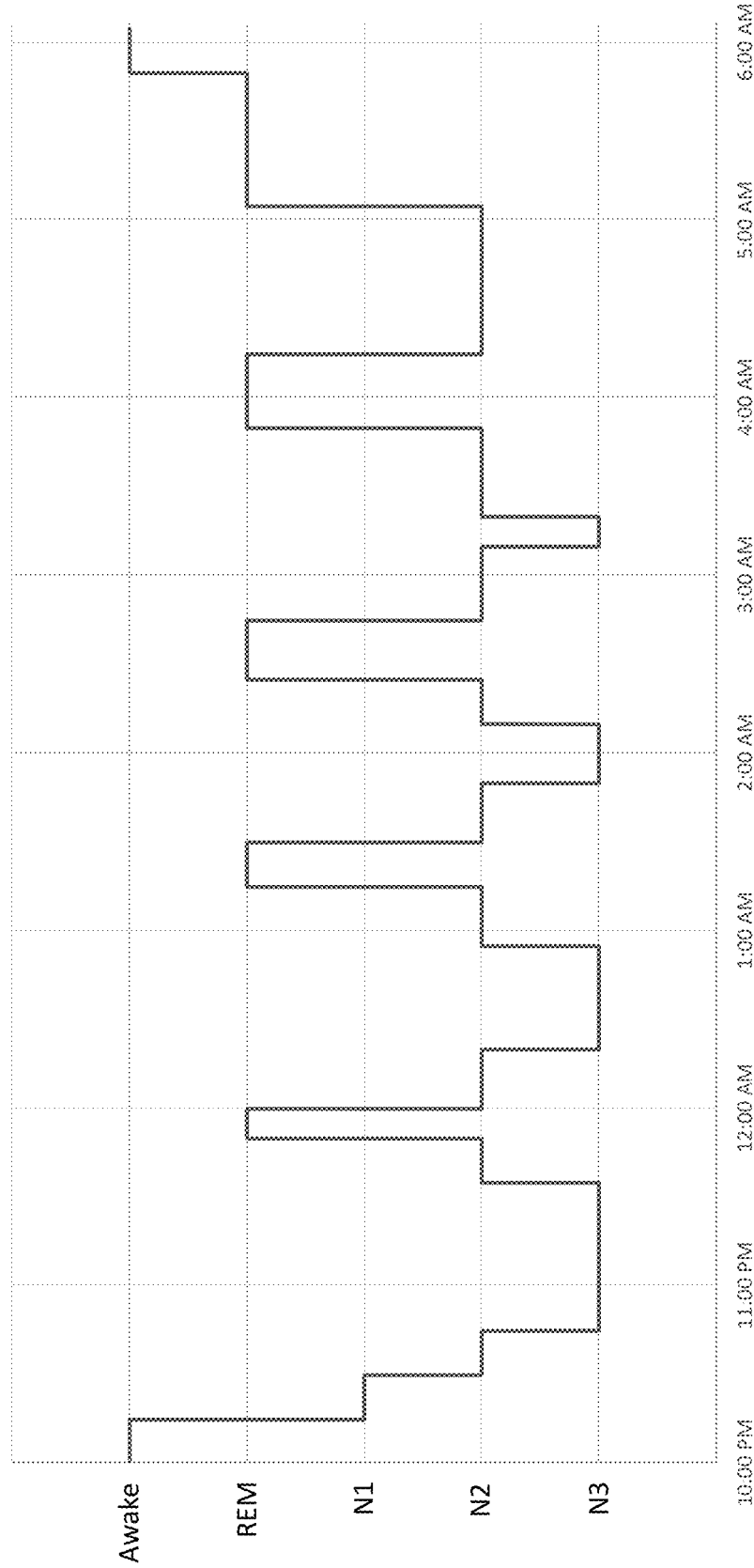
FIG. 20A illustrates a graph of a sleep cycle for a normal sleeper.

FIG. 20A illustrates a graph of the sleep cycle for a normal sleeper. A normal sleeper enters deep sleep 3-5 times in a sleeping period.

Figure 20B:
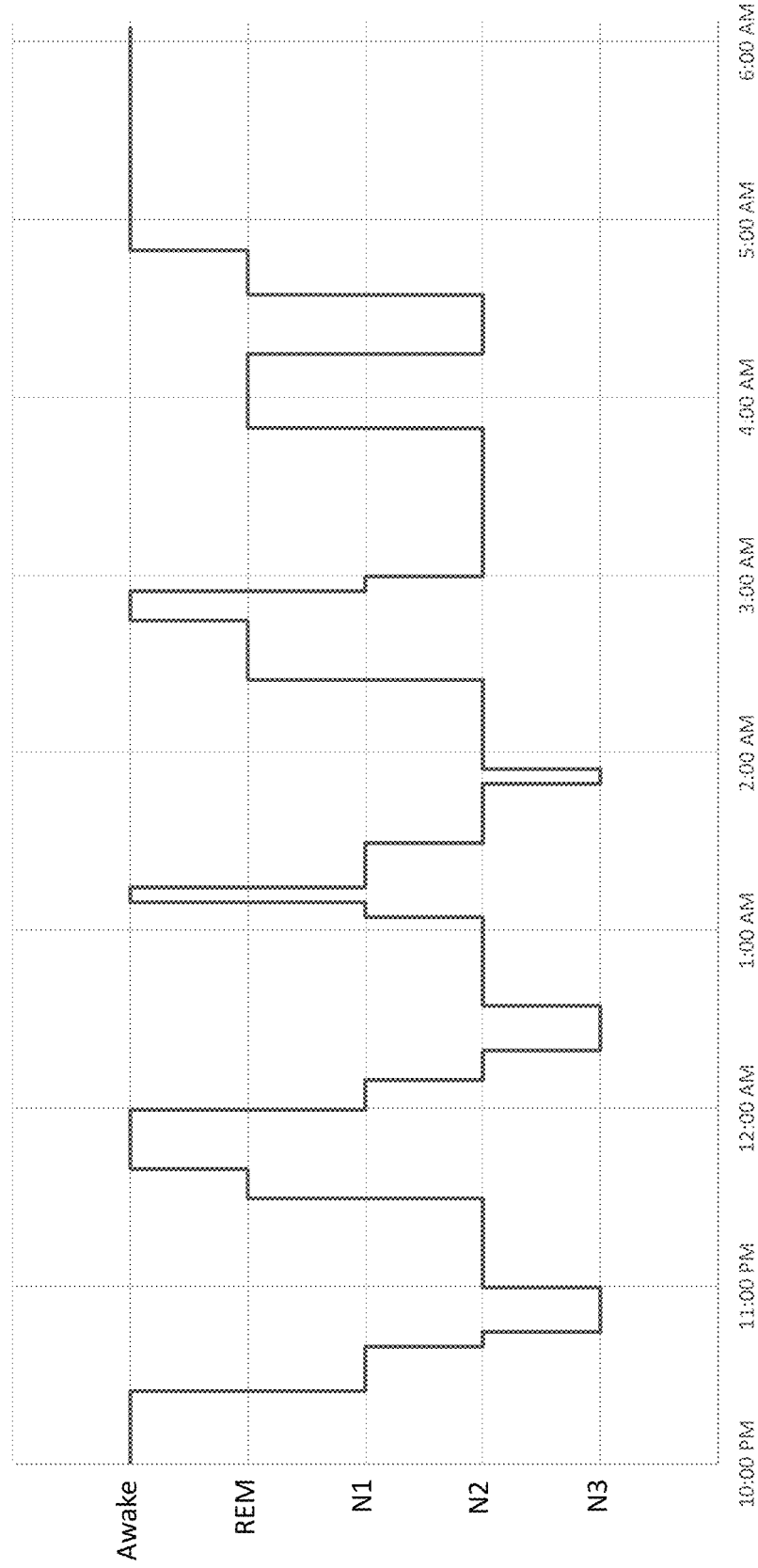
FIG. 20B illustrates a graph of a sleep cycle for a restless sleeper.

FIG. 20B illustrates a graph of the sleep cycle for a restless sleeper. Restless sleep is characterized by little or no deep sleep. Additionally, the sleep cycles are uneven. The sleeper may awaken several times throughout the night and have difficulty falling back asleep. Further, the time to sleep may be delayed and/or the sleeper may wake up earlier, as shown in FIG. 19B.

Figure 20C:
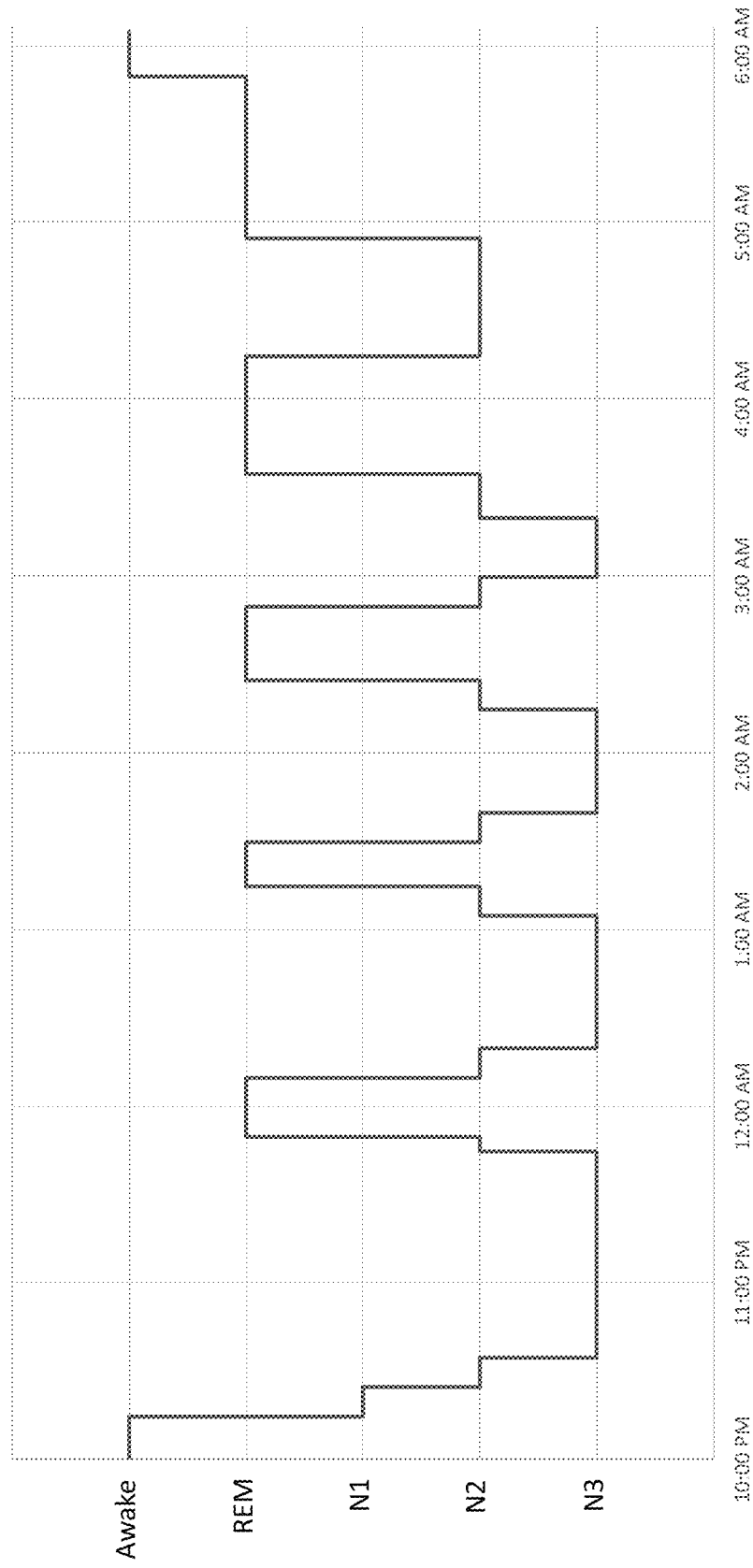
FIG. 20C illustrates a graph of a sleep cycle for a temperature-manipulated sleeper

FIG. 20C illustrates a graph of the sleep cycle for a temperature-manipulated sleeper. The mattress pad 11 cools the user to induce a sleep cycle. Additional cooling may be applied while the user is in deep sleep to extend the time spent in deep sleep. Slight warming (e.g., 0.278° C./minute (0.5° F./minute)) may be applied within a sleep cycle to move the user from deep sleep to REM sleep at a faster pace, such that less time is spent in N2 sleep. At the end of the last sleep cycle, the temperature is increased (e.g., 0.278° C./minute (0.5° F./minute)) to gently awaken the user. Advantageously, gently awakening the user by increasing the temperature prevents sleep inertia. Sleep inertia is characterized by impaired cognitive and motor function after awakening. It can take several hours to recover from sleep inertia, which presents a danger for individuals who need to make important decisions or perform tasks safely (e.g., driving).

Figure 21:
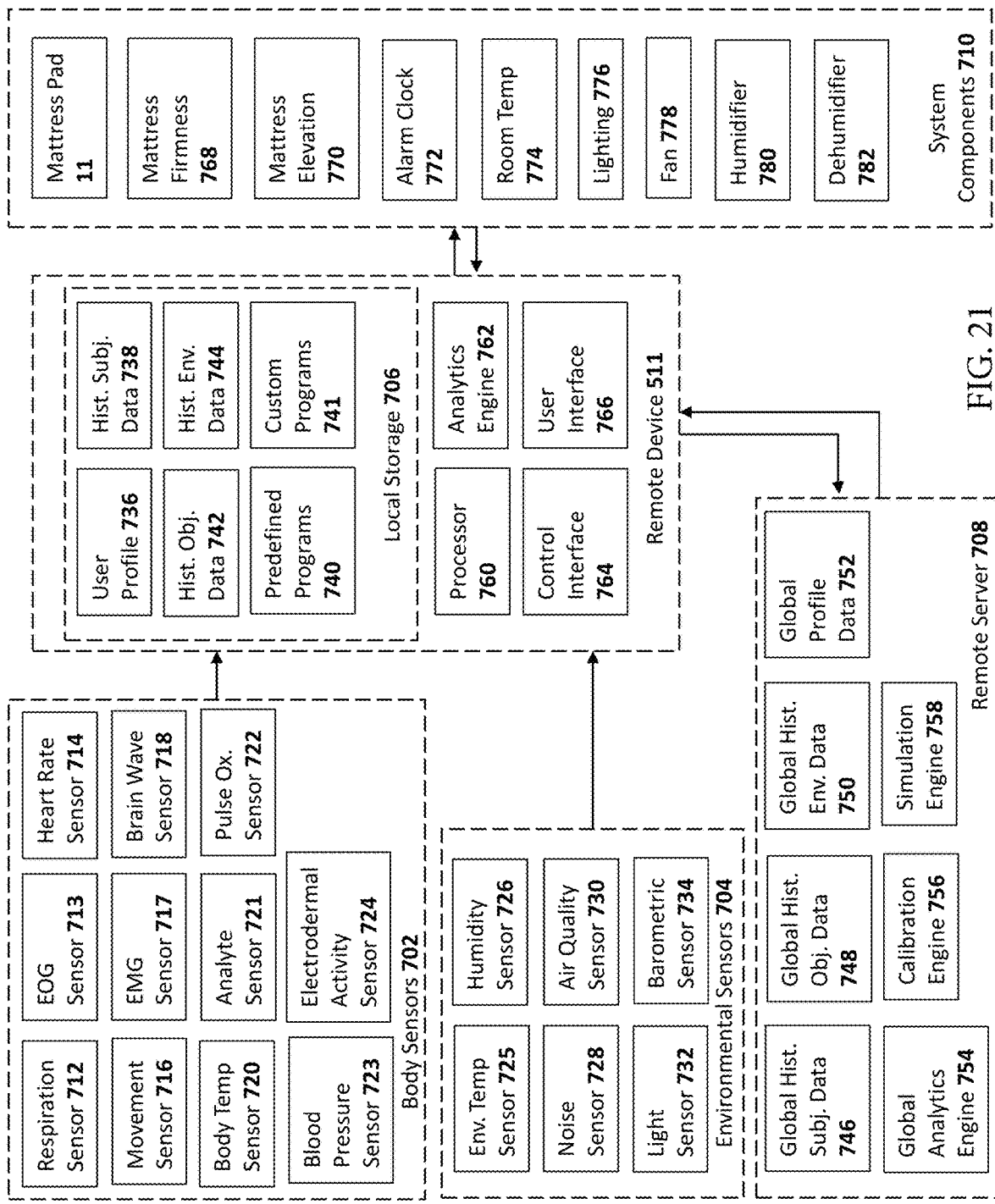
FIG. 21 is a block diagram of one embodiment of the sleep system.

FIG. 21 is a block diagram of one embodiment of the sleep system. The sleep system includes body sensors 702, environmental sensors 704, a remote device 511 with local storage 706, a remote server 708, and system components 710. The body sensors 702 include a respiration sensor 712, an electrooculography sensor 713, a heart rate sensor 714, a movement sensor 716, an electromyography sensor 717, a brain wave sensor 718, a body temperature sensor 720, an analyte sensor 721, a pulse oximeter sensor 722, a blood pressure sensor 723, and/or an electrodermal activity sensor 724.

The respiration sensor 712 measures a respiratory rate. In one embodiment, the respiration sensor 712 is incorporated into a wearable device. In another embodiment, the respiration sensor 712 is incorporated into a patch or a bandage. Alternatively, the respiratory rate is estimated from an electrocardiogram, a photoplethysmogram (e.g., a pulse oximeter), and/or an accelerometer. In yet another embodiment, the respiratory sensor 712 uses a non-contact motion biomotion sensor to monitor respiration.

The electrooculography (EOG) sensor 713 measures the corneo-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position.

The heart rate sensor 714 is preferably incorporated into a wearable device (e.g., Fitbit, Jawbone). Alternatively, the heart rate sensor 714 is attached to the user with a chest strap. In another embodiment, the heart rate sensor 714 is incorporated into a patch or a bandage. In yet another embodiment, the heart rate sensor is incorporated into a sensor device on the mattress (e.g., Beddit). The heart rate is determined using electrocardiography, pulse oximetry, ballistocardiography, or seismocardiography.

The movement sensor 716 is an accelerometer and/or a gyroscope. In one embodiment, the accelerometer and/or the gyroscope are incorporated into a wearable device (e.g., Fitbit, Jawbone, actigraph). In another embodiment, the accelerometer and/or the gyroscope are incorporated into a smartphone. In alternative embodiment, the movement sensor 716 is a non-contact sensor. In one embodiment, the movement sensor 716 is at least one piezoelectric sensor. In another embodiment, the movement sensor 716 is a pyroelectric infrared sensor (i.e., a "passive" infrared sensor). In yet another embodiment, the movement sensor 716 is at least one pressure sensor embedded in a mattress or mattress topper. Alternatively, the movement sensor 716 is incorporated into a smart fabric.

The electromyography (EMG) sensor 717 records the electrical activity produced by skeletal muscles. Impulses are recorded by attaching electrodes to the skin surface over the muscle. In a preferred embodiment, three electrodes are placed on the chin. One in the front and center and the other two underneath and on the jawbone. These electrodes demonstrate muscle movement during sleep, which can be used to detect REM or NREM sleep. In another embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg can be used to detect movement of the legs during sleep, which may occur with Restless Leg Syndrome or Periodic Limb Movements of Sleep.

The brain wave sensor 718 is preferably an electroencephalogram (EEG) with at least one channel. In a preferred embodiment, the EEG has at least two channels. Multiple channels provide higher resolution data.

The body temperature sensor 720 measures core body temperature and/or skin temperature. The body temperature sensor 720 is a thermistor, an infrared sensor, or thermal flux sensor. In one embodiment, the body temperature sensor 720 is incorporated into an armband or a wristband. In another embodiment, the body temperature sensor 720 is incorporated into a patch or a bandage. In yet another embodiment, the body temperature sensor 720 is an ingestible core body temperature sensor (e.g., CorTemp). The body temperature sensor 720 is preferably wireless.

The analyte sensor 721 monitors levels of an analyte in blood, sweat, or interstitial fluid. In one embodiment, the analyte is an electrolyte, a small molecule (molecular weight<900 Daltons), a protein, and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin. The analyte sensor 721 is preferably non-invasive. Alternatively, the analyte sensor 721 is minimally invasive or implanted. In one embodiment, the analyte sensor 721 is incorporated into a wearable device. Alternatively, the analyte sensor 721 is incorporated into a patch or a bandage.

The pulse oximeter sensor 722 monitors oxygen saturation. In one embodiment, the pulse oximeter sensor 722 is worn on a finger, a toe, or an ear. In another embodiment, the pulse oximeter sensor 722 is incorporated into a patch or a bandage. The pulse oximeter sensor 722 is preferably wireless. Alternatively, the pulse oximeter sensor 722 is wired. In one embodiment, the pulse oximeter sensor 722 is connected by a wire to a wrist strap or a strap around a hand. In another embodiment, the pulse oximeter sensor 722 is combined with a heart rate sensor 714.

The blood pressure sensor 723 is a sphygmomanometer. The sphygmomanometer is preferably wireless. Alternatively, the blood pressure sensor 723 estimates the blood pressure without an inflatable cuff (e.g., Salu Pulse+). In one embodiment, the blood pressure sensor 723 is incorporated into a wearable device.

The electrodermal activity sensor 724 measures sympathetic nervous system activity. Electrodermal activity is more likely to have high frequency peak patterns (i.e., "storms") during deep sleep. In one embodiment, the electrodermal activity sensor 724 is incorporated into a wearable device. Alternatively, the electrodermal activity sensor 724 is incorporated into a patch or a bandage.

The environmental sensors 704 include an environmental temperature sensor 725, a humidity sensor 726, a noise sensor 728, an air quality sensor 730, a light sensor 732, and/or a barometric sensor 734. In one embodiment, the environmental temperature sensor 725, the humidity sensor 726, the noise sensor 728, the air quality sensor 730, the light sensor 732, and/or the barometric sensor 734 are built into a home automation system (e.g., Nest). Alternatively, the environmental temperature sensor 725, the humidity sensor 726, the noise sensor 728, and/or the light sensor 732 are incorporated into a smartphone or tablet. In one embodiment, the noise sensor 728 is a microphone. In one embodiment, the air quality sensor 730 measures carbon monoxide, carbon dioxide, nitrogen dioxide, sulfur dioxide, particulates, and/or volatile organic compounds (VOCs).

The remote device 511 is preferably a smartphone or a tablet. Alternatively, the remote device 511 is a laptop or a desktop computer. The remote device 511 includes a processor 760, an analytics engine 762, a control interface 764, and a user interface 766. The remote device 511 accepts data input from the body sensors 702 and/or the environmental sensors 704. The remote device also accepts data input from the remote server 708. The remote device 511 stores data in a local storage 706.

The local storage 706 on the remote device 511 includes a user profile 736, historical subjective data 738, predefined programs 740, custom programs 741, historical objective data 742, and historical environmental data 744. The user profile 736 stores sleep system preferences and information about the user, including but not limited to, age, weight, height, gender, medical history (e.g., sleep conditions, medications, diseases), fitness (e.g., fitness level, fitness activities), sleep goals, stress level, and/or occupational information (e.g., occupation, shift information). The medical history includes caffeine consumption, alcohol consumption, tobacco consumption, use of prescription sleep aids and/or other medications, blood pressure, restless leg syndrome, narcolepsy, headaches, heart disease, sleep apnea, depression, stroke, diabetes, insomnia, anxiety or post-traumatic stress disorder (PTSD), and/or neurological disorders. In one embodiment, the medical history incorporates information gathered from the Epworth Sleepiness Scale (ESS), the Insomnia Severity Index (ISI), Generalized Anxiety Disorder 7-item (GAD-7) Scale, and/or Patient Heath Questionnaire-9 (PHQ-9) (assessment of depression). In one embodiment, the weight of the user is automatically uploaded to the local storage from a third-party application. In one embodiment, the third-party application obtains the information from a smart scale (e.g., Fitbit Aria, Nokia Body, Garmin Index Smart Scale, Under Armour Smart Scale, Pivotal Living Smart Scale, iHealth Wireless Scale).

The historical objective data 742 includes information gathered from the body sensors 702. This includes information from the respiration sensor 712, the electrooculography sensor 713, the heart rate sensor 714, the movement sensor 716, the electromyography sensor 717, the brain wave sensor 718, the body temperature sensor 720, the analyte sensor 721, the pulse oximeter sensor 722, the blood pressure sensor 723, and/or the electrodermal activity sensor 724.

The historical environmental data 744 includes information gathered from the environmental sensors 704. This includes information from the environmental temperature sensor 725, the humidity sensor 726, the noise sensor 728, the air quality sensor 730, the light sensor 732, and/or the barometric sensor 734.

The historical subjective data 738 includes information gathered from manual sleep logs (e.g., Pittsburgh Sleep Quality Index). The manual sleep logs include, but are not limited to, a time sleep is first attempted, a time to fall asleep, a time of waking up, hours of sleep, number of awakenings, times of awakenings, length of awakenings, perceived sleep quality, use of medications to assist with sleep, difficulty staying awake and/or concentrating during the day, difficulty with temperature regulation at night (e.g., too hot, too cold), trouble breathing at night (e.g., coughing, snoring), having bad dreams, waking up in the middle of the night or before a desired wake up time, twitching or jerking in the legs while asleep, restlessness while asleep, difficulty sleeping due to pain, and/or needing to use the bathroom in the middle of the night.

The predefined programs 740 are general sleep settings for various conditions and/or body types (e.g., weight loss, comfort, athletic recovery, hot flashes, bed sores, depression, multiple sclerosis, alternative sleep cycles). In one embodiment, a weight loss predefined program sets a surface temperature at a very cold setting (e.g., 15.56-18.89° C. (60-66° F.)) to increase a metabolic response, resulting in an increase in calories burned, which then leads to weight loss. Temperature settings are automatically adjusted to be as cold as tolerable by the user after the first sleep cycle starts to maximize the caloric burn while having the smallest impact on sleep quality. The core temperature of an overweight individual may fail to drop due to a low metabolism. In one example, the surface temperature is 20° C. (68° F.) at the start of a sleep period, 18.89° C. (66° F.) during N1-N2 sleep, 18.33° C. (65° F.) during N3 sleep, 19.44° C. (67° F.) during REM sleep, and 20° C. (68° F.) to wake the user.

In yet another embodiment, temperature modulation cycles are used to reduce insomnia. Insomnia may be caused by the core body temperature failing to drop or a delay of the drop in core body temperature. In one example, the surface temperature is 20° C. (68° F.) at the start of a sleep period, 17.78° C. (64° F.) during N1-N2 sleep, 15.56° C. (60° F.) during N3 sleep, 18.89° C. (66° F.) during REM sleep, and 20° C. (68° F.) to wake the user.

In still another embodiment, temperature modulation cycles are used to reduce sleep disruptions due to multiple sclerosis (MS). In MS, core temperature and extremity temperature management is not consistent. As a result, a warm to sleep and warm to wake is suggested. In one example, the surface temperature is 37.78° C. (100° F.) at the start of a sleep period, 21.11° C. (70° F.) during N1-N2 sleep, 20° C. (68° F.) during N3 sleep, 26.67° C. (80° F.) during REM sleep, and 37.78° C. (100° F.) to wake the user.

In yet another embodiment, temperature modulation cycles are used to support users with alternative sleep cycles. An alternative sleep cycle is when a user changes to a multiple phase sleep cycle in a 24 hour cycle (e.g., biphasic, segmented, polyphasic sleep). In one example, the surface temperature is 21.11° C. (70° F.) at the start of a sleep period, 17.78° C. (64° F.) during N1-N2 sleep, 16.67° C. (62° F.) during N3 sleep, 19.44° C. (67° F.) during REM sleep, and 21.11° C. (70° F.) to wake the user. This program can repeat for multiple, evenly spaced sleep blocks or be used in a longer block of 4-5 hours. For a short 30 minute block, the temperature drops (e.g., 0.278° C./minute (0.5° F./minute) or greater).

In one embodiment, temperature modulation cycles are used to reduce bed sores. The temperature modulation cycles alternate cooling and heating based on automated collection of risk factors, including temperature, surface area pressure, and moisture (e.g., sweat). In another embodiment, temperature modulation cycles are prescribed by a sleep specialist or physician base on a particular health condition of a user.

The custom programs 741 are sleep settings defined by the user. In one example, the user creates a custom program by modifying a predefined program (e.g., the weight loss program above) to be 1.11° C. (2° F.) cooler during the N3 stage. In another example, the user creates a custom program by modifying a predefined program (e.g., the weight loss program above) to have a start temperature of 37.78° C. (100° F.). The custom programs 741 allow a user to save preferred sleep settings.

The remote server 708 includes global historical subjective data 746, global historical objective data 748, global historical environmental data 750, global profile data 752, a global analytics engine 754, a calibration engine 756, and a simulation engine 758. The global historical subjective data 746, the global historical objective data 748, the global historical environmental data 750, and the global profile data 752 include data from multiple users.

The system components include a mattress pad 11 with adjustable temperature control, a mattress with adjustable firmness 768, a mattress with adjustable elevation 770, an alarm clock 772, a thermostat to adjust the room temperature 774, a lighting system 776, a fan 778, a humidifier 780, and/or a dehumidifier 782.

The body sensors 702, the environmental sensors 704, the remote device 511 with local storage 706, the remote server 708, and the system components 710 are designed to connect directly (e.g., USB or equivalent) or wirelessly (e.g., Bluetooth, Wi-Fi, ZigBee) through systems designed to exchange data between various data collection sources.

Figure 22:
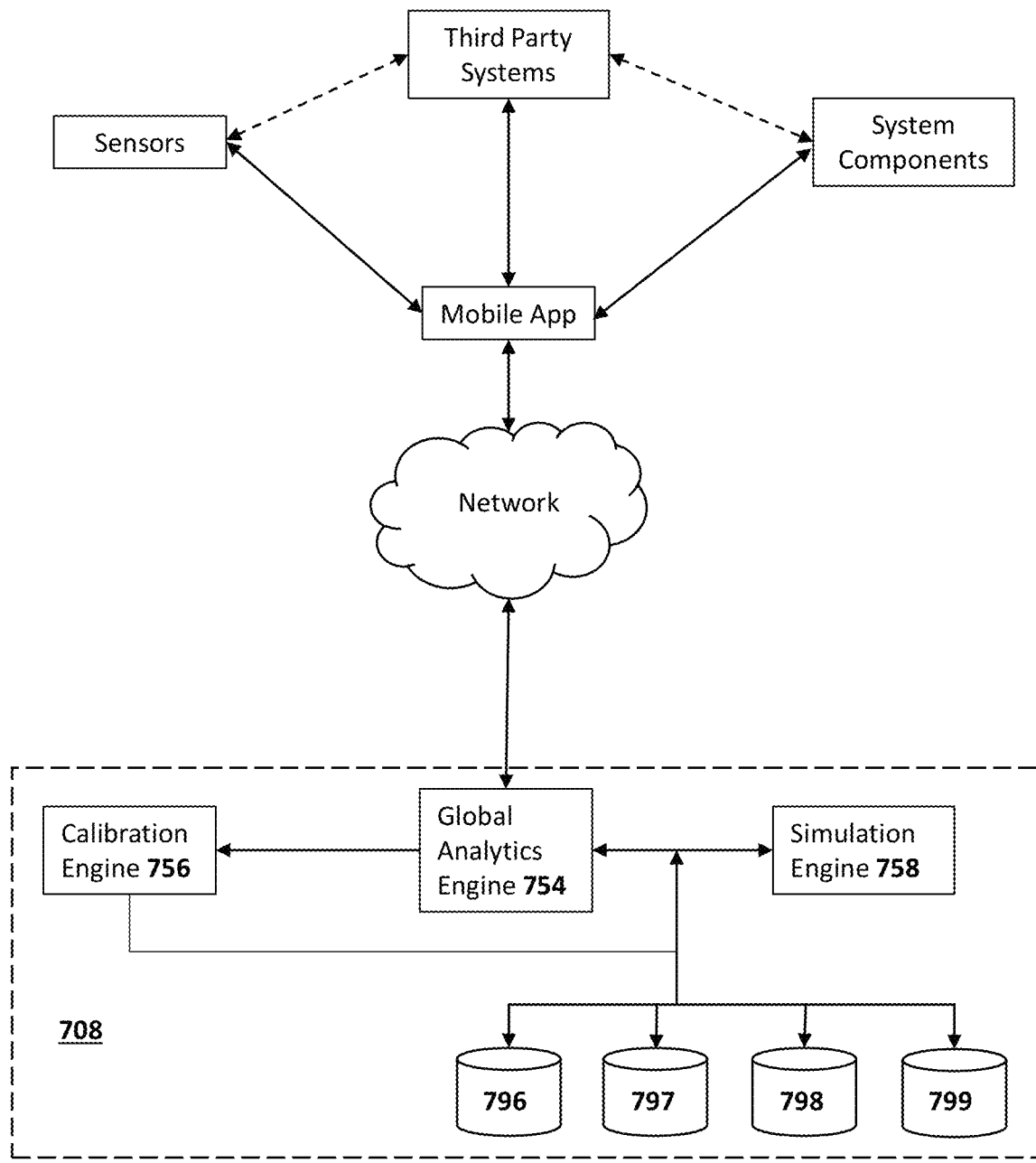
FIG. 22 is a block diagram of one embodiment of the system architecture.

FIG. 22 is a block diagram of one embodiment of the system architecture. The remote device has a mobile application, preferably on a smartphone, which is in wireless communication with sensors 702 and/or 704. The mobile application is operable to communicate with third-party systems (e.g., Fitbit, Jawbone, Nest) and the system components 710. The sensors 702 and/or 704 may communicate information to the mobile application through the third-party systems. The system components 710 may communicate information to the mobile application through the third-party systems. The mobile application communicates with the remote server 708 over the network.

At the start of a sleeping period, a program is selected that provides optimized values for the sleeping period. The program is preferably a predefined program or customized program based on user preferences. In one embodiment, the optimized values include, but are not limited to, sleep stage (e.g., awake, Stage N1, Stage N2, Stage N3, REM Sleep), breath rate, heart rate, brain waves (e.g., beta waves, alpha waves, theta waves, delta waves), blood oxygen rate, body temperature, and/or settings for the system components 710.

Figure 23:
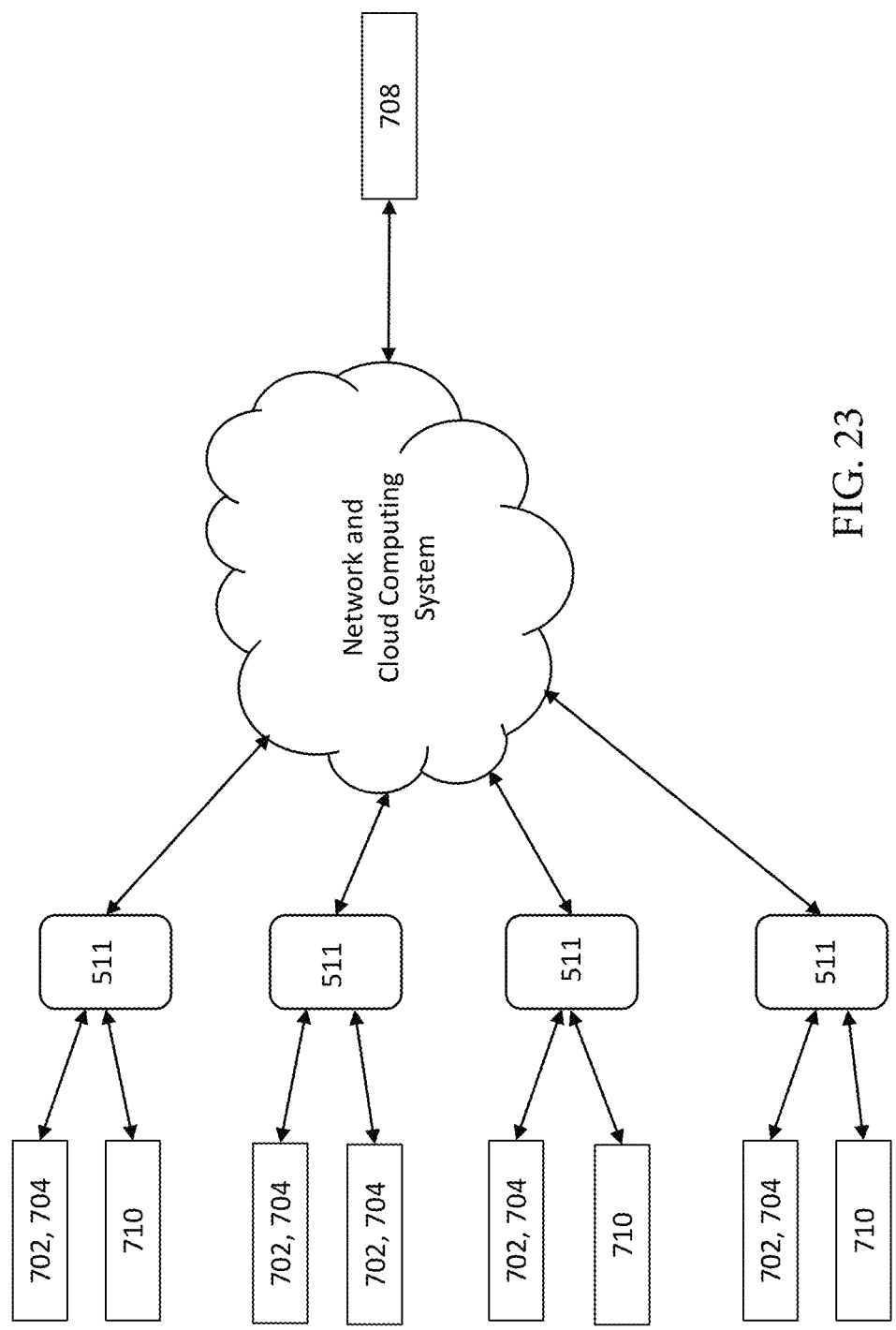
FIG. 23 is an illustration of a network of sleep systems.

As shown in FIG. 23, in one embodiment, the remote server 708 hosts a global analytics engine 754, a calibration engine 756, a simulation engine 758, and databases 796, 797, 798, and 799. Although four databases are shown, it is equally possible to have any number of databases greater than one. The global analytics engine 754 generates predicted values for a monitored sleep system 700 using a virtual model of the sleep system 700 based on real-time data. The calibration engine 756 modifies and updates the virtual model based on the real-time data. Any operational parameter of the virtual model may be modified by the calibration engine 756 as long as the resulting modification is operable to be processed by the virtual model.

The global analytics engine 754 analyzes differences between the predicted values and optimized values. If the difference between the optimized values and the predicted values is greater than a threshold, then the simulation engine 758 determines optimized values of the monitored sleep system 700 based on the real-time data and user preferences. The global analytics engine 754 determines whether a change in parameters of the system components 710 is necessary to optimize sleep based on the output of the simulation engine 758. If a change in parameters is necessary, the new parameters are transmitted to the mobile application on the remote device 511 and then to the system components 710. The calibration engine 756 then updates the virtual model with the new parameters. Thus, the system autonomously optimizes the sleep system (e.g., surface temperature) without requiring input from a user.

FIG. 23 is an illustration of a network of sleep systems. Data from multiple users can be stored on a remote server 708. Although one remote server is shown, it is equally possible to have any number of remote servers greater than one. A user may opt into sending their data to the remote server 708, which is stored in at least one database on the remote server 708. The simulation engine 758 on the remote server 708 is operable to use data from the multiple users to determine customized and optimized sleep settings for the user based on personal preferences (e.g., a target number of hours of sleep, a preferred bed time, a preferred wake time, a faster time to fall asleep, fewer awakenings during the sleeping period, more REM sleep, more deep sleep, and/or a higher sleep efficiency) or physical condition (e.g., weight loss, comfort, athletic recovery, hot flashes, bed sores, depression). In one example, the temperature settings for a temperature-conditioned mattress pad 11 for a user with hot flashes are automatically determined by the simulation engine 758 examining data obtained from other users with hot flashes and a temperature-conditioned mattress pad stored in databases on the remote server 708.

The sleep system 700 includes a virtual model of the sleep system. The virtual model is initialized based on the program selected. The virtual model of the sleep system is dynamic, changing to reflect the status of the sleep system 700 in real time or near-real time. The virtual model includes information from the body sensors 702 and the environmental sensors 704. Based on the data from the body sensors 702 and the environmental sensors 704, the virtual model generates predicted values for the sleep system 700. A sleep stage (e.g., awake, Stage N1, Stage N2, Stage N3, REM sleep) for the user is determined from the data from the body sensors 702.

The sleep system 700 is monitored to determine if there is a change in status of the body sensors 702 (e.g., change in body temperature), the environmental sensors 704 (e.g., change in room temperature), the system components 710 (e.g., change in temperature of mattress pad), or sleep stage of the user. If there is a change in status, the virtual model is updated to reflect the change in status. Predicted values are generated for the sleep system 700. If a difference between the optimized values and the predicted values is greater than a threshold, a simulation is run on the simulation engine 758 to optimize the sleep system 700 based on the real-time data. The simulation engine 758 uses information including, but not limited to, global historical subjective data 746, global historical objective data 748, global historical environmental data 750, and/or global profile data 752 to determine if a change in parameters is necessary to optimize the sleep system 700. In one example, the temperature of the mattress pad 11 is lowered to keep a user in Stage N3 sleep for a longer period of time.

Figure 24:
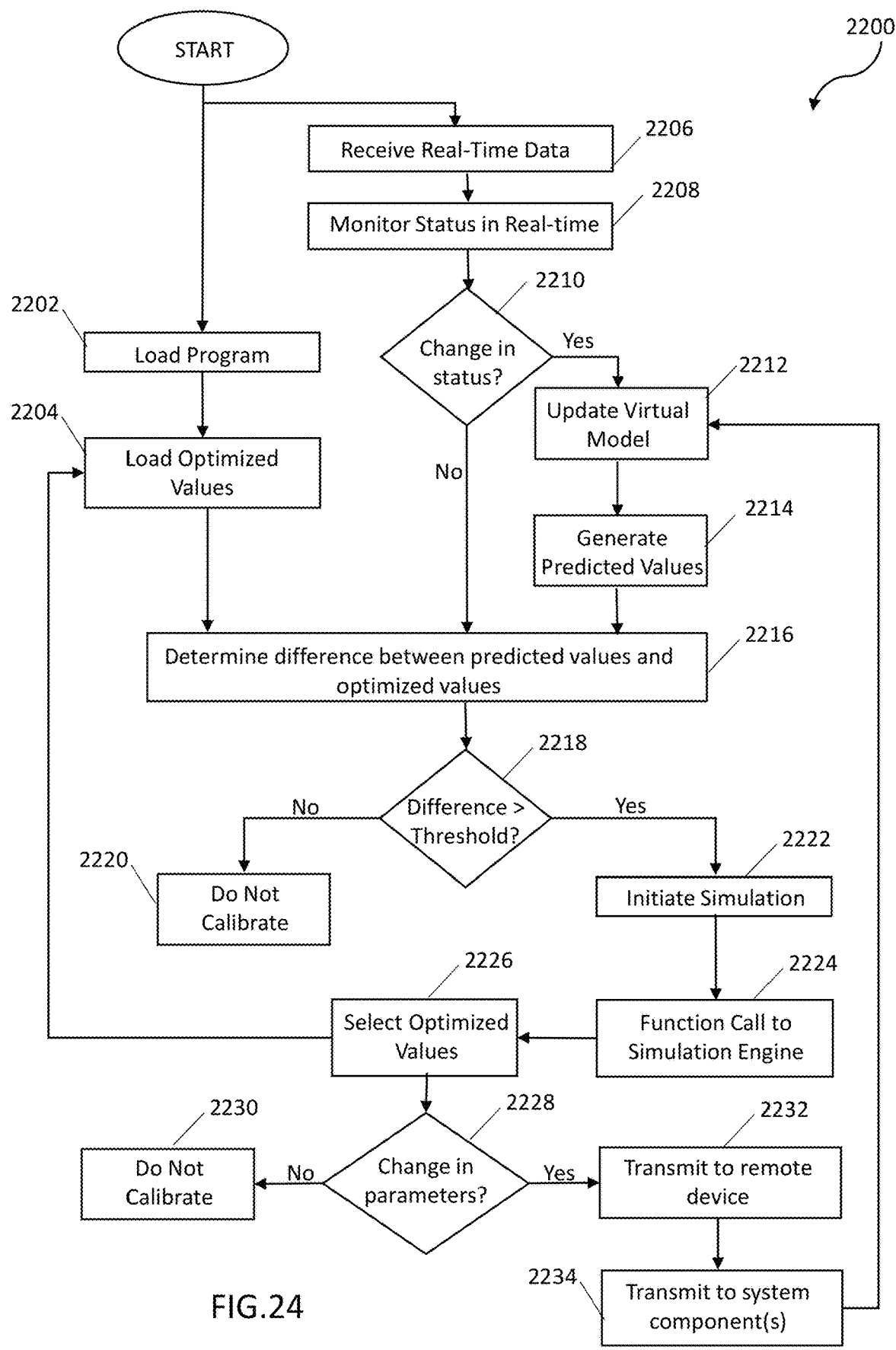
FIG. 24 is a diagram illustrating an example process for monitoring a sleep system and updating a virtual model based on monitored data.

FIG. 24 is a diagram illustrating an example process for monitoring a sleep system 700 and updating a virtual model based on monitored data. First, in step 2202, a program to control the sleep system 700 is loaded onto a remote device 511. In a preferred embodiment, the program is a predefined program or customized program based on user preferences. Optimized values including, but not limited to, the sleep status, parameters for system components 710, and/or times for changes, from the program are loaded onto the global analytics engine 754 in step 2204. Real-time data is received by the remote server 708 via the remote device 511 in step 2206. The real-time data is used to monitor the status of the sleep system 700 in step 2208. As described above, the sleep system 700 includes body sensors 702, environmental sensors 704, a remote device 511 with local storage 706, a remote server 708, and system components 710. Accordingly, the status of the body sensors 702, the environmental sensors 704, and the system components 710 are monitored in step 2208, as well as the sleep status of a user. In step 2210, a determination is made regarding whether there is a change in the status of the monitored devices and/or the sleep state. If there is a change, then the virtual model is updated in step 2212 by the calibration engine 756 to reflect the status change, i.e., the corresponding virtual components data is updated to reflect the actual status of the various monitored devices.

In step 2214, predicted values for the monitored sleep system 700 are generated based on the current, real-time status of the monitored system. In one embodiment, the predicted values include, but are not limited to, sleep stage (e.g., awake, Stage N1, Stage N2, Stage N3, REM Sleep). In step 2216, the optimized values loaded in step 2204 are compared with the predicted values obtained in step 2214.

Accordingly, meaningful predicted values based on the actual condition of monitored sleep system 700 are generated in step 2214. These predicted values are then used to determine if further action should be taken based on the results of the comparison in step 2216. For example, if it is determined in step 2218 that the difference between the predicted values and the optimized values is less than or equal to a threshold, then a do not calibrate instruction is issued in step 2220. If the difference between the real-time data and the predicted values is greater than the threshold, as determined in step 2218, then an initiate simulation command is generated in step 2222.

In step 2224, a function call to the simulation engine 758 is generated in response to the initiate simulation command. The simulation engine 758 selects optimized values for the sleep system 700 in step 2226. These optimized values are updated on the global analytics engine 754 in step 2204. Based on the output of the simulation engine 758, the global analytics engine 754 determines if the optimized values require a change in parameters of the sleep system 700 (e.g., temperature of mattress pad, room temperature, lighting, mattress firmness, mattress elevation) in step 2228. In a preferred embodiment, the simulation engine 758 uses the global historical subjective data 746, the global historical objective data 748, the global historical environmental data 750, and the global profile data 752 to determine if the change in parameters is necessary. If a change in parameters is not necessary, a do not calibrate instruction is issued in step 2230. If a change in parameters is necessary, the new parameters are transmitted to the remote device 511 in step 2232. The remote device 511 transmits the new parameters to the system components 710 in step 2234.

The calibration engine 756 updates the virtual model in step 2212 based on the real-time data and the new parameters. Predicted values are then generated in step 2214. In this manner, the predicted values generated in step 2214 are not only updated to reflect the actual status of monitored sleep system 700, but they are also updated to reflect natural changes in monitored system 700 as the user moves through the sleep cycle. Accordingly, realistic predicted values can be generated in step 2214.

As previously mentioned, the least one remote device 511 preferably has a user interface 766 (e.g., a mobile application for a smartphone or tablet) that allows the sleep system 700 to adjust the parameters of the sleep system. The parameters of the sleep system (e.g., target temperatures of a mattress pad) can be manipulated through the sleeping period using a predefined program or a customized program based on user preferences to produce a deeper, more restful sleep.

Because the target temperatures may be set at any time, those target temperatures may be manipulated through the sleeping period in order to match user preferences or a program to correlate with user sleep cycles to produce a deeper, more restful sleep.

In one embodiment, the mobile application measures a time when a user began attempting to sleep (TATS), a TATS start time, a TATS end time, a time in bed (TIB), a TIB start time, and/or a TIB end time. The mobile application calculates a total TATS duration based on the TATS start time and the TATS end time. The mobile application also calculates a total TIB duration based on the TIB start time and the TIB end time. In one embodiment, the TATS start time, the TATS end time, the TIB start time, and/or the TIB end time are indicated by the user (e.g., by pressing a button in the mobile application). Alternatively, the TATS start time, the TATS end time, the TIB start time, and/or the TIB end time are determined by sensors. In one example, the TATS start time is determined by a user's eyes closing while in bed. In another example, the TATS end time is determined by increased motion as measured by a movement sensor and/or opening of the eyes. In yet another example, the TIB start time is determined by sensors indicating a user is horizontal and/or bed or room sensors indicating the user is in bed. In still another example, the TIB end time is determined by sensors indicating a user is not horizontal and/or bed or room sensors indicating the user is not in bed.

The mobile application is operable to determine whether a user is awake or asleep. The state of wakefulness (i.e., "awake") is characterized by cognitive awareness and/or consciousness, responsiveness to environmental cues, sustained movement detected by a movement sensor, beta and/or alpha waves as detected by EEG, increased heart rate, increased respiration, increased blood pressure, increased electrodermal activity, increased body temperature, open eyes, voluntary eye movements, and/or increased EMG on the chin. The state of sleep (i.e., "asleep") is characterized by loss of alertness and/or consciousness, lack of response to environmental cues, lack of movement, reduction in alpha waves as detected by EEG, increased theta and delta waves as detected by EEG, decreased heart rate, decreased respiration, decreased blood pressure, decreased body temperature, closed eyes, eye twitches, and/or decreased oxygen saturation.

In a preferred embodiment, the mobile application is operable to measure an initial sleep onset time and/or a final awakening time. The initial sleep onset time is a first occurrence of sleep after the TATS start time. The final awakening time is a time immediately after the last occurrence of sleep before the TATS end time. In one embodiment, the mobile application calculates a latency to sleep onset as the duration of a time interval between the TATS start time to the initial sleep onset time. In another embodiment, the mobile application calculates a latency to arising as the duration of a time interval between the final awakening time to the TATS end time. In a preferred embodiment, the mobile application is operable to calculate a sleep efficiency percentage. In one embodiment, the sleep efficiency percentage is defined as the total sleep time divided by the total TATS duration. In an alternative embodiment, the sleep efficiency percentage is defined as the total sleep time divided by the total TIB duration.

In one embodiment, the mobile application is operable to determine a total sleep period duration, a total sleep time, a sleep maintenance percentage, a total wakefulness duration, a wakefulness duration after initial sleep onset, a total number of awakenings, an awakening rate per hour, and/or a sleep fragmentation rate.

In another embodiment, the mobile application is operable to determine REM sleep, N1 sleep, N2 sleep, and/or N3 sleep. REM sleep is characterized by low-voltage, mixed-frequency EEG activity with less than 15 seconds of alpha activity, saw-tooth theta EEG activity, rapid eye movements, and/or decreased or absent EMG activity on the chin. N1 sleep is characterized by low-voltage, mixed-frequency EEG activity with less than 15 seconds of alpha activity in a 30-second epoch, no sleep spindles or K complexes, possible slow rolling eye movements, and/or diminished EMG activity on the chin. N2 sleep is characterized by sleep spindle and/or K complex activity, absence of eye movements, and/or diminished EMG activity on the chin. N3 sleep is characterized by high amplitude (e.g., greater than 75 µV peak-to-peak), slow wave (e.g., frequency of 4 Hz or less) EEG activity. In yet another embodiment, the mobile application is operable to calculate REM sleep duration, percentage, and latency from sleep onset; N1 sleep duration, percentage, and latency from sleep onset; N2 sleep duration, percentage, and latency from sleep onset; and/or N3 sleep duration, percentage, and latency from sleep onset.

Alternatively, the calculations and determining of sleep states described above are determined over the network on a remote server. In one embodiment, the calculations and determining of sleep states are then transmitted to at least one remote device.

Figure 25:
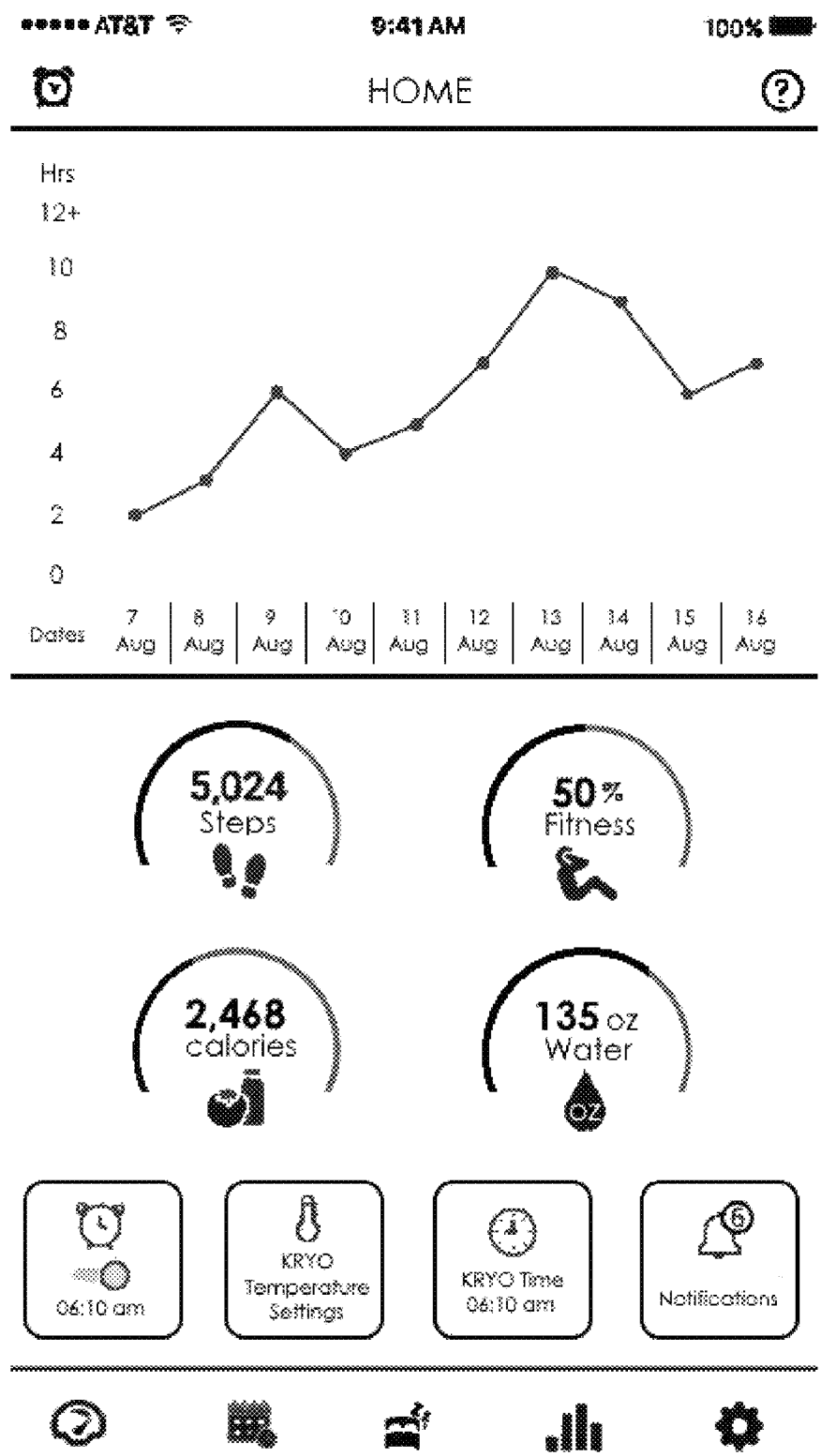
FIG. 25 illustrates a home screen of one embodiment of a graphical user interface (GUI) for a mobile application.

FIG. 25 illustrates a home screen of one embodiment of a graphical user interface (GUI) for a mobile application. A bottom navigation bar allows a user to rapidly switch between destinations within the mobile application. In FIG. 25, the bottom navigation bar includes (in order from left to right) icons for the home screen, a schedule screen, a sleep screen, a progress screen, and a goal settings screen.

The home screen includes a graph of the number of hours a user slept versus dates. In this example, the graph provides the number of hours a user slept for the previous 10 days. In one embodiment, the number of hours a user slept for a day is obtained from a wearable device (e.g., Fitbit, Jawbone UP, Misfit, Apple Watch, Nokia Steel, Nokia Go). Alternatively, the user manually enters a time the user went to sleep and a time the user woke up.

The home screen also provides a current snapshot of the user's daily health information. The user's daily health information includes, but is not limited to, the number of steps the user has taken, the percentage of fitness goals achieved, the number of calories consumed by the user, and the amount of water consumed by the user. This information is preferably updated in real time or near-real time by the mobile application. In one embodiment, this information is manually entered into the mobile application. Alternatively, this information is obtained from third-party applications (e.g., Fitbit, Jawbone, Misfit, MyFitnessPal, Apple Health, Health Mate).

The home screen allows the user to set a smart alarm (e.g., 6:10 AM). The smart alarm increases the surface temperature of the mattress pad sufficiently over a period of time to allow the user to emerge out of the last sleep cycle. The speed of awakening is based on the sleep cycle information. The speed of temperature increase is faster (e.g., 0.278° C./minute (0.5° F./minute)) if a new cycle is just beginning. The speed of temperature increase is slower (e.g., 0.056° C./minute (0.1° F./minute)) if the user is just coming out of the bottom of a sleep cycle. In one embodiment, the mobile application uses active data collection of the user's vital signs, including, but not limited to, heart rate, breath rate, blood oxygen level, brain waves, and/or skin temperature, to determine the speed of awakening.

Figure 26:
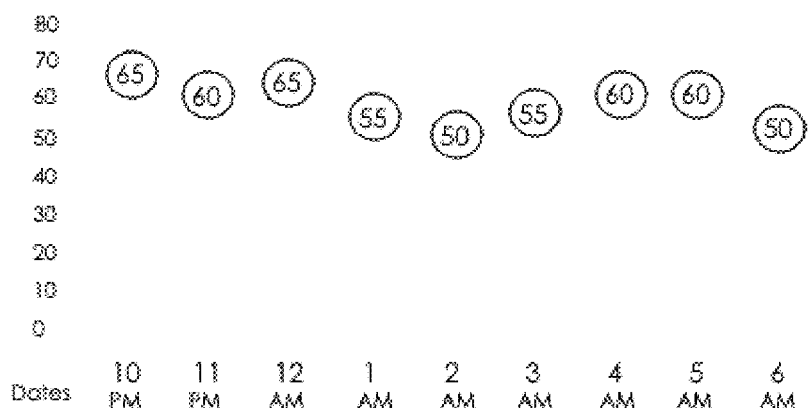
FIG. 26 illustrates a schedule screen of one embodiment of a GUI for a mobile application.

FIG. 26 illustrates a schedule screen of one embodiment of a GUI for a mobile application. The mobile application allows a user to select a temperature schedule. In FIG. 25, the temperature varies between 10-18.33° C. (50-65° F.) between 10 PM and 6 AM. The schedule screen displays a graph of temperature versus time.

Figure 27:
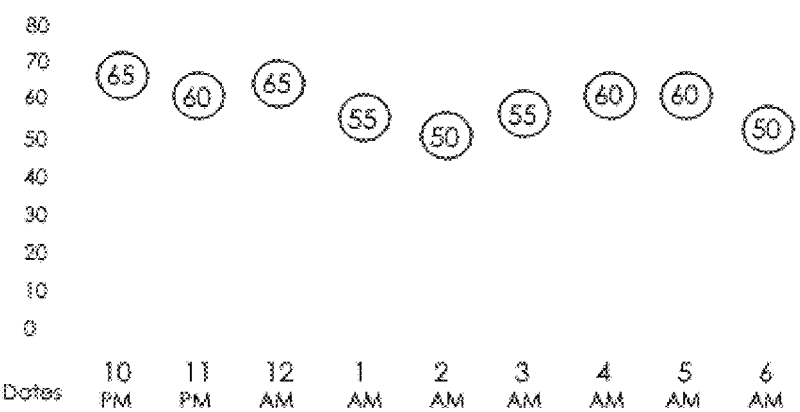
FIG. 27 illustrates another schedule screen of one embodiment of a GUI for a mobile application.

FIG. 27 illustrates another schedule screen of one embodiment of a GUI for a mobile application. The mobile application allows a user to select a sleep time and a wake time.

Figure 28:
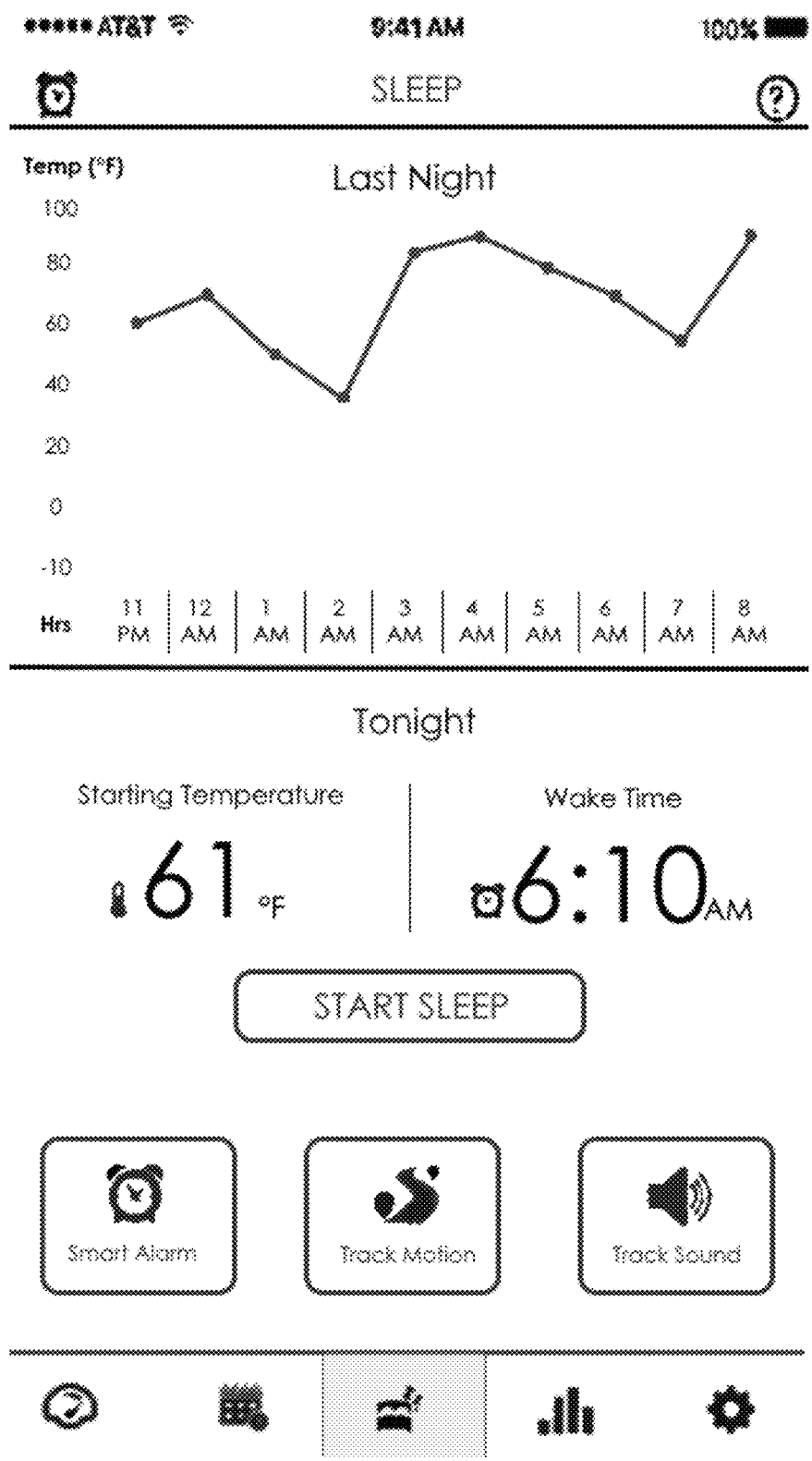
FIG. 28 illustrates a sleep screen of one embodiment of a GUI for a mobile application.

FIG. 28 illustrates a sleep screen of one embodiment of a GUI for a mobile application. The sleep screen displays a graph of time versus temperature for the previous day. The sleep screen displays a starting temperature and a wake time for the sleeping period. The user can select a "start sleep" button to manually track sleep cycles.

The sleep screen also has a button for a smart alarm. This allows the mobile application to adjust the settings of the mattress pad to wake the user at an optimal time within a sleep cycle. As previously described, gently awakening the user by increasing the temperature prevents sleep inertia. The sleep screen also has a button for tracking motion of the user. Further, the sleep screen also has a button for tracking sound of the user.

Figure 29:
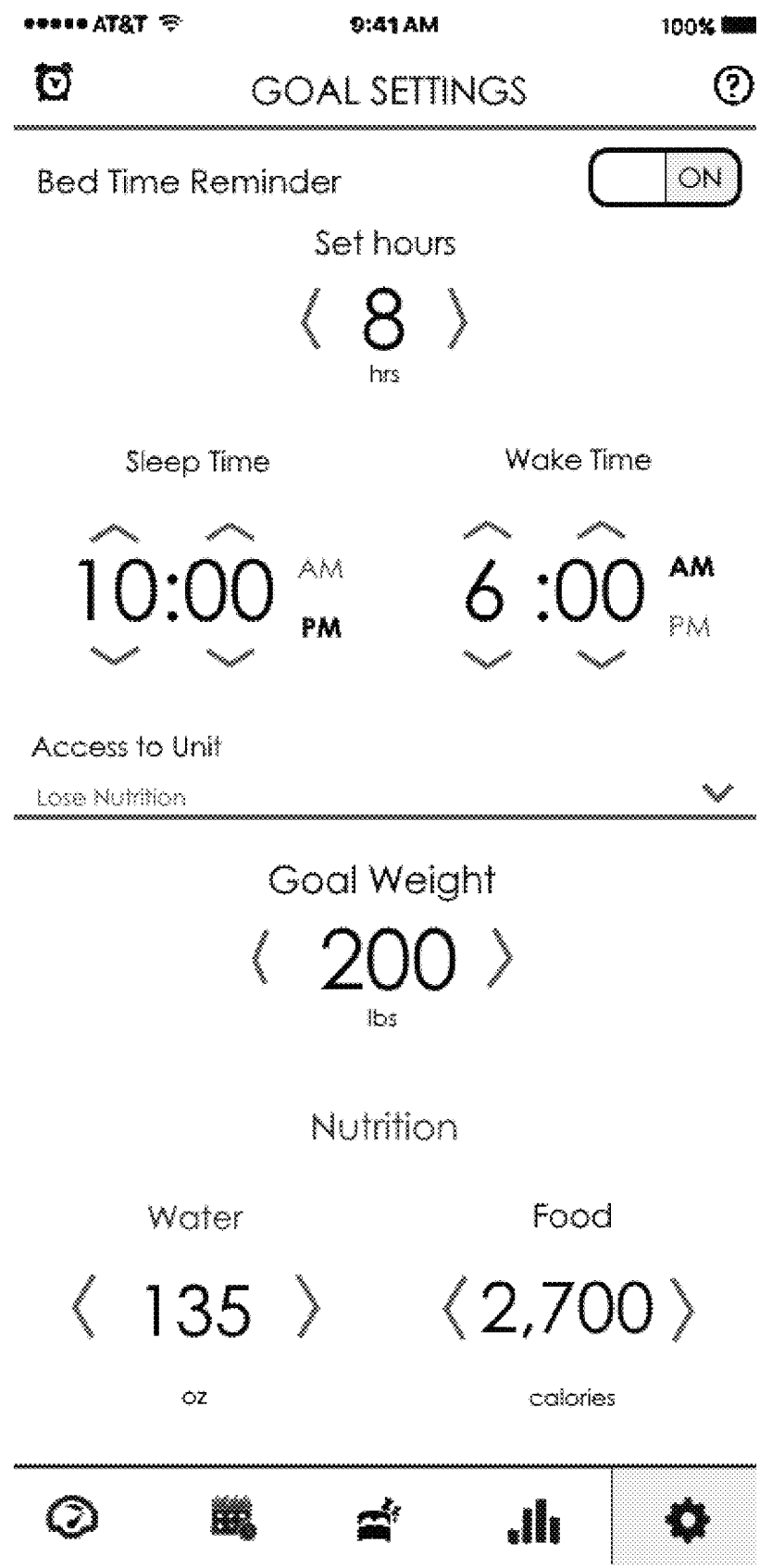
FIG. 29 illustrates a goal settings screen for one embodiment of a GUI for a mobile application.

FIG. 29 illustrates a goal settings screen for one embodiment of a GUI for a mobile application. The goal settings screen allows a user to turn a bed time reminder on or off and select a target number of hours of sleep (e.g., 8 hours). The goal settings screen also allows a user to select a preferred sleep time (e.g., 10:00 PM) and a preferred wake time (e.g., 6:00 AM). The goal settings screen also allows a user to set a goal weight, goal amount of water to consume, and goal number of calories to consume. Additional goals include, but are not limited to, a faster time to fall asleep, fewer awakenings during the sleeping period, more REM sleep, more deep sleep (e.g., N3 sleep), and/or a higher sleep efficiency.

Figure 30:
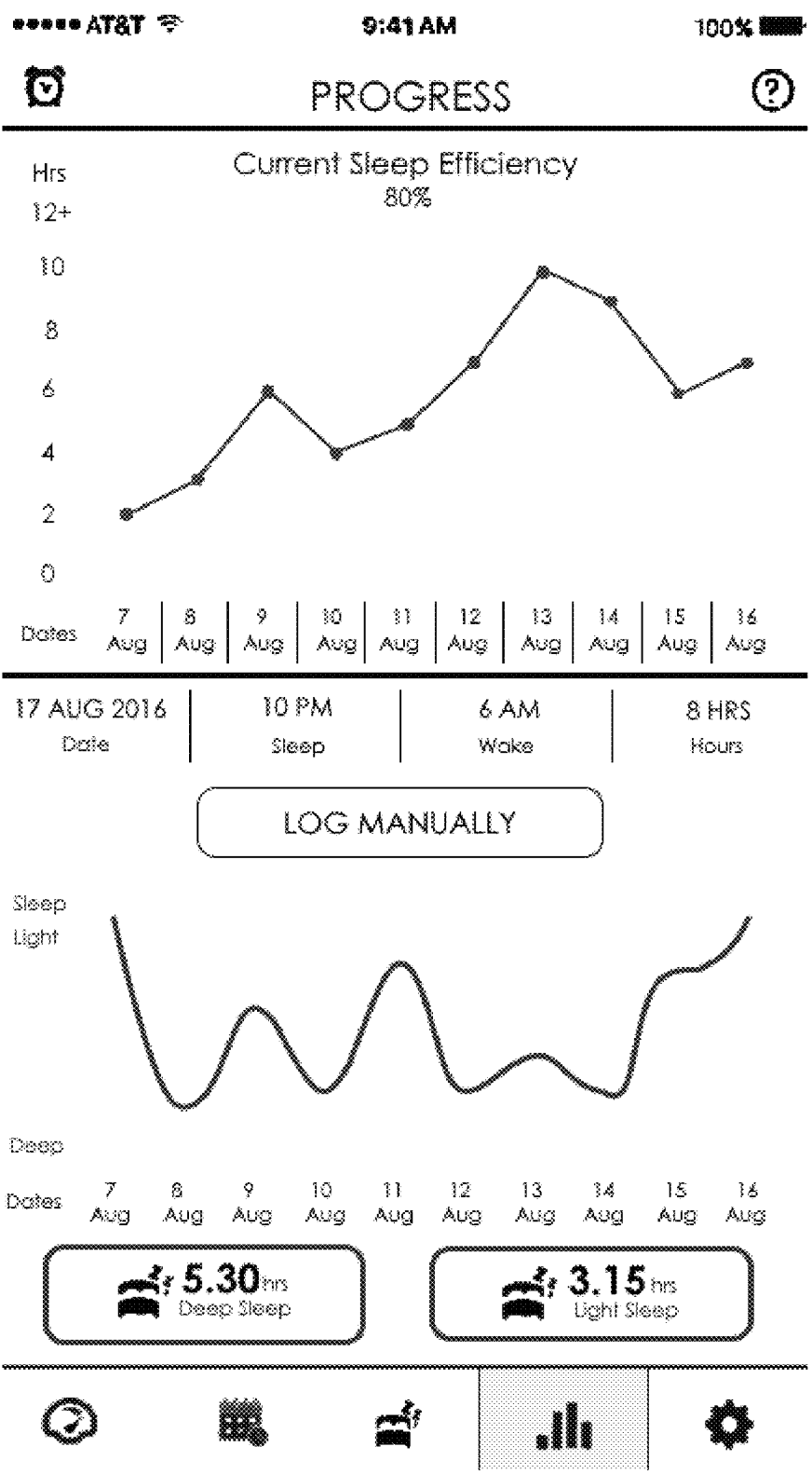
FIG. 30 illustrates a progress screen for one embodiment of a GUI for a mobile application.

FIG. 30 illustrates a progress screen for one embodiment of a GUI for a mobile application. The progress screen includes a graph of the number of hours a user slept versus dates. In this example, the graph provides the number of hours a user slept for the previous 10 days. The progress screen displays a current sleep efficiency (e.g., 80%). The progress screen lists the current date, a sleep time, a wake time, and number of hours of sleep. A "log manually" button allows the user to manually log sleep. The progress screen also includes a graph of the depth of sleep (e.g., light or deep) versus dates. In this example, the graph provides the depth of sleep for the previous 10 days. The progress screen displays a time spent in deep sleep (e.g., 5.30 hrs) and a time spent in light sleep (e.g., 3.15 hrs).

Figure 31:
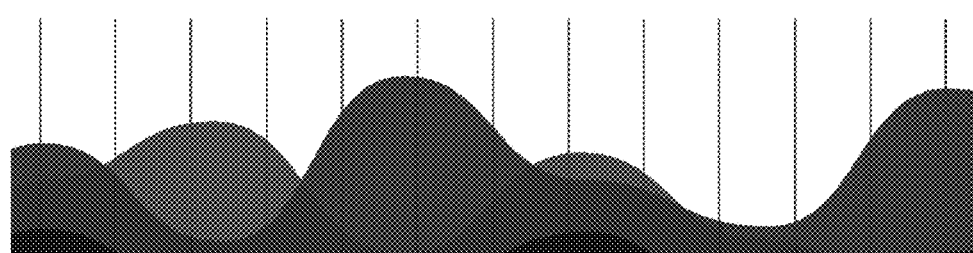
FIG. 31 illustrates a profile screen for one embodiment of a GUI for a mobile application.

FIG. 31 illustrates a profile screen for one embodiment of a GUI for a mobile application. In this embodiment, the mobile application includes a social component. The mobile application allows users to upload photos. The mobile application also allows users to follow other users. In this example, the user has 863 followers. A notification illustrates that the user has 4 new followers. Additionally, the mobile application allows users to like status updates and photos of other users. In this example, the user has posted 2471 photos and has 1593 likes. A notification illustrates that the user has 7 new likes. Further, the GUI displays statistics for the number of likes, followers, and photos over several months.

Figure 32:
FIG. 32 illustrates another profile screen for one embodiment of a GUI for a mobile application.
Figure 32:
Figure 32:
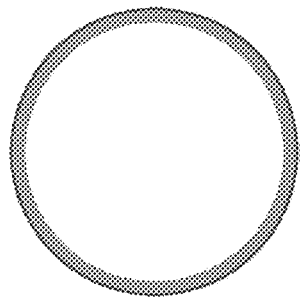
Figure 32:
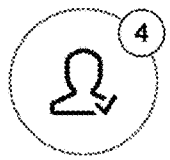
Figure 32:
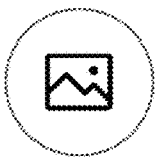
Figure 32:
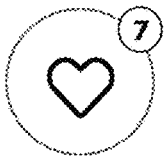
Figure 32:
Figure 32:
Figure 32:
Figure 32:
Figure 32:
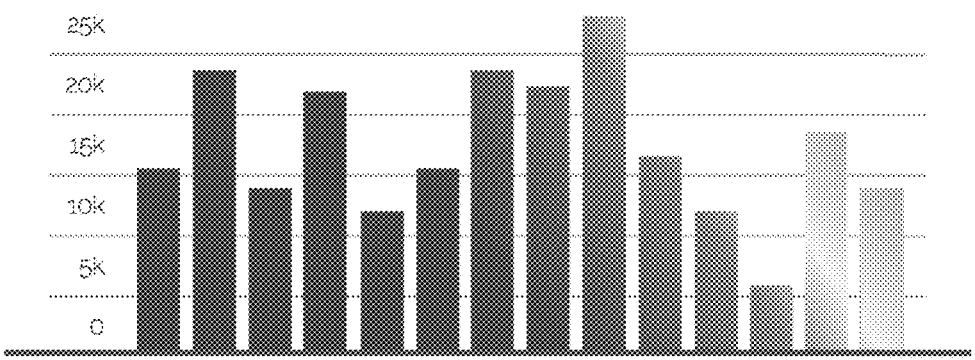
Figure 32:
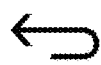
Figure 32:
Figure 32:

FIG. 32 illustrates another profile screen for one embodiment of a GUI for a mobile application. In this example, the mobile application is operable to send messages between users.

Figure 33:
FIG. 33 illustrates yet another profile screen for one embodiment of a GUI for a mobile application.
Figure 33:
Figure 33:
Figure 33:
Figure 33:
Figure 33:
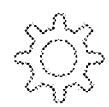

FIG. 33 illustrates yet another profile screen for one embodiment of a GUI for a mobile application. In this example, the profile screen displays a weekday sleep time of 10 PM and a weekday wake up time of 6 AM. The profile screen also displays a weekend sleep time of 10 PM and a weekend wake up time of 6 AM. The profile screen includes a button to add sleep profile. A bottom navigation bar allows a user to rapidly switch between destinations within the mobile application. In FIG. 33, the bottom navigation bar includes (in order from left to right) icons for a temperature screen, a sleep screen, an alarm screen, a notification screen, and a settings screen.

Figure 34:
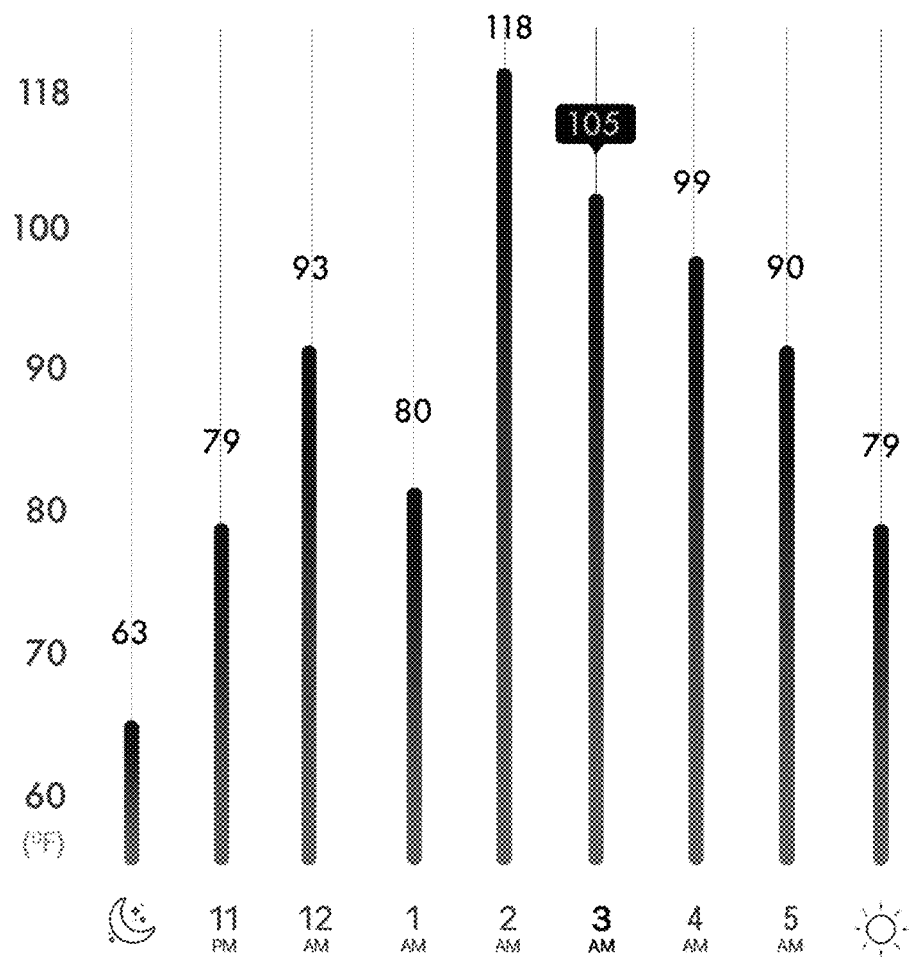
FIG. 34 illustrates an add sleep profile screen for one embodiment of a GUI for a mobile application.

FIG. 34 illustrates an add sleep profile screen for one embodiment of a GUI for a mobile application. The mobile application is operable to allow the user to set a sleep time and a wake up time. Further, the mobile application is operable to allow a user to select temperatures for a mattress pad over a sleep period. In this example, the temperature is set at 17.22° C. (63° F.) at 10 PM, 26.11° C. (79° F.) at 11 PM, 33.89° C. (93° F.) at 12 AM, 26.67° C. (80° F.) at 1 AM, 47.78° C. (118° F.) at 2 AM, 40.56° C. (105° F.) at 3 AM, 37.22° C. (99° F.) at 4 AM, 32.22° C. (90° F.) at 5 AM, and 26.11° C. (79° F.) at 6 AM. Further, the mobile application allows the user to select warm awake, which slowly (e.g., 0.278° C./minute (0.5° F./minute)) warms the user to awaken the user.

Figure 35:
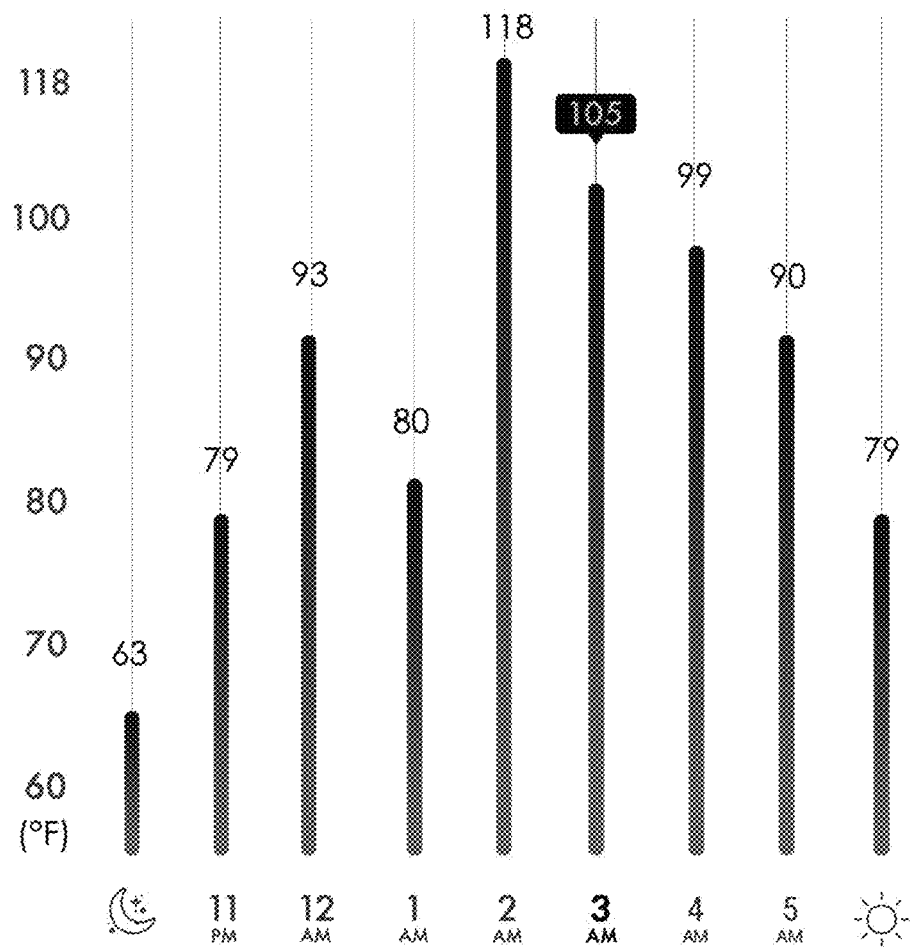
FIG. 35 illustrates a dashboard screen for one embodiment of a GUI for a mobile application.

FIG. 35 illustrates a dashboard screen for one embodiment of a GUI for a mobile application. In this embodiment, the mobile application is operable to allow the user to check the water level of the at least one reservoir in the control unit. In a preferred embodiment, the mobile application notifies the user when the water level is below a threshold. Further, the mobile application allows the user to display sleep efficiency.

In another embodiment, the mobile application notifies the user that water treatment or purification is required. In another embodiment, the mobile application automatically schedules water treatment or purification (e.g., automatically turning on the UV light for water treatment) at designated time intervals.

Most individuals adopt a monophasic sleep pattern (e.g., sleeping 6-8 hours at a time). Non-monophasic sleep occurs when an individual adopts a biphasic or polyphasic sleep pattern. A biphasic sleep pattern is when the individual sleeps twice per day. Typically, this consists of a shorter rest (e.g., "siesta") during the day and a longer sleep period during the night. A polyphasic sleep pattern (e.g., Everyman, Uberman, Dymaxion, Dual Core) consists of multiple sleeps throughout the day, generally ranging from 4 to 6 periods of sleep per day.

Figure 36:
FIG. 36 illustrates a profile screen for one embodiment of a GUI for a mobile application allowing for segmented sleep.
Figure 36:
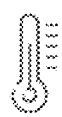
Figure 36:
Figure 36:
Figure 36:
Figure 36:
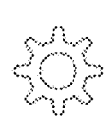

FIG. 36 illustrates a profile screen for one embodiment of a GUI for a mobile application allowing for biphasic sleep. In this example, the user sleeps from 1 PM to 3 PM and 11 PM to 5 AM on weekdays. The user also sleeps from 1 PM to 3 PM and 2 AM to 9 AM on weekends.

Although FIGS. 33 and 36 show weekday and weekend sleep schedules, the mobile application is operable to allow users to set specific sleep schedules for each day of the week. In one example, the mobile application allows the user to set different sleep schedules for Monday through Thursday (e.g., work days of a compressed work week), Friday, Saturday, and Sunday.

Figure 37:
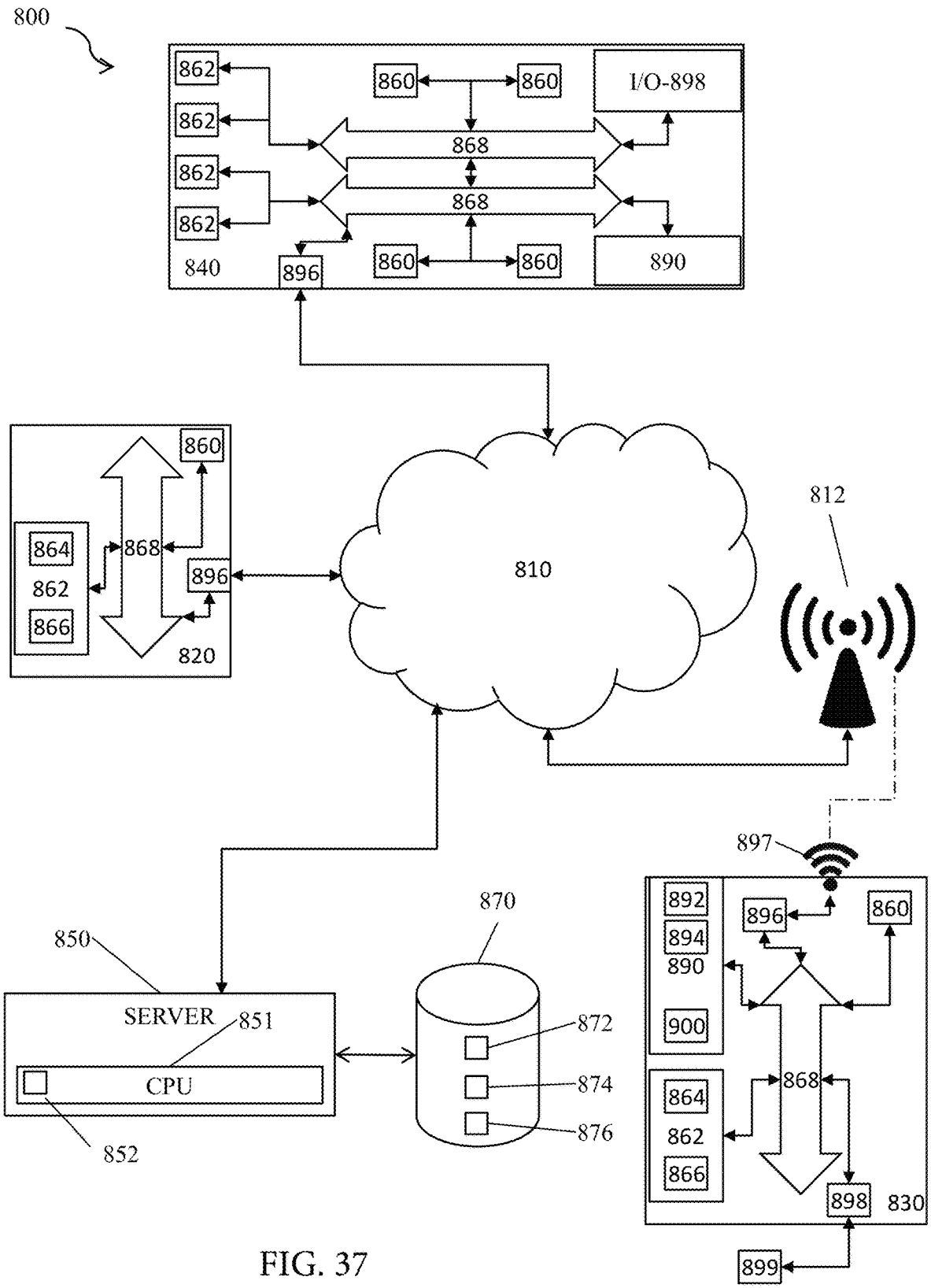
FIG. 37 shows a schematic diagram illustrating general components of a cloud-based computer system.

FIG. 37 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 37, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multi-processor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 37, may include other components that are not explicitly shown in FIG. 37, or may utilize an architecture completely different than that shown in FIG. 37. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By way of example, the temperature regulating article can be a mattress pad, a sleeping bag, a cushion, or a blanket. The above-mentioned examples are just some of the many configurations that the mentioned components can take on. All modifications and improvements have been deleted herein for the sake of conciseness and readability but are properly within the scope of the present invention.

The invention claimed is:

1. An article for temperature-conditioning a surface comprising:
   a first layer having a plurality of openings, wherein the first layer has an exterior surface and an interior surface;
   a second layer having a corresponding plurality of openings, wherein the second layer has an exterior surface and an interior surface, and wherein the second layer is permanently affixed to the first layer along a periphery of the article and a periphery of each of the plurality of openings;
   at least one interior chamber defined between the interior surface of the first layer and the interior surface of the second layer;
   at least one flexible fluid supply line for delivering a fluid to the at least one interior chamber;
   at least one flexible fluid return line for removing the fluid from the at least one interior chamber; and
   at least one thermoelectric control unit attached to the at least one flexible fluid supply line and the at least one flexible fluid return line, wherein the at least one thermoelectric control unit is operable to selectively cool or heat the fluid;
   wherein the at least one interior chamber is constructed and configured to retain the fluid without leaking;
   wherein the interior surface of the first layer and the interior surface of the second layer are comprised of at least one layer of a waterproof material;
   wherein the at least one thermoelectric control unit is in real-time or near-real-time two-way communication with at least one remote device;
   wherein the at least one remote device comprises a mobile application, and wherein a graphical user interface (GUI) on the mobile application includes a smart alarm, wherein the smart alarm causes a temperature of the article to be increased based on a user's location in a sleep cycle;
   wherein the user's location in the sleep cycle is determined by active data collection of the user's vital signs;
   wherein the at least one flexible fluid supply line and the at least one flexible fluid return line are contained in a flexible hose; and
   wherein a mattress pad hose elbow is concentric around the flexible hose, wherein the mattress pad hose elbow secures the flexible hose to a side of a mattress, and wherein the mattress pad hose elbow is operable to slide along the flexible hose.

2. The article of claim 1, wherein the fluid is water.

3. The article of claim 1, wherein each of the plurality of openings is in a shape of a hexagon, a triangle, a circle, a rectangle, a square, an oval, a diamond, a pentagon, a heptagon, an octagon, a nonagon, a decagon, a trapezium, a parallelogram, a rhombus, a cross, a semicircle, a crescent, a heart, a star, a snowflake, and/or any other polygon.

4. The article of claim 1, wherein the plurality of openings comprises at least 15% of a surface area of the article.

5. The article of claim 1, further comprising a first panel attached to a first side of the article at a first attachment point and a second panel attached to a second side of the article at a second attachment point, wherein the first attachment point is between the first layer and the second layer, wherein the second attachment point is between the first layer and the second layer, wherein the second attachment point is on an opposite side of the article from the first attachment point, wherein a first non-slip piece is attached to the first panel on a side opposite the first attachment point, and wherein a second non-slip piece is attached to the second panel on a side opposite the second attachment point.

6. The article of claim 1, wherein the waterproof material is a urethane.

7. The article of claim 1, wherein the exterior surface of the first layer and/or the exterior surface of the second layer are comprised of a copper ion or a silver ion thread.

8. The article of claim 1, further comprising side panels and end panels attached to sides and ends of the article, respectfully; wherein a top non-slip piece and a bottom non-slip piece are attached to each corner formed by the side panels and end panels.

9. The article of claim 8, wherein the top non-slip piece and the bottom non-slip piece are comprised of foam.

10. The article of claim 1, further comprising a spacer layer positioned within the at least one interior chamber.

11. A sleep system comprising:
at least one remote device; and
an article for adjusting a temperature of a surface, wherein the article further comprises:
a first layer having a plurality of openings, wherein the first layer has an exterior surface and an interior surface;
a second layer having a corresponding plurality of openings, wherein the second layer has an exterior surface and an interior surface, and wherein the second layer is permanently affixed to the first layer along a periphery of the article and a periphery of each of the plurality of openings;
at least one interior chamber defined between the interior surface of the first layer and the interior surface of the second layer;
at least one flexible fluid supply line for delivering a fluid to the at least one interior chamber;
at least one flexible fluid return line for removing the fluid from the at least one interior chamber; and
at least one control unit attached to the at least one flexible fluid supply line and the at least one flexible fluid return line, wherein the at least one control unit is operable to selectively cool or heat the fluid, and wherein the at least one control unit has at least one antenna and at least one processor;
wherein the at least one remote device and the at least one control unit have real-time or near-real-time two-way communication;
wherein the at least one interior chamber is constructed and configured to retain the fluid without leaking;
wherein the interior surface of the first layer and the interior surface of the second layer are comprised of at least one layer of a waterproof material;
wherein the at least one remote device comprises a mobile application, and wherein a graphical user interface (GUI) on the mobile application includes a smart alarm, wherein the smart alarm causes a temperature of the article to be increased based on a user's location in a sleep cycle;
wherein the user's location in the sleep cycle is determined by active data collection of the user's vital signs;
wherein the at least one flexible fluid supply line and the at least one flexible fluid return line are contained in a flexible hose; and
wherein a mattress pad hose elbow is concentric around the flexible hose, wherein the mattress pad hose elbow secures the flexible hose to a side of a mattress, and wherein the mattress pad hose elbow is operable to slide along the flexible hose.

12. The sleep system of claim 11, further comprising at least one remote server having real-time or near-real-time two-way communication with the at least one remote device.

13. The sleep system of claim 11, further comprising at least one body sensor and/or at least one environmental sensor.

14. The sleep system of claim 13, wherein the at least one body sensor is a respiration sensor, a heart rate sensor, a movement sensor, a brain wave sensor, a body temperature sensor, an analyte sensor, a blood pressure sensor, and/or a pulse oximeter sensor.

15. The sleep system of claim 11, wherein the at least one control unit is operable to receive parameters from the at least one remote device to modify the temperature of the surface.

16. The sleep system of claim 15, wherein the at least one remote device wirelessly transmits the parameters via Bluetooth, radiofrequency, ZigBee, Wi-Fi, or near field communication.

17. A sleep system comprising:
at least one body sensor;
at least one remote device;
at least one remote server; and
an article for adjusting a temperature of a surface, wherein the article further comprises:
a first layer having a plurality of openings, wherein the first layer has an exterior surface and an interior surface;
a second layer having a corresponding plurality of openings, wherein the second layer has an exterior surface and an interior surface, and wherein the second layer is permanently affixed to the first layer along a periphery of the article and a periphery of each of the plurality of openings;
at least one interior chamber defined between the interior surface of the first layer and the interior surface of the second layer;
at least one flexible fluid supply line for delivering a fluid to the at least one interior chamber;
at least one flexible fluid return line for removing the fluid from the at least one interior chamber; and
at least one control unit attached to the at least one flexible fluid supply line and the at least one flexible fluid return line, wherein the at least one control unit is operable to selectively cool or heat the fluid, and wherein the at least one control unit has at least one antenna and at least one processor;
wherein the at least one body sensor and the at least one remote device have real-time or near-real-time two-way communication;
wherein the at least one remote server and the at least one remote device have real-time or near-real-time two-way communication;
wherein the at least one remote device and the at least one control unit have real-time or near-real-time two-way communication;
wherein the at least one remote server is operable to determine optimized parameters for the article based on data from the at least one body sensor;
wherein the at least one remote server is operable to transmit the optimized parameters for the article to the at least one remote device;

wherein the at least one remote device is operable to transmit the optimized parameters for the article to the at least one control unit;

wherein the at least one interior chamber is constructed and configured to retain the fluid without leaking;

wherein the interior surface of the first layer and the interior surface of the second layer are comprised of at least one layer of a waterproof material;

wherein the at least one remote device comprises a mobile application, and wherein a graphical user interface (GUI) on the mobile application includes a smart alarm, wherein the smart alarm causes a temperature of the article to be increased based on a user's location in a sleep cycle;

wherein the user's location in the sleep cycle is determined by active data collection of the user's vital signs;

wherein the at least one flexible fluid supply line and the at least one flexible fluid return line are contained in a flexible hose; and wherein a mattress pad hose elbow is concentric around the flexible hose, wherein the mattress pad hose elbow secures the flexible hose to a side of a mattress, and wherein the mattress pad hose elbow is operable to slide along the flexible hose.

18. The sleep system of claim 17, wherein the at least one body sensor is a respiration sensor, a heart rate sensor, a movement sensor, a brain wave sensor, a body temperature sensor, a blood glucose sensor, a blood pressure sensor, and/or a pulse oximeter sensor.

\* \* \* \* \*